United States Patent
Neises et al.

(12)

(10) Patent No.: US 6,667,334 B1
(45) Date of Patent: *Dec. 23, 2003

(54) IMIDAZOLIDINE DERIVATIVES, THE PRODUCTION THEREOF, THEIR USE AND PHARMACEUTICAL PREPARATIONS CONTAINING THE SAME

(75) Inventors: Bernhard Neises, Offenburg (DE); Volkmar Wehner, Sandberg (DE); Hans Ulrich Stilz, Frankfurt (DE)

(73) Assignee: Aventis Pharma Deutschland GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/700,178

(22) PCT Filed: May 5, 1999

(86) PCT No.: PCT/EP99/03072
§ 371 (c)(1),
(2), (4) Date: Mar. 12, 2001

(87) PCT Pub. No.: WO99/60015
PCT Pub. Date: Nov. 25, 1999

(30) Foreign Application Priority Data

May 14, 1998 (DE) ........................................ 198 21 483

(51) Int. Cl.[7] .................... A61K 31/4166; C07D 233/76
(52) U.S. Cl. .................... 514/389; 514/391; 548/311.7; 548/319.5
(58) Field of Search .......................... 548/311.7, 319.5; 514/389

(56) References Cited

U.S. PATENT DOCUMENTS

| | | | |
|---|---|---|---|
| 4,344,949 A | 8/1982 | Hoefle et al. | |
| 4,350,704 A | 9/1982 | Hoefle et al. | |
| 4,374,847 A | 2/1983 | Gruenfeld | |
| 5,389,614 A | 2/1995 | König et al. | |
| 5,397,796 A | 3/1995 | Zoller et al. | |
| 5,424,293 A | 6/1995 | Zoller et al. | |
| 5,554,594 A | 9/1996 | Zoller et al. | |
| 5,658,935 A | 8/1997 | Klingler et al. | |
| 5,686,421 A | 11/1997 | König et al. | |
| 5,939,556 A | 8/1999 | Zoller et al. | |
| 5,981,492 A * | 11/1999 | Zoller et al. | 514/20 |
| 5,998,447 A * | 12/1999 | Stilz et al. | 514/341 |
| 6,034,238 A * | 3/2000 | Wehner et al. | 544/139 |
| 6,331,552 B1 * | 12/2001 | Wehner et al. | 514/341 |
| 2002/0065391 A1 * | 5/2002 | Stilz et al. | 530/331 |

FOREIGN PATENT DOCUMENTS

| | | | |
|---|---|---|---|
| CA | 2220784 | * | 5/1998 |
| CA | 2247551 | * | 3/1999 |
| DE | 235 866 A1 | | 5/1986 |
| DE | 41 26 277 A1 | | 2/1993 |
| DE | 196 47 380 A1 | | 5/1998 |

(List continued on next page.)

OTHER PUBLICATIONS

Steven M. Albelda et al., "Molecular and Cellular Properties of PECAM–1 (endoCAM/CD31): A Novel Vascular Cell–Cell Adhesion Molecule", The Journal of Cell Biology, Sep. 1991, pp. 1059–1068, vol. 114, No. 5, The Rockeffeler University Press.

Carmen Barbadillo et al., "Anti–integrin Immunotherapy in Rheumatoid Arthritis: Protective Effect Of Anti–α4 Antibody In Adjuvant Arthritis", Springer Seminar Immunopathol, Immunopathology, 1995, pp. 427–436, No. 16, Springer–Verlag.

J.M. Bergelson et al., "Do Integrins Use A 'MIDAS Touch' To Grasp An Asp?", Current Biology 1995, pp. 615–617, vol. 5, No. 6.

Raymond J. Bergeron et al., "Total Synthesis of (±)–15–Deoxyspergualin", J. Org. Chem., 1987, pp. 1700–1703, No. 52, American Chemical Society.

R.F. Borne et al., "Conformational Analogues of Antihypertensive Agents Related to Guanethidine", Journal of Medicinal Chemistry, 1997, pp. 771–776, vol. 20, No. 6.

Von Hans Th. Bucherer et al., "Über die Bildung Substituierter Hydantoine aus Aldehyden und Ketonen Synthese von Hydantoinen", Journal für praktische Chemie N.F., 1934, Band 141.

(List continued on next page.)

*Primary Examiner*—Laura L. Stockton
(74) *Attorney, Agent, or Firm*—Heller Ehrman White and McAuliffe

(57) ABSTRACT

The present invention relates to imidazolidine derivatives of the formula I, (I)

in which B, E, W, Y, R, $R^2$, $R^3$, $R^{30}$, e and h have the meanings indicated in the claims. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leukocytes and/or antagonists of the adhesion receptor VLA-4 belonging to the integrins group. They are generally suitable for the therapy or prophylaxis of diseases which are caused by an undesired extent of leukocyte adhesion and/or leukocyte migration or are associated therewith, or in which cell-cell or cell-matrix interactions which are based on interactions of VLA-4 receptors with their ligands play a part. The invention furthermore relates to processes for the preparation of the compounds of the formula I, their use, in particular as pharmaceutical active compounds, and pharmaceutical preparations which contain compounds of the formula I.

13 Claims, No Drawings

FOREIGN PATENT DOCUMENTS

| | | |
|---|---|---|
| DE | 196 47 381 A1 | 5/1998 |
| DE | 196 47 382 A1 | 5/1998 |
| DE | 197 51 251 A1 | 5/1999 |
| EP | 029 488 A1 | 6/1981 |
| EP | 031 741 A1 | 7/1981 |
| EP | 046 953 A2 | 3/1982 |
| EP | 049 605 A1 | 4/1982 |
| EP | 049 658 A1 | 4/1982 |
| EP | 050 800 A1 | 5/1982 |
| EP | 051 020 A1 | 5/1982 |
| EP | 052 870 A1 | 6/1982 |
| EP | 079 022 A2 | 5/1983 |
| EP | 084 164 A2 | 7/1983 |
| EP | 089 637 A2 | 9/1983 |
| EP | 090 341 A2 | 10/1983 |
| EP | 090 362 A2 | 10/1983 |
| EP | 105 102 A1 | 4/1984 |
| EP | 109 020 A2 | 5/1984 |
| EP | 111 873 A1 | 6/1984 |
| EP | 271 865 A2 | 6/1988 |
| EP | 344 682 A2 | 12/1989 |
| EP | 449 079 A2 | 10/1991 |
| EP | 530 505 A2 | 3/1993 |
| EP | 566 919 A1 | 10/1993 |
| EP | 580 008 A2 | 1/1994 |
| EP | 584 694 A1 | 3/1994 |
| EP | 796 855 A1 | 9/1997 |
| EP | 842 943 A2 | 5/1998 |
| EP | 842 944 A2 | 5/1998 |
| EP | 842 945 A2 | 5/1998 |
| EP | 903 353 A1 | 3/1999 |
| EP | 905 139 A2 | 3/1999 |
| EP | 918 059 A1 | 5/1999 |
| WO | WO 93/13798 A1 | 7/1993 |
| WO | WO 93/15764 A1 | 8/1993 |
| WO | WO 93/18057 A1 | 9/1993 |
| WO | WO 94/15958 A2 | 7/1994 |
| WO | WO 94/16094 A2 | 7/1994 |
| WO | WO 94/17828 A2 | 8/1994 |
| WO | WO 94/21607 A1 | 9/1994 |
| WO | WO 95/14008 A1 | 5/1995 |
| WO | WO 95/15973 A1 | 6/1995 |
| WO | WO 95/19790 A1 | 7/1995 |
| WO | WO 96/00581 A1 | 1/1996 |
| WO | WO 96/06108 A2 | 2/1996 |
| WO | WO 96/20216 A1 | 7/1996 |
| WO | WO 96/22966 A1 | 8/1996 |
| WO | WO 96/33976 A1 | 10/1996 |
| WO | WO 97/03094 A1 | 1/1997 |
| WO | WO 98/04247 A1 | 2/1998 |
| WO | WO 98/04913 A1 | 2/1998 |
| WO | WO 98/42656 A1 | 10/1998 |

OTHER PUBLICATIONS

E.E. Büllesbach, "Schutzgruppen in der Peptidsynthese (Teil 2): Mehrfunktionelle Aminosäuren—zur Abspaltung—Perspektiven der Schutzgruppentechnik", Kontakte 1/80 pp. 23–35, year not available.

Hans Bundgaard, "Novel Chemical Approaches in Prodrug Design", Drugs of the Future, 1991, p. 443–458, No. 16(5), Prous Science.

Bruce N. Cronstein et al., "The Adhesion Molecules of Inflammation", Arthritis and Rheumatism, Feb. 1993, pp. 147–157, vol. 36, No. 2.

Nitin K. Damle et al., "Vascular Cell Adhesion Molecule 1 Induces T–Cell Antigen Receptor–Dependent Activation of CD⁺ T Lymphocytes", Proc. Natl. Acad. Sci., Aug. 1991, pp. 6403–6407, vol. 88.

Anna C. H. M. Van Dinther–Janssen et al., "The VLA–4/VCAM–1 Pathway Is Involved In Lymphocyte Adhesion to Endothelium in Rheumatoid Synovium", The Journal of Immunology, Dec. 15, 1991, pp. 4207–4210, vol. 147, No. 12.

Mariano J. Elices et al., "VCAM–1 on Activated Endothelium Interacts With the Leukocyte Integrin VLA–4 at a Site Distinct From the VLA–4/Fibronectin Binding Site", Cell, Feb. 23, 1990, pp. 577–584, vol. 60, Cell Press.

Mariano J. Elices, "The Integrin α4β1 (VLA–4) as a Therapeutic Target", Cell Adhesion and Human Disease, 1995, pp. 79–90.

Mariano J. Elices et al., Expression and Functional Significance of Alternatively Spliced CS1 Fibronectin in Rheumatoid Arthritis Microvasculature, The American Society for Clinical Investigation, Inc., Jan. 1994, pp. 405–416, vol. 93.

M.J. Elices et al., "The Integrin VLA–4 Mediates Leukocyte Recruitment to Skin Iflammatory Sites In Vivo", Clinical and Experimental Rheumatology, 1993, pp. S77–S80, No. 11 (Suppl. 8).

Denise M. Flanagan et al., Studies Directed Toward the Total Synthesis of 14–Membered Cyclopeptide Alkaloids: Synthesis of A Linear Precursor to Nummularine–$F^1$, Synthetic Communications, 1990, pp. 459–467, No. 20(3), Marcel Dekker, Inc.

David Fleisher et al., "Improved Oral Drug Delivery: Solubility Limitations Overcome By the Use of Prodrugs", Advanced Drug Delivery Reviews, 1996, pp. 115–130, No. 19, Elsevier Science B.V.

Carolyn A. Foster, Ph.D., "VCAM–1/α4–Integrin Adhesion Pathway: Therapeutic Target for Allergic Inflammatory Disorders", J. Allergy Clin. Immunol., 1996, pp. S270–S277, vol. 98, No. 67, part 2.

Arnold S. Freedman et al., "Follicular Non–Hodgkin's Lymphoma Cell Adhesion to Normal Germinal Centers and Neoplastic Follicles Involves Very Late Antigen–4 and Vascular Cell Adhesion Molecule–1", Blood, Jan. 1, 1992, pp. 206–212, vol. 79, No. 1, The American Society of Hematology.

Kimitoshi Fukunaga, "Debromination of Vic–Dibromides with Sodium Sulfide in Dimethylformamide", Communications, Nov. 1981, pp. 879–880.

Von Stefan Goldschmidt et al., "Über Peptid–Synthesen I", Eingelaufen am 30, Nov. 1951, pp. 217–231.

L.S. Hafner et al., "Preparation of 2–Imino– and 2–Nitrimino– 1.3–Diazacycloalkanes", Notes, Aug. 1959, pp. 1157–1159.

Richard F. Heck, "Palladium–Catalyzed Vinylation of Organic Halides", pp. 345–390, year not available.

A. Hubbuch, "Schutzgruppen in der Peptidsynthese (Teil 1): Schutzgruppentaktik, Amino– und Carboxyl–Schutzgruppen", Kontakte 3/79, pp. 14–23, year not available.

M. Isobe et al., "Effect of Anti–VCAM–1 and Anti–VLA–4 Monoclonal Antibodies on Cardiac Allograft Survival and Response to Solbule Antigens in Mice", Transplantation Proceedings, Apr. 1994, pp. 867–868, vol. 26, No. 2.

Thomas B. Issekutz et al., "Rat Blood Neutrophils Express Very Late Antigen 4 and it Mediates Migration to Arthritic Joint and Dermal Inflammation", J. Exp. Med., May 1996, pp. 2175–2184, vol. 183, Rockefeller University Press.

G.W. Kabalka et al., "Bromination of Alkenes Using a Mixture of Sodium Bromide and Sodium Perborate", Synthetic Communications, 1998, pp. 925–929, No. 28(5), Marcel Dekker, Inc.

G. Kilger et al., Molecular Analysis of the Physiological and Pathophysiological Role of α4–Integrins, J. Mol. Med, 1995, pp. 347–354, No. 73, Springer–Verlag.

Keekyung Kim et al., "Monosubstituted Guanidines from Primary Amines and Aminoiminomethanesulfonic Acid", Tetranecron Letters, 1988, pp. 3183–3186, vol. 29, No. 26, Pergamon Press plc.

Taco W. Kuijpers, "Patophysiological Aspects of VLA–4 Interactions and Possibilities for Therapeutical Inverventions", Springer Seminars Immunopathology, 1995, pp. 379–389, Springer–Verlag.

Armando Laffón et al., "Upregulated Expression and Function of VLA–4 Fibronectin Receptors on Human Activated T Cells in Rheumatoid Arthritis", J. Clin. Invest., Aug. 1991, pp. 546–552, vol. 88, The American Society for Clinical Investigation, Inc.

Robert W. McMurray, "Seminars in Arthritis and Rheumatism", Seminars in Arthritis and Rheumatism, Feb. 1996, pp. 215–233, vol. 25, No. 4.

Jeanette Morales–Ducret et al., "Vascular Cell Adhesion Molecule–1 Expression in Synovium and on Fibroblast–Like Synoviocytes", The Journal of Immunology, Aug. 15, 1992, pp. 1424–1431, vol. 149, No. 4, The American Association of Immunologists.

Shin'Ichi Nakatsuji et al., "Synthesis and Absorption/Emission Spectroscopic Properties of Bis(phenylethynyl)benzenes and 9,10–Bis(phenylethynyl)anthracenes", J. Chem. Soc. Perkin Trans. 1992, pp. 755–758.

Kevin D. O'Brien et al., "Vascular Cell Adhesion Molecule–1 Is Expressed in Human Coronary Atherosclerotic Plaques", J. Clin. Invest., Aug. 1993, pp. 945–951, vol. 92, The American Society for Clinical Investigation, Inc.

Christian F. Ockenhouse et al., "Human Vascular Endothelial Cell Adhesion Receptors for Plasmodium Falciparum–infected Erythrocytes: Roles for Endothelial Leukocyte Adhesion Molecule 1 and Vascular Cell Adhesion Molecule 1", The Journal of Experimental Medicine, Oct. 1992, pp. 1183–1189, vol. 176.

Laurelee Osborn, "Leukocyte Adhesion to Endothelium in Inflammation", Cell, Jul. 13, 1990, pp. 3–6, vol. 62, Cell Press.

Laurelee Osborn et al., "Direct Expression Cloning of Vascular Cell Adhesion Molecule 1, a Cytokine–Induced Endothelial Protein That Binds to Lymphocytes", Cell, Dec. 22, 1989, pp. 1203–1211, vol. 59, Cell Press.

Antonio A. Postigo et al., "Increased Binding of Synovial T. Lymphocytes from Rheumatoid Arthritis to Endothelial–Leukocyte Adhesion Molecule–1 (ELAM–1) and Vascular Cell Adhesion Molecule–1 (VCAM–1)", J. Clin. Invest., May 1992, pp. 1445–1452, vol. 89, The American Society for Clinical Investigation, Inc.

Risto Renkonen et al., "Expression of Endothelial Adhesion Molecules in Vivo", American Journal of Pathology, Apr. 1992, pp. 763–767, vol. 140, No. 4, American Association of Pathologists.

G. Edgar Rice et al., "An Inducible Endothelial Cell Surface Glycoprotein Mediates Melanoma Adhesion", Science, Dec. 8, 1989, pp. 1303–1306, vol. 246.

Erkki Ruoslahti, "Fibronectin and its Receptors", Ann. Rev. Biochem., 1988, pp. 375–413, No. 57, Annual Reviews Inc.

Muhammad Safadi et al., "Phosphoryloxymethyl Carbamates and Carbonates–Novel Water–Soluble Prodrugs for Amines and Hindered Alcohols", Pharmaceutical Research, 1993, pp. 1350–1355, vol. 10, No. 9, Plenum Publishing Corporation.

Mark G. Saulnier et al., "An Efficient Method for the Synthesis of Guanidino Prodrugs", Bioorganic & Medicinal Chemistry Letters, 1994, pp. 1985–1990, vol. 4, No. 16, Elsevier Science Ltd.

F.L. Scott et al., "Studies in the Pyrazole Series. III. Substituted Guanidines", Pyrazole Series: Substituted Guanidines, Aug. 20, 1953, pp. 4053–4054, vol. 75.

Timothy A. Springer, "Traffic Signals for Lymphocyte Recirculation and Leukocyte Emigration: The Multistep Paradigm", Cell, Jan. 28, 1994, pp. 301–314, vol. 76, Cell Press.

Hans Ulrich Stilz, "From a Peptide Lead to an Orally Active Peptidomimetic Fibrinogen Receptor Antagonist", Lett. Pept. Sci., 1998, pp. 215–221, No. 5(2–3).

Lloyd M. Stoolman, "Adhesion Molecules Controlling Lymphocyte Migration", Cell, Mar. 24, 1989, pp. 907–910, vol. 56, Cell Press.

Tsutomu Takeuchi et al., "Upregulated Expression and Function of Integrin Adhesive Receptors in Systemic Lupus Erythematosus Patients with Vasculitis", J. Clin. Invest., Dec. 1993, pp. 3008–3016, vol. 92, The American Society for Clinical Investigation, Inc.

Caspar Tropp, "Einwirkung von Phosgen auf Polypeptidartige Derivate der p–Amino–benzoesäure. Bildung von 1.3–substituierten Hydantoinen", Eingegangen am 16, Apr. 1928, pp. 1431–1439.

G. Wagner et al., "Synthese von 3–[Amidinophenyl]–alaninen und 3–[Amidinophenyl]–milchsäuren", Pharmazie 29, 1974, pp. 12–15, H. 1.

Von Stefan Weiss et al., "Zur Guanylierung von Aminen mit O–Methyl–isoharnstoff–sulfat" Chemiker–Zeitung 98, 1974, pp. 617–618, Nr. 12.

Von H. Wollweber et al., "2–(Guanidino)–anilide und Verwandte Verbindungen", Arzneim–Forsch, Drug Res. 34(I), 1984, pp. 531–542, Nr. 5.

Xiao–Dong Yang et al., "Inhibition of Insulitis and Prevention of Diabetes in Nonobese Diabetic Mice by Blocking L–selectin and Very Late Antigen 4 Adhesion Receptors", Proc. Natl. Acad. Sci., Nov. 1993, pp. 10494–10498, vol. 90, Immunology.

Ted A. Yednock et al., "Prevention of Experimental Autoimmune Encephalomyelitis by Antibodies Against α4β1 Integrin", Nature, Mar. 5, 1992, pp. 63–66, vol. 356.

Gerd Zettlmeissl et al., "Expression and Characterization of Human CD4: Immunoglobulin Fusion Proteins", DNA and Cell Biology, Nov. 5, 1990, pp. 347–353, vol. 9, Mary Ann Liebert, Inc.

\* cited by examiner

IMIDAZOLIDINE DERIVATIVES, THE PRODUCTION THEREOF, THEIR USE AND PHARMACEUTICAL PREPARATIONS CONTAINING THE SAME

The present invention relates to imidazolidine derivatives of the formula I,

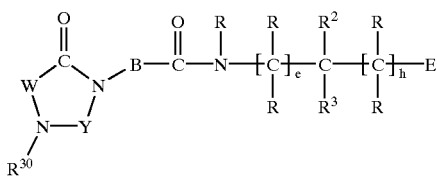

in which B, E, W, Y, R, $R^2$, $R^3$, $R^{30}$, e and h have the meanings indicated below. The compounds of the formula I are valuable pharmaceutical active compounds, which are suitable, for example, for the therapy and prophylaxis of inflammatory disorders, for example of rheumatoid arthritis, or of allergic disorders. The compounds of the formula I are inhibitors of the adhesion and migration of leukocytes and/or antagonists of the adhesion receptor VLA-4 belonging to the integrins group. They are generally suitable for the therapy or prophylaxis of diseases which are caused by an undesired extent of leukocyte adhesion and/or leukocyte migration or are associated therewith, or in which cell-cell or cell-matrix interactions which are based on interactions of VLA-4 receptors with their ligands play a part. The invention furthermore relates to processes for the preparation of the compounds of the formula I, their use, in particular as pharmaceutical active compounds, and pharmaceutical preparations which contain compounds of the formula I.

The integrins are a group of adhesion receptors which play an important part in cell-cell-binding and cell-extracellular matrix-binding processes. They have an αβ-heterodimeric structure and exhibit a wide cellular distribution and a high extent of evolutive conservation. The integrins include, for example, the fibrinogen receptor on platelets, which interacts especially with the RGD sequence of fibrinogen, or the vitronectin receptor on osteoclasts, which interacts especially with the RGD sequence of vitronectin or of osteopontin. The integrins are divided into three major groups, the β2 subfamily with the representatives LFA-1, Mac-1 and p150/95, which are responsible in particular for cell-cell interactions of the immune system, and the subfamilies β1 and β3, whose representatives mainly mediate cell adhesion to components of the extracellular matrix (Ruoslahti, Annu. Rev. Biochem. 1988, 57, 375). The integrins of the β1 subfamily, also called VLA proteins (very late (activation) antigen), include at least six receptors which interact specifically with fibronectin, collagen and/or laminin as ligands. Within the VLA family, the integrin VLA-4 (α4β1) is atypical, insofar as it is mainly restricted to lymphoid and myeloid cells and is responsible in these for cell-cell interactions with a large number of other cells. For example, VLA-4 mediates the interaction of T and B lymphocytes with the heparin II-binding fragment of human plasma fibronectin (FN). The binding of VLA-4 with the heparin II-binding fragment of plasma fibronectin is especially based on an interaction with an LDVP sequence. In contrast to the fibrinogen or vitronectin receptor, VLA-4 is not a typical RGD-binding integrin (Kilger and Holzmann, J. Mol. Meth. 1995, 73, 347).

The leukocytes circulating in the blood normally exhibit only a low affinity for the vascular endothelial cells which line the blood vessels. Cytokines which are released from inflamed tissue cause the activation of endothelial cells and thus the expression of a large number of cell surface antigens. These include, for example, the adhesion molecules ELAM-1 (endothelial cell adhesion molecule-1; also designated as E-selectin), which, inter alia, binds neutrophils, ICAM-1 (intercellular adhesion molecule-1), which interacts with LFA-1 (leukocyte function-associated antigen 1) on leukocytes, and VCAM-1 (vascular cell adhesion molecule-1), which binds various leukocytes, inter alia lymphocytes (Osborn et al., Cell 1989, 59, 1203). VCAM-1, like ICAM-1, is a member of the immunoglobulin gene superfamily. VCAM-1 (first known as INCAM-110) was identified as an adhesion molecule which is induced on endothelial cells by inflammatory cytokines such as TNF and IL-1 and lipopolysaccharides (LPS). Elices et al. (Cell 1990, 60, 577) showed that VLA-4 and VCAM-1 form a receptor-ligand pair which mediates the adhesion of lymphocytes to activated endothelium. The binding of VCAM-1 to VLA-4 does not take place here due to an interaction of the VLA-4 with an RGD sequence; this sequence is not contained in VCAM-1 (Bergelson et al., Current Biology 1995, 5, 615). VLA-4, however, also occurs on other leukocytes, and the adhesion of leukocytes other than lymphocytes is also mediated via the VCAM-1/VLA-4 adhesion mechanism. VLA-4 thus represents an individual example of β1 integrin receptor which, via the ligands VCAM-1 and fibronectin, plays an important part both in cell-cell interactions and in cell-extracellular matrix interactions.

The cytokine-induced adhesion molecules play an important part in the recruitment of leukocytes into extravascular tissue regions. Leukocytes are recruited into inflammatory tissue regions by cell adhesion molecules which are expressed on the surface of endothelial cells and serve as ligands for leukocyte cell surface proteins or protein complexes (receptors) (the terms ligand and receptor can also be used vice versa). Leukocytes from the blood must first adhere to endothelial cells before they can migrate into the synovium. Since VCAM-1 binds to cells which carry the integrin VLA-4 (α4β1), such as eosinophils, T and B lymphocytes, monocytes or also neutrophils, it and the VCAM-1/VLA-4 mechanism have the function of recruiting cells of this type from the blood stream into areas of infection and inflammatory foci (Elices et al., Cell 1990, 60, 577; Osborn, Cell 1990, 62, 3; Issekutz et al., J. Exp. Med. 1996, 183, 2175).

The VCAM-1/VLA-4 adhesion mechanism has been connected with a number of physiological and pathological processes. Apart from cytokine-induced endothelium, VCAM-1 is additionally expressed, inter alia, by the following cells: myoblasts, lymphoid dendritic cells and tissue macrophages, rheumatoid synovium, cytokine-stimulated neural cells, parietal epithelial cells of the Bowman's capsule, the renal tubular epithelium, inflamed tissue during heart and kidney transplant rejection and by intestinal tissue in graft-versus-host disease. VCAM-1 is also found to be expressed on those tissue areas of the arterial endothelium which correspond to early arteriosclerotic plaques of a rabbit model. Additionally, VCAM-1 is expressed on follicular dendritic cells of human lymph nodes and is found on stroma cells of the bone marrow, for example in the mouse. The latter finding points to a function of VCAM-1 in B-cell development. Apart from cells of hematopoietic origin, VLA-4 is also found, for example, on melanoma cell lines, and the VCAM-1/VLA-4 adhesion mechanism is connected with the metastasis of such tumors (Rice et al., Science 1989, 246, 1303).

The main form in which VCAM-1 occurs in vivo on endothelial cells and which is the dominant form in vivo is designated as VCAM-7D and carries seven immunoglobulin domains. The domains 4, 5 and 6 are similar in their amino acid sequences to the domains 1, 2 and 3. The fourth domain is removed in a further form, consisting of six domains, designated here as VCAM-6D, by alternative splicing. VCAM-6D can also bind VLA-4-expressing cells.

Further details on VLA-4, VCAM-1, integrins and adhesion proteins are found, for example, in the articles by Kilger and Holzmann, J. Mol. Meth. 1995, 73, 347; Elices, Cell Adhesion in Human Disease, Wiley, Chichester 1995, p. 79; Kuijpers, Springer Semin. Immunopathol. 1995, 16, 379.

On account of the role of the VCAM-1/VLA-4 mechanism in cell adhesion processes, which are of importance, for example, in infections, inflammations or atherosclerosis, it has been attempted by means of interventions into these adhesion processes to control diseases, in particular, for example, inflammations (Osborn et al., Cell 1989, 59, 1203). A method of doing this is the use of monoclonal antibodies which are directed against VLA-4. Monoclonal antibodies (mAB) of this type, which as VLA-4 antagonists block the interaction between VCAM-1 and VLA-4, are known. Thus, for example, the anti-VLA-4 mAB HP2/1 and HP1/3 inhibit the adhesion of VLA-4-expressing Ramos cells (B-cell-like cells) to human umbilical cord endothelial cells and to VCAM-1-transfected COS cells. The anti-VCAM-1 mAB 4B9 likewise inhibits the adhesion of Ramos cells, Jurkat cells (T-cell-like cells) and HL60 cells (granulocyte-like cells) to COS cells transfected with genetic constructs which cause VCAM-6D and VCAM-7D to be expressed. In vitro data with antibodies which are directed against the α4 subunit of VLA-4 show that the adhesion of lymphocytes to synovial endothelial cells is blocked, an adhesion which plays a part in rheumatoid arthritis (van Dinther-Janssen et al., J. Immunol. 1991, 147, 4207).

In vivo experiments have shown that an experimental autoimmune encepthalomyelitis can be inhibited by anti-α4 mAB. The migration of leukocytes into an inflammatory focus is likewise blocked by a monoclonal antibody against the α4 chain of VLA-4. The influencing of the VLA-4-dependent adhesion mechanism by antibodies was also investigated in an asthma model in order to investigate the role of VLA-4 in the recruitment of leukocytes into inflamed lung tissue (WO-A-93/13798). The administration of anti-VLA-4 antibodies inhibited the late-phase reaction and airway overreaction in allergic sheep.

The VLA-4-dependent cell adhesion mechanism was also investigated in a primate model of inflammatory bowel disease (IBD). In this model, which corresponds to ulcerative colitis in humans, the administration of anti-VLA-4 antibodies resulted in a significant reduction in the acute inflammation.

Moreover, it was possible to show that VLA-4-dependent cell adhesion plays a part in the following clinical conditions including the following chronic inflammatory processes: rheumatoid arthritis (Cronstein and Weismann, Arthritis Rheum. 1993, 36, 147; Elices et al., J. Clin. Invest. 1994, 93, 405), diabetes mellitus (Yang et al., Proc. Natl. Acad. Sci. USA 1993, 90, 10494), systemic lupus erythematosus (Takeuchi et al., J. Clin. Invest. 1993, 92, 3008), allergies of the delayed type (type IV allergy) (Elices et al., Clin. Exp. Rheumatol. 1993, 11, S77), multiple sclerosis (Yednock et al., Nature 1992, 356, 63), malaria (Ockenhouse et al., J. Exp. Med. 1992, 176, 1183), arteriosclerosis (O'Brien et al., J. Clin. Invest. 1993, 92, 945), transplantation (Isobe et al., Transplantation Proceedings 1994, 26, 867–868), various malignancies, for example melanoma (Renkonen et al., Am. J. Pathol. 1992, 140, 763), lymphoma (Freedman et al., Blood 1992, 79, 206) and others (Albelda et al., J. Cell Biol. 1991, 114, 1059).

VLA-4 blocking by suitable antagonists accordingly offers effective therapeutic possibilities, in particular, for example, of treating various inflammatory conditions including asthma and IBD. The particular relevance of VLA-4 antagonists for the treatment of rheumatoid arthritis in this case results, as already stated, from the fact that leukocytes from the blood must first adhere to endothelial cells before they can migrate into the synovium, and that the VLA-4 receptor plays a part in this adhesion. The fact that VCAM-1 is induced by inflammatory agents on endothelial cells (Osborn, Cell 1990, 62, 3; Stoolman, Cell 1989, 56, 907), and the recruitment of various leukocytes into areas of infection and inflammatory foci has already been discussed above. At the same time, T cells adhere to activated endothelium mainly via the LFA-1/ICAM-1 and VLA-4/VCAM-1 adhesion mechanisms (Springer, Cell 1994, 76, 301). On most synovial T cells, the binding capacity of VLA-4 for VCAM-1 is increased in rheumatoid arthritis (Postigo et al., J. Clin. Invest. 1992, 89, 1445). Additionally, an increased adhesion of synovial T cells to fibronectin has been observed (Laffon et al., J. Clin. Invest. 1991, 88, 546; Morales-Ducret et al., J. Immunol. 1992, 149, 1424). VLA-4 is thus highly regulated both in the course of its expression and with respect to its function on T lymphocytes of the rheumatoid synovial membrane. The blocking of the binding of VLA-4 to its physiological ligands VCAM-1 and fibronectin makes possible an effective prevention or alleviation of articular inflammatory processes. This is also confirmed by experiments with the antibody HP2/1 on Lewis rats with adjuvant arthritis, in which an effective prevention of illness has been observed (Barbadillo et al., Springer Semin. Immunopathol. 1995, 16, 427). VLA-4 is thus an important therapeutic target molecule.

The abovementioned VLA-4 antibodies and the use of antibodies as VLA-4 antagonists are described in the Patent Applications WO-A-93/13798, WO-A-93/15764, WO-A-94/16094, WO-A-94/17828 and WO-A-95/19790. In the Patent Applications WO-A-94/15958, WO-A-95/15973, WO-A-96/00581, WO-A-96/06108 and WO-A-96/20216, peptide compounds are described as VLA-4 antagonists. The use of antibodies and peptide compounds as pharmaceuticals, however, is afflicted with disadvantages, for example lack of oral availability, easy degradability or immunogenic action on longer-term use. There is thus a need for VLA-4 antagonists having a favorable profile of properties for use in therapy and prophylaxis.

WO-A-95/14008, WO-A-94/21607 (US-A-5 658 935), WO-A-93/18057, EP-A-449 079, EP-A-530 505 (US-A-5 389 614), EP-A-566 919 (US-A-5 397 796), EP-A-580 008 (US-A-5 424 293) and EP-A-584 694 (US-A-5 554 594) describe substituted 5-membered ring heterocycles which have an amino, amidino or guanidino function at the N-terminal end of the molecule and which exhibit platelet aggregation-inhibiting actions. EP-A-796 855 describes further heterocycles which are inhibitors of bone resorption. In EP-A-842 943 (German Patent Application 19647380.2), EP-A-842 945 (German Patent Application 19647381.0) and EP-A-842 944 (German Patent Application 19647382.9) it is disclosed that certain compounds from these series and certain further compounds surprisingly also inhibit leukocyte adhesion and are VLA-4 antagonists. Inhibitors of leukocyte adhesion and VLA-4 antagonists are also described in EP-A-903 353 (German Patent Application 19741235.1), EP-A-905 139 (German Patent Application 19741873.2) and EP-A-918 059 (German Patent Application 19751251.8). Further investigations showed that the compounds of the present application are also strong inhibitors of leukocyte adhesion and/or VLA-4 antagonists.

The present invention thus relates to compounds of the formula I,

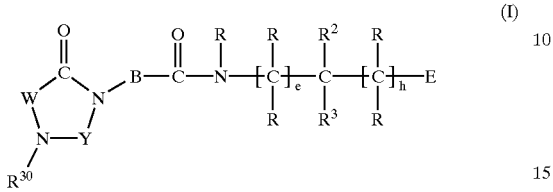

(I)

in which

W is a divalent radical from the group consisting of $R^1$—A-C(R 3), $R^1$—A—C($R^{13}$)=C,

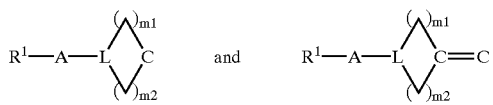 and 

where the ring systems can contain one or two identical or different heteroatoms from the group consisting of N, O and S, can be saturated or mono- or polyunsaturated and can be substituted by 1, 2 or 3 identical or different substituents $R^{13}$ and/or by one or two doubly bonded oxygen atoms and/or sulfur atoms, and where L is C($R^{13}$) or N and where m1 and m2 independently of one another are one of the numbers 0, 1, 2, 3, 4, 5 and 6, but the sum m1+m2 is one of the numbers 1, 2, 3, 4, 5 or 6;

Y is a carbonyl group, thiocarbonyl group or methylene group;

A is a direct bond, one of the divalent radicals ($C_1$–$C_6$)-alkylene, ($C_3$–$C_7$)-cycloalkylene, phenylene, phenylene-($C_1$–$C_6$)-alkyl, phenylene-($C_2$–$C_6$)-alkenyl or a divalent radical of a 5-membered or 6-membered saturated or unsaturated heterocycle, which can contain one or two nitrogen atoms and can be mono- or disubstituted by ($C_1$–$C_6$)-alkyl or doubly bonded oxygen or sulfur, where in the radicals phenylenealkyl and phenylenealkenyl the radical $R^1$ is bonded to the phenylene group;

B is a divalent radical from the group consisting of ($C_1$–$C_6$)-alkylene, ($C_2$–$C_6$)-alkenylene, phenylene, phenylene-($C_1$–$C_3$)-alkyl, ($C_1$–$C_3$)-alkylenephenyl and ($C_1$–$C_3$)-alkylenephenyl-($C_1$–$C_3$)-alkyl, where the ($C_1$–$C_6$)-alkylene radical and the ($C_2$–$C_6$)-alkenylene radical are unsubstituted or substituted by one or more identical or different radicals from the group consisting of ($C_1$–$C_8$)-alkyl, ($C_2$–$C_8$)-alkenyl, ($C_2$–$C_8$)-alkynyl, ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

E is tetrazolyl, ($R^8$O)$_2$P(O), $R^8$OS(O)$_2$, $R^9$NHS(O)$_2$, $R^6$CO, $R^7$CO or $R^{10}$CO;

R is hydrogen, ($C_1$–$C_8$)-alkyl, ($C_3$–$C_{12}$)-cycloalkyl, ($C_3$–$C_{12}$)-cycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl or heteroaryl-($C_1$–$C_8$)-alkyl optionally substituted in the heteroaryl radical, where all radicals R independently of one another can have the meanings indicated and can be identical or different;

$R^1$ is hydrogen, ($C_3$–$C_{12}$)-cycloalkyl, ($C_3$–$C_{12}$)-cycloalkyl-($C_1$–$C_8$)-alkyl, $R^{21}$-(($C_6$–$C_{14}$)-aryl) optionally substituted in the aryl radical, ($R^{21}$-(($C_6$–$C_{14}$)-aryl)-($C_1$–$C_8$)-alkyl optionally substituted in the aryl radical, the radical Het-, Het-($C_1$–$C_8$)-alkyl, one of the radicals X—NH—C(=NH)—$R^{20}$—, $X^1$—NH—$R^{20}$—, $R^{21}$O—$R^{20}$—, $R^{21}$N($R^{21}$)—$R^{20}$—, $R^{21}$C(O)—, $R^{21}$O—C(O)—, $R^{22}$N($R^{21}$)—C(O)—, $R^{22}$C(O)—N($R^{21}$)—, $R^{21}$O—N=, O= and S=, or ($C_1$–$C_{10}$)-alkyl which can optionally be mono- or polysubstituted by fluorine;

X is hydrogen, ($C_1$–$C_6$)-alkyl, ($C_1$–$C_6$)-alkylcarbonyl, ($C_1$–$C_6$)-alkoxycarbonyl, ($C_1$–$C_{10}$)-alkylcarbonyloxy-($C_1$–$C_6$)-alkoxycarbonyl, optionally substituted ($C_6$–$C_{14}$)-arylcarbonyl, optionally substituted ($C_6$–$C_{14}$)-aryloxycarbonyl, ($C_6$–$C_{14}$)-aryl-($C_1$–$C_6$)-alkoxycarbonyl which can also be substituted in the aryl radical, cyano, hydroxyl, ($C_1$–$C_6$)-alkoxy, ($C_6$–$C_{14}$)-aryl-($C_1$–$C_6$)-alkoxy which can also be substituted in the aryl radical, or amino;

$X^1$ has one of the meanings of X or is R'—NH—C(=N—R"), where R' and R" independently of one another have the meanings of X;

$R^2$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical or ($C_3$–$C_8$)-cycloalkyl;

$R^3$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, ($C_3$–$C_8$)-cycloalkyl, ($C_3$–$C_8$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, ($C_2$–$C_8$)-alkenyl, ($C_2$–$C_8$)-alkynyl, $R^{11}$NH, CON(CH$_3$)$R^4$, CONH$R^4$, COO$R^{21}$, COO$R^{15}$, CON(CH$_3$)$R^{15}$ or CONH$R^{15}$;

$R^4$ is hydrogen or ($C_1$–$C_{10}$)-alkyl which is unsubstituted or mono- or polysubstituted by identical or different radicals from the group consisting of hydroxyl, ($C_1$–$C_8$)-alkoxy, $R^5$, optionally substituted ($C_3$–$C_8$)-cycloalkyl, hydroxycarbonyl, aminocarbonyl, mono- or di-(($C_1$–$C_{18}$)-alkyl)aminocarbonyl, ($C_6$–$C_{14}$)-aryl-($C_1$–$C_8$)-alkoxycarbonyl which can also be substituted in the aryl radical, ($C_1$–$C_8$)-alkoxycarbonyl, $R^6$—CO, $R^7$CO, tetrazolyl and trifluoromethyl;

$R^5$ is optionally substituted ($C_6$–$C_{14}$)-aryl, ($C_6$–$C_{14}$)-aryl-($C_1$–$C_8$)-alkyl optionally substituted in the aryl radical, or a radical of an optionally substituted monocyclic or bicyclic, 5-membered to 12-membered heterocyclic ring which can be aromatic, partially saturated or completely saturated and which can contain one, two or three identical or different heteroatoms from the group consisting of nitrogen, oxygen and sulfur;

$R^6$ is the radical of a natural or unnatural amino acid, imino acid, optionally N-$(C_1-C_8)$-alkylated or N-(($C_6-C_{14}$)-aryl-$(C_1-C_8)$-alkylated) azaamino acid which can also be substituted in the aryl radical, or the radical of a dipeptide, bipeptide or tetrapeptide, and their esters and amides, where free functional groups can be protected by protective groups customary in peptide chemistry and where the nitrogen atoms in the amide bonds in the group $R^6$—CO can carry a radical R as a substituent;

$R^7$ is the radical of a 5-membered to 10-membered, saturated monocyclic or polycyclic heterocycle bonded via a nitrogen atom, which can contain one, two, three or four identical or different additional ring heteroatoms from the group consisting of oxygen, nitrogen and sulfur and which can optionally be substituted on carbon atoms and on additional ring nitrogen atoms, where additional ring nitrogen atoms can carry identical or different radicals from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^8$ is hydrogen, $(C_1-C_{10})$-alkyl, optionally substituted $(C_6-C_{14})$-aryl or $(C_6-C_{14})$-aryl-$(C_1-C_8)$-alkyl which can also be substituted in the aryl radical, where the radicals $R^8$ are independent of one another;

$R^9$ is hydrogen, aminocarbonyl, $(C_1-C_{10})$-alkylaminocarbonyl, $(C_3-C_8)$-cycloalkylaminocarbonyl, optionally substituted $(C_6-C_{14})$-arylaminocarbonyl, $(C_1-C_{10})$-alkyl, optionally substituted $(C_6-C_{14})$-aryl or $(C_3-C_8)$-cycloalkyl;

$R^{10}$ is hydroxyl, $(C_1-C_{10})$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy optionally substituted in the aryl radical, amino or mono- or di-(($C_1-C_{10}$)-alkyl)amino;

$R^{11}$ is hydrogen, $R^{12a}$, $R^{12a}$—CO, H—CO, $R^{12a}$—O—CO, $R^{12b}$—CO, $R^{12b}$—CS, $R^{12a}$—$S(O)_2$ or $R^{12b}$—$S(O)_2$;

$R^{12a}$ is $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-(($C_1-C_{10}$)-alkyl)amino or $R^{12a}$—NH;

$R^{13}$ is hydrogen, optionally substituted $(C_6-C_{14})$-aryl, $(C_6-C_{14})$-aryl-$(C_1-C_6)$-alkyl optionally substituted in the aryl radical, $(C_3-C_8)$-cycloalkyl, $(C_3-C_8)$-cycloalkyl-$(C_1-C_6)$-alkyl or $(C_1-C_6)$-alkyl which can optionally be mono- or polysubstituted by fluorine;

$R^{15}$ is $R^{16}$—$(C_1-C_6)$-alkyl or $R^{16}$;

$R^{16}$ is a radical of a 6-membered to 24-membered bicyclic or tricyclic ring which is saturated or partially unsaturated and which can also contain one, two, three or four identical or different heteroatoms from the group consisting of nitrogen, oxygen and sulfur and which can also be substituted by one or more identical or different substituents from the group consisting of $(C_1-C_4)$-alkyl and oxo;

$R^{20}$ is a direct bond or a divalent $(C_1-C_6)$-alkylene radical;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, the radical Het- or Het-$(C_1-C_8)$-alkyl, where alkyl radicals can be mono- or polysubstituted by fluorine and the radicals $R^{21}$ are independent of one another if they occur more than once and can be identical or different;

$R^{22}$ is $R^{21}$—, $R^{21}$—O—, $R^{21}N(R^{21})$—, $R^{21}C(O)$—, $R^{21}O$—C(O)—, $R^{21}N(R^{21})$—C(O)—, $R^{21}N(R^{21})$—C(=N($R^{21}$))— or $R^{21}C(O)$—N($R^{21}$)—;

$R^{30}$ is one of the radicals $R^{23}$—$(C(R)(R))_m$—$R^{31}$—, $R^{32}$—CR=CR—$R^{31}$—, $R^{32}$—C≡C—$R^{31}$—, $R^{32}$—O—$R^{31}$— and $R^{32}$—S—$R^{31}$—, where the radicals R can independently of one another have the meanings indicated and can be identical or different, and m is 1, 2 or 3;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical or $(C_1-C_8)$-alkyl which can optionally be substituted by 1 to 8 fluorine atoms;

$R^{33}$ is a direct bond or a divalent $(C_1-C_6)$-alkylene radical;

$R^{34}$ is a divalent radical from the group consisting of $(C_3-C_{12})$-cycloalkylene, $(C_6-C_{12})$-bicycloalkylene, $(C_6-C_{12})$-tricycloalkylene, optionally substituted $(C_6-C_{14})$-arylene and optionally substituted heteroarylene;

$R^{35}$ is a direct bond or a divalent $(C_1-C_8)$-alkylene radical;

$R^{36}$ is a direct bond, the group —CO— or the group —$S(O)_n$—;

Het is a radical of a monocyclic or polycyclic, 4-membered to 14-membered, aromatic or nonaromatic ring, which contains 1, 2, 3 or 4 identical or different heteroatoms from the group consisting of N, O and S as ring members and can optionally be substituted by one or more, identical or different substituents;

e and h independently of one another are 0 or 1 and can be identical or different;

n is 1 or 2;

in all their stereoisomeric forms and mixtures thereof in all ratios, and their physiologically tolerable salts.

Radicals which can occur a number of times in the compounds of the formula I can in all cases independently of one another have the meanings indicated and be identical or different.

Alkyl radicals can be straight-chain or branched. This also applies if they carry substituents or occur as substituents in other radicals, for example in alkoxy radicals, alkoxycarbonyl radicals or arylalkyl radicals. Divalent radicals derived from alkyl radicals, that is alkylene radicals (=alkanediyl radicals), can likewise be straight-chain or branched. Examples of suitable alkyl radicals are methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, isopropyl, isobutyl, isopentyl, isohexyl, 3-methylpentyl, neopentyl, neohexyl, 2,3,5-trimethylhexyl, sec-butyl, tert-butyl, tert-pentyl. Preferred alkyl radicals are methyl, ethyl, n-propyl, isopropyl, n-butyl, isobutyl, sec-butyl, tert-butyl, n-pentyl, isopentyl, n-hexyl and isohexyl. Examples of alkylene radicals are the divalent radicals corresponding to the abovementioned monovalent radicals, for example methylene, ethylene, trimethylene, tetramethylene, pentamethylene, hexamethylene, methylene or ethylene substituted by alkyl radicals, for example methylene which is substituted by a methyl group, an ethyl group, an n-propyl group, an isopropyl group, an n-butyl group, an isobutyl group, a tert-butyl group, an n-pentyl group, an isopentyl group or an n-hexyl group, or, for example, ethylene which can be substituted either on one carbon atom or on the other carbon atom or also on both carbon atoms.

Alkenyl radicals and alkenylene radicals (=alkenediyl radicals) as well as alkynyl radicals can also be straight-chain or branched. Examples of alkenyl radicals are vinyl, 1-propenyl, allyl, butenyl, 2-methyl-1-propenyl, 2-methyl-2-propenyl, 3-methyl-2-butenyl, examples of alkenylene radicals are vinylene, propenylene, butenylene and examples of alkynyl radicals are ethynyl, 1-propynyl, propargyl.

Cycloalkyl radicals are, in particular, cyclopropyl, cyclobutyl, cyclopentyl, cyclohexyl, cycloheptyl, cyclooctyl, cyclononyl, cyclodecyl, cycloundecyl and cyclododecyl, which, however, can also be substituted, for example, by $(C_1–C_4)$-alkyl. Examples of substituted cycloalkyl radicals which may be mentioned are 4-methylcyclohexyl and 2,3-dimethylcyclopentyl. The same applies to divalent cycloalkylene radicals (=cycloalkanediyl radicals).

Bicycloalkyl radicals, tricycloalkyl radicals and the 6-membered to 24-membered bicyclic and tricyclic radicals representing $R^{16}$ are formally obtained by abstraction of a hydrogen atom from bicycles or tricycles. The basic bicycles and tricycles can contain only carbon atoms as ring members, they can thus be bicycloalkanes or tricycloalkanes, but in the case of the radicals representing $R^{16}$ they can also contain one to four identical or different heteroatoms from the group consisting of nitrogen, oxygen and sulfur, they can thus be aza-, oxa- and thiabicyclo- and -tricycloalkanes. If heteroatoms are contained, preferably one or two heteroatoms, in particular nitrogen atoms or oxygen atoms, are contained. The heteroatoms can occupy any desired positions in the bicyclic or tricyclic structure; they can be located in the bridges or, in the case of nitrogen atoms, also on the bridgeheads. Both the bicycloalkanes and tricycloalkanes and their heteroanalogs can be completely saturated or can contain one or more double bonds. They preferably contain one or two double bonds or are, in particular, completely saturated. Both the bicycloalkanes and tricycloalkanes as well as the heteroanalogs and both the saturated and the unsaturated representatives can be unsubstituted or can be substituted in any desired suitable positions by one or more oxo groups and/or one or more identical or different $(C_1–C_4)$-alkyl groups, for example methyl groups or isopropyl groups, preferably methyl groups. The free bond of the bicyclic or tricyclic radical can be located in any desired position of the molecule, the radical can thus be bonded via a bridgehead atom or an atom in a bridge. The free bond can also be located in any desired stereochemical position, for example in an exo position or an endo position.

Examples of parent structures of bicyclic ring systems, from which a bicyclic radical can be derived, are norbornane (=bicyclo[2.2.1]heptane), bicyclo[2.2.2]octane and bicyclo[3.2.1]octane. Examples of systems which contain heteroatoms or which are unsaturated or substituted are 7-azabicyclo[2.2.1]heptane, bicyclo[2.2.2]oct-5-ene and camphor (=1,7,7-trimethyl-2-oxobicyclo[2.2.1]heptane).

Examples of systems from which a tricyclic radical can be derived are twistane(=tricyclo[$4.4.0.0^{3,8}$]decane), adamantane (=tricyclo[$3.3.1.1^{3,7}$]decane), noradamantane (=tricyclo[$3.3.1.0^{3,7}$]nonane), tricyclo[$2.2.1.0^{2,6}$]heptane, tricyclo[$5.3.2.0^{4,9}$]dodecane, tricyclo[$5.4.0.0^{2,9}$]undecane or tricyclo[$5.5.1.0^{3,11}$]tridecane.

Preferably, bicyclic or tricyclic radicals are derived from bridged bicycles or tricycles, i.e. from systems in which rings have two or more than two atoms in common. Additionally preferred, if not stated otherwise, are also bicyclic or tricyclic radicals having 6 to 18 ring members, particularly preferably those having 6 to 14 ring members, very particularly preferably those having 7 to 12 ring members.

Specifically particularly preferred bicyclic and tricyclic radicals which, for example, can be a bicycloalkyl group or a tricycloalkyl group are the 2-norbornyl radical, both that having the free bond in the exo position and that having the free bond in the endo position, the 2-bicyclo[3.2.1]octyl radical, the adamantyl radical, both the 1-adamantyl radical and the 2-adamantyl radical, the homoadamantyl radical and the noradamantyl radical, for example the 3-noradamantyl radical. Moreover preferred are the 1-adamantyl and the 2-adamantyl radicals.

The same applies to the divalent bicycloalkylene radicals (=bicycloalkanediyl radicals) and tricycloalkylene radicals (=tricycloalkanediyl radicals).

$(C_6–C_{14})$-Aryl groups are, for example, phenyl, naphthyl, for example 1-naphthyl and 2-naphthyl, biphenylyl, for example 2-biphenylyl, 3-biphenylyl and 4-biphenylyl, anthryl or fluorenyl, $(C_6–C_{10})$-aryl groups are, for example, 1-naphthyl, 2-naphthyl and phenyl. Biphenyl radicals, naphthyl radicals and in particular phenyl radicals are preferred aryl radicals. Aryl radicals, in particular phenyl radicals, can be unsubstituted or substituted one or more times, preferably one, two or three times, by identical or different radicals. Substituted radicals are preferably substituted by radicals from the group consisting of $(C_1–C_8)$-alkyl, in particular $(C_1–C_4)$-alkyl, $(C_1–C_8)$-alkoxy, in particular $(C_1–C_4)$-alkoxy, halogen, nitro, amino, trifluoromethyl, hydroxyl, hydroxy-$(C_1–C_4)$-alkyl such as, for example, hydroxymethyl or 1-hydroxyethyl or 2-hydroxyethyl, methylenedioxy, ethylenedioxy, formyl, acetyl, cyano, hydroxycarbonyl, aminocarbonyl, $(C_1–C_4)$-alkoxycarbonyl, phenyl, phenoxy, benzyl, benzyloxy, tetrazolyl. The same applies, for example to radicals such as arylalkyl or arylcarbonyl. Arylalkyl radicals are, in particular, benzyl and 1- and 2-naphthylmethyl, 2-, 3- and 4-biphenylylmethyl and 9-fluorenylmethyl, which can also be substituted. Substituted arylalkyl radicals are, for example, benzyl radicals and naphthylmethyl radicals substituted in the aryl moiety by one or more $(C_1–C_8)$-alkyl radicals, in particular $(C_1–C_4)$-alkyl radicals, for example 2-, 3- and 4-methylbenzyl, 4-isobutylbenzyl, 4-tert-butylbenzyl, 4-octylbenzyl, 3,5-dimethylbenzyl, pentamethylbenzyl, 2-, 3-, 4-, 5-, 6-, 7- and 8-methyl-1-naphthylmethyl, 1-, 3-, 4-, 5-, 6-, 7- and 8-methyl-2-naphthylmethyl; benzyl radicals and naphthylmethyl radicals substituted in the aryl moiety by one or more $(C_1–C_8)$-alkoxy radicals, in particular $(C_1–C_4)$-alkoxy radicals, for example 4-methoxybenzyl, 4-neopentyloxybenzyl, 3,5-dimethoxybenzyl, 3,4- methylenedioxybenzyl, 2,3,4-trimethoxybenzyl; nitrobenzyl radicals, for example 2-, 3- and 4-nitrobenzyl; halobenzyl radicals, for example 2-, 3- and 4-chloro- and 2-, 3-, and 4-fluorobenzyl; 3,4-dichlorobenzyl, pentafluorobenzyl; trifluoromethyl-benzyl radicals, for example 3- and 4-trifluoromethylbenzyl or 3,5-bis(trifluoromethyl)-benzyl. Substituted arylalkyl radicals, however, can also have different substituents. Usually in the compounds of the formula I not more than two nitro groups can be present in the molecule In monosubstituted phenyl radicals, the substituent can be located in the 2-position, the 3-position or the 4-position. Disubstituted phenyl can be substituted in the 2,3-position, 2,4-position, 2,5-position, 2,6-position, 3,4-position or 3,5-position. In trisubstituted phenyl radicals, the substituents can be present in the 2,3,4-position, 2,3,5-position, 2,4,5-position, 2,4,6-position, 2,3,6-position or 3,4,5-position.

The explanations relating to aryl radicals apply correspondingly to divalent arylene radicals, for example to phenylene radicals, which can be present, for example, as 1,4-phenylene or as 1,3-phenylene.

Phenylene-$(C_1-C_6)$-alkyl is in particular phenylenemethyl (—$C_6H_4$—$CH_2$—) and phenyleneethyl, $(C_1-C_6)$-alkylenephenyl is in particular methylenephenyl (—$CH_2$—$C_6H_4$—). Phenylene-$(C_2-C_6)$-alkenyl is in particular phenyleneethenyl and phenylenepropenyl.

Heteroaryl is a radical of a monocyclic or polycyclic aromatic system having 5 to 14 ring members, which contains 1, 2, 3, 4 or 5 heteroatoms as ring members. Examples of heteroatoms are N, O and S. If several heteroatoms are contained, these can be identical or different. Heteroaryl radicals can also be unsubstituted or substituted one or more times, preferably one, two or three times, by identical or different radicals from the group consisting of $(C_1-C_8)$-alkyl, in particular $(C_1-C_4)$-alkyl, $(C_1-C_8)$-alkoxy, in particular $(C_1-C_4)$-alkoxy, halogen, nitro, amino, trifluoromethyl, hydroxyl, hydroxy-$(C_1-C_4)$-alkyl such as, for example, hydroxymethyl or 1-hydroxyethyl or 2-hydroxyethyl, methylenedioxy, ethylenedioxy, formyl, acetyl, cyano, hydroxycarbonyl, aminocarbonyl, $(C_1-C_4)$-alkoxycarbonyl, phenyl, phenoxy, benzyl, benzyloxy and tetrazolyl. Preferably, heteroaryl is a monocyclic or bicyclic aromatic radical which contains 1, 2, 3 or 4, in particular 1, 2 or 3, identical or different heteroatoms from the group consisting of N, C and S and which can be substituted by 1, 2, 3 or 4, in particular 1 to 3, identical or different substituents from the group consisting of $(C_1-C_6)$-alkyl, $(C_1-C_6)$-alkoxy, fluorine, chlorine, nitro, amino, trifluoromethyl, hydroxyl, hydroxy-$(C_1-C_4)$-alkyl, $(C_1-C_4)$-alkoxycarbonyl, phenyl, phenoxy, benzyloxy and benzyl. Particularly preferably, heteroaryl is a monocyclic or bicyclic aromatic radical having 5 to 10 ring members, in particular a 5-membered to 6-membered monocyclic aromatic radical which contains 1, 2 or 3, in particular 1 or 2, identical or different heteroatoms from the group consisting of N, O and S and can be substituted by 1 or 2 identical or different substituents from the group consisting of $(C_1-C_4)$-alkyl, $(C_1-C_4)$-alkoxy, phenyl, phenoxy, benzyloxy and benzyl.

Heterocycles which are monocyclic or bicyclic 5-membered to 12-membered heterocyclic rings can be aromatic or partially or completely saturated. They can be unsubstituted or substituted on one or more carbon atoms or on one or more nitrogen atoms by identical or different substituents, such as is indicated for the radical heteroaryl. In particular, the heterocyclic ring can be substituted one or more times, for example one, two, three or four times, on carbon atoms by identical or different radicals from the group consisting of $(C_1-C_8)$-alkyl, for example $(C_1-C_4)$-alkyl, $(C_1-C_8)$-alkoxy, for example $(C_1-C_4)$-alkoxy such as methoxy, phenyl-$(C_1-C_4)$-alkoxy, for example benzyloxy, hydroxyl, oxo, halogen, nitro, amino or trifluoromethyl, and/or ring nitrogen atoms in heterocyclic rings—and in heteroaryl radicals—can be substituted by $(C_1-C_8)$-alkyl, for example $(C_1-C_4)$-alkyl such as methyl or ethyl, by optionally substituted phenyl or phenyl-$(C_1-C_4)$-alkyl, for example benzyl.

Het comprises, on the one hand, aromatic heterocycles and thus also the groups representing heteroaryl, if these come within the definition of Het with respect to the number of ring members and heteroatoms. Het, however, additionally also comprises nonaromatic heterocycles, which are completely saturated or which contain one or more double bonds in the ring system. Het can be substituted on nitrogen atoms and/or carbon atoms by one or more, for example 1, 2, 3 or 4, identical or different substituents, for example by $(C_1-C_8)$-alkyl, in particular $(C_1-C_4)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, heteroaryl, heteroaryl-$(C_1-C_8)$-alkyl, $(C_1-C_8)$-alkoxy, in particular $(C_1-C_4)$-alkoxy, optionally substituted phenoxy, benzyloxy, halogen, nitro, amino, $(C_1-C_8)$-alkylamino, di-$((C_1-C_8)$-alkyl)amino, trifluoromethyl, hydroxyl, methylenedioxy, ethylenedioxy, cyano, hydroxycarbonyl, aminocarbonyl, $(C_1-C_4)$-alkoxycarbonyl and generally by ester groups, acyl groups, oxo, thioxo, where alkyl radicals can be monosubstituted or polysubstituted by fluorine.

Examples of parent structures of heterocycles on which a heteroaryl radical, the radical Het, the radical of a monocyclic or bicyclic 5-membered to 12-membered heterocyclic ring, the divalent radical of a 5-membered or 6-membered heterocycle, the heterocyclic radical representing $R^7$ or a heterocyclic radical representing $R^{16}$ can be based are, if, in the individual case, they come within the respective definition, pyrrole, furan, thiophenei imidazole, pyrazole, oxazole, isoxazole, thiazole, isothiazole, tetrazole, pyridine, pyrazine, pyrimidine, oxazine, indole, isoindole, indazole, phthalazine, quinoline, isoquinoline, quinoxaline, quinazoline, cinnoline, β-carboline and benzo-fused, cyclopenta-, cyclohexa- or cyclohepta-fused derivatives of these heterocycles.

Nitrogen heterocycles can also be present as N-oxides or as quaternary salts.

Radicals which can be heteroaryl or the radical of a monocyclic or bicyclic 5-membered to 12-membered heterocyclic ring are, for example, 2- or 3-pyrrolyl, phenylpyrrolyl, for example 4- or 5-phenyl-2-pyrrolyl, 2- or 3-furyl, 2- or 3-thienyl, 4-imidazolyl, methylimidazolyl, for example 1-methyl-2-, -4- or -5-imidazolyl, 1,3-thiazol-2-yl, 2-pyridyl, 3-pyridyl, 4-pyridyl, 2-, 3- or 4-pyridyl-N-oxide, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta[b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or 2-benzothiazolyl or, as radicals of partially saturated or completely saturated heterocyclic rings, for example also dihydropyridinyl, pyrrolidinyl, for example 2-or 3-(N-methylpyrrolidinyl), piperazinyl, morpholinyl, thiomorpholinyl, tetrahydrothienyl, benzodioxolanyl.

The explanations for heteroaryl radicals apply correspondingly to the divalent heteroarylene radicals.

Heterocyclic radicals representing the radical $R^7$ can be unsubstituted on the carbon atoms and/or on additional ring nitrogen atoms or substituted one or more times, for example one, two, three, four or five times, by identical or different substituents. Carbon atoms can be substituted, for example, by ($C_1$–$C_8$)-alkyl, in particular ($C_1$–$C_4$)-alkyl, ($C_1$–$C_8$)-alkoxy, in particular ($C_1$–$C_4$)-alkoxy, halogen, nitro, amino, trifluoromethyl, hydroxyl, oxo, cyano, hydroxycarbonyl, aminocarbonyl, ($C_1$–$C_4$)-alkoxycarbonyl, phenyl, phenoxy, benzyl, benzyloxy, tetrazolyl, in particular by ($C_1$–$C_4$)-alkyl, for example methyl, ethyl or tert-butyl, ($C_1$–$C_4$)-alkoxy, for example methoxy, hydroxyl, oxo, phenyl, phenoxy, benzyl, benzyloxy. Sulfur atoms can be oxidized to the sulfoxide or to the sulfone. Examples of the radical Het are 1-pyrrolidinyl, 1-piperidinyl, 1-piperazinyl, 4-substituted 1-piperazinyl, 4-morpholinyl, 4-thiomorpholinyl, 1-oxo-4-thiomorpholinyl, 1,1-dioxo-4-thiomorpholinyl, perhydroazepin-1-yl, 2,6-dimethyl-1-piperidinyl, 3,3-dimethyl-4-morpholinyl, 4-isopropyl-2,2,6,6-tetramethyl-1-piperazinyl, 4-acetyl-1-piperazinyl, 4-ethoxycarbonyl-1-piperazinyl.

Halogen is fluorine, chlorine, bromine or iodine, in particular fluorine or chlorine.

The substituent on a substituted alkylene radical or alkenylene radical representing B can on the one hand contain a cycle when it is a substituent from the group consisting of ($C_3$–$C_{10}$)-cycloalkyl, ($C_3$–$C_{10}$)-cycloalkyl-($C_1$–$C_6$)-alkyl, optionally substituted ($C_6$–$C_{14}$)-aryl, ($C_6$–$C_{14}$)-aryl-($C_1$–$C_6$)-alkyl optionally substituted in the aryl radical, optionally substituted heteroaryl and heteroaryl-($C_1$–$C_6$) optionally substituted in the heteroaryl radical, and on the other hand it can be acyclic if it is a substituent from the group consisting of ($C_1$–$C_8$)-alkyl, ($C_2$–$C_8$)-alkenyl and ($C_2$–$C_8$)-alkynyl. The acyclic substituents can contain 2, 3, 4, 5, 6, 7 or 8 carbon atoms or, in the case of the saturated alkyl radical, also 1 carbon atom. In the case of the alkenyl radicals and alkynyl radicals, the double bond or triple bond can be located in any desired position and in the case of the double bond can have the cis configuration or trans configuration. As explained above, these alkyl radicals, alkenyl radicals and alkynyl radicals can be straight-chain or branched.

As examples of substituents which the ($C_1$–$C_6$)-alkylene radical or ($C_2$–$C_6$)-alkenylene radical representing B can carry, in particular the following may be mentioned: methyl, ethyl, n-propyl, n-butyl, n-pentyl, n-hexyl, n-heptyl, n-octyl, isopropyl, isobutyl, isopentyl, isohexyl, sec-butyl, tert-butyl, tert-pentyl, neopentyl, neohexyl, 3-methylpentyl, 2-ethylbutyl, vinyl, allyl, 1-propenyl, 2-butenyl, 3-butenyl, 3-methyl-2-butenyl, ethynyl, 1-propynyl, 2-propynyl, 6-hexynyl, phenyl, benzyl, 1-phenylethyl, 2-phenylethyl, 3-phenylpropyl, 4-biphenylylmethyl, cyclopropyl, cyclopropylmethyl, cyclopentyl, cyclohexyl, cyclohexylmethyl, 2-cyclohexylethyl, 3-cyclooctylpropyl, 2-pyridyl, 3-pyridyl, 4-pyridyl, 4-pyridylmethyl, 2-(4-pyridyl)ethyl, 2-furylmethyl, 2-thienylmethyl, 3-thienylmethyl or 2-(3-indolyl)ethyl.

The radical of an amino acid, imino acid or azaamino acid or of a dipeptide, tripeptide or tetrapeptide is obtained from the corresponding amino acid, imino acid or azaamino acid or the dipeptide, tripeptide or tetrapeptide as customary in peptide chemistry by formally removing a hydrogen atom from the N-terminal amino group or from the imino group. This group is then linked in peptide fashion through an amide bond to the CO group in the group $R^6$—CO via the free bond on the amino group or the imino group resulting in this way.

The natural and unnatural amino acids can be present in all stereochemical forms, for example in the D form, the L form or in the form of a mixture of stereoisomers, for example in the form of a racemate. Preferred amino acids are β-amino acids and α-amino acids; α-amino acids are particularly preferred. Suitable amino acids which may be mentioned, for example, are (cf. Houben-Weyl, Methoden der organischen Chemie [Methods of Organic Chemistry], Volume 15/1 and 15/2, Georg Thieme Verlag, Stuttgart, 1974): Aad, Abu, γAbu, ABz, 2ABz, εAca, Ach, Acp, Adpd, Ahb, Aib, βAib, Ala, β-Ala, ΔAla, Alg, All, Ama, Amt, Ape, Apm, Apr, Arg, Asn, Asp, Asu, Aze, Azi, Bai, Bph, Can, Cit, Cys, (CyS)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hphe, hpro, hser, hThr, hTrp, hTyr, Hyl, Hyp, 3Hyp, Ile, Ise, Iva, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sem, Ser, Thi, βThi, Thr, Thy, Thx, Tia, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylamino-acetic acid, 2-(p-chlorophenyl)-aminoacetic acid.

If $R^6$ is the radical of a natural or unnatural α-amino acid, this radical can be represented, for example, by the formula —N(R)—CH(SC)—CO—AG— in which CO—AG is the acid group of the amino acid or a derivative thereof, for example an ester group, an amide group or an amide group which contains a peptide radical, and SC is the side chain of the α-amino acid, i.e., for example, one of the substituents which are contained in the α-position of the above-listed α-amino acids. Examples of side chains are alkyl radicals, for example the methyl group in alanine or the isopropyl group in valine, the benzyl radical in phenylalanine, the phenyl radical in phenylglycine, the 4-aminobutyl radical in lysine or the hydroxycarbonylmethyl group in aspartic acid. Apart from by their chemical structure, such side chains and thus the amino acids can also be grouped, for example, on the basis of their physicochemical properties, for example lipophilic side chains can be differentiated from hydrophilic side chains which contain polar groups. Examples of lipophilic side chains which can be contained in amino acids representing $R^6$ are alkyl radicals, arylalkyl radicals or aryl radicals.

The same applies to amino acids which are part of a radical of a dipeptide, tripeptide or tetrapeptide representing R Azaamino acids are natural or unnatural amino acids in which a CH unit is replaced by a nitrogen atom, for example in α-amino acids the central structural unit

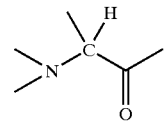

is replaced by

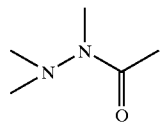

Suitable radicals of imino acids are, in particular, radicals of heterocycles from the following group: pyrrolidine-2- carboxylic acid; piperidine-2-carboxylic acid; 1,2,3,4-tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro-[4.4]nonane-3-carboxylic acid; 2-azaspiro[4.5]decane-3-carboxylic acid; spiro(bicyclo[2.2.1]heptane)-2,3-pyrrolidine-5-carboxylic acid; spiro(bicyclo[2.2.2]octane)-2,3-pyrrolidine-5-carboxylic acid; 2-azatricyclo[4.3.0.1$^{6,9}$]decane-3-carboxylic acid; decahydrocyclohepta[b]pyrrole-2-carboxylic acid; decahydrocycloocta[c]pyrrole-2-carboxylic acid; octahydrocyclopenta[c]pyrrole-2-carboxylic acid; octahydroisoindole-1-carboxylic acid; 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid, hydroxypyrrolidine-2-carboxylic acid, all of which can optionally be substituted (see following formulae):

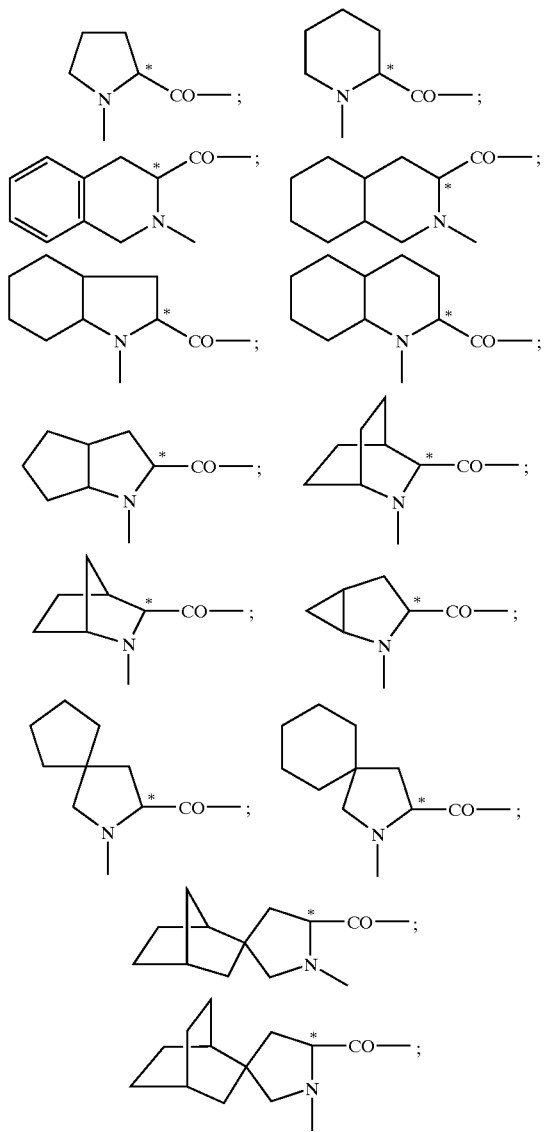

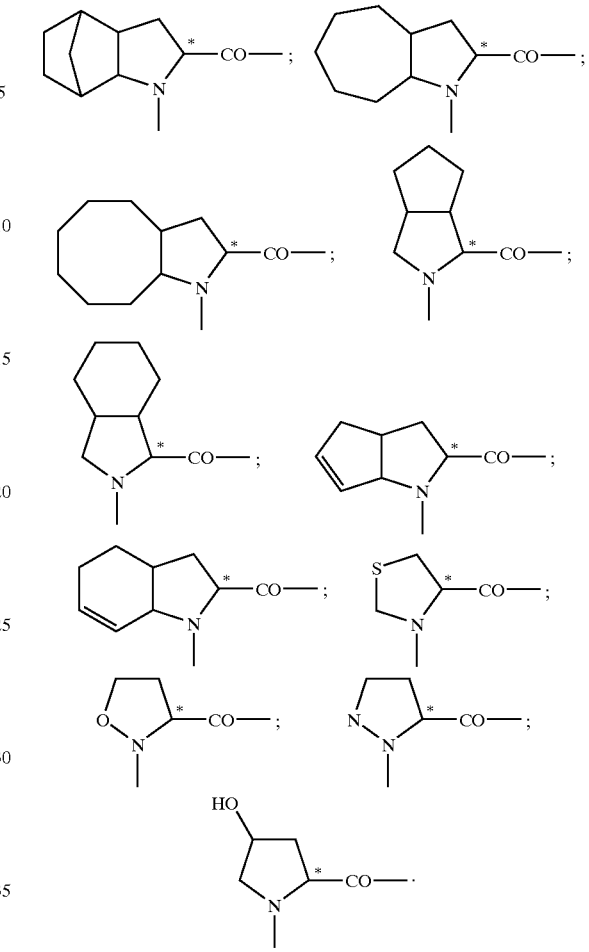

The heterocycles on which the radicals mentioned above are based are disclosed, for example, in US-A-4,344,949; US-A 4,374,847; US-A 4,350,704; EP-A 29,488; EP-A 31,741; EP-A 46,953; EP-A 49,605; EP-A 49,658; EP-A 50,800; EP-A 51,020; EP-A 52,870; EP-A 79,022; EP-A 84,164; EP-A 89,637; EP-A 90,341; EP-A 90,362; EP-A 105,102; EP-A 109,020; EP-A 111,873; EP-A 271,865 and EP-A 344,682.

Dipeptides, tripeptides and tetrapeptides can contain natural or unnatural amino acids, imino acids and azaamino acids as structural units. In addition, the natural or unnatural amino acids, imino acids, azaamino acids, dipeptides, tripeptides and tetrapeptides can also be present in the form of derivatives of the carboxylic acid group, for example as esters or amides, such as, for example, as methyl esters, ethyl esters, n-propyl esters, isopropyl esters, isobutyl esters, tert-butyl esters, benzyl esters, unsubstituted amide, methylamide, ethylamide, semicarbazide or ω-amino-($C_2$-$C_8$)-alkylamide.

Functional groups in the radicals of amino acids, imino acids, azaamino acids and dipeptides, tripeptides and tetrapeptides as well as in other parts of the compounds of the formula I can be present in protected form. Suitable protective groups such as, for example, urethane protective groups, carboxyl protective groups and side-chain protective groups are described in Hubbuch, Kontakte (Merck) 1979, No. 3, pages 14 to 23, and in Btillesbach, Kontakte (Merck) 1980, No. 1, pages 23 to 35. The following may be mentioned in particular: Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert-butyl, OBzl, ONbzl, OMbzl, Bzl, Mob, Pic, Trt.

Physiologically tolerable salts of the compounds of the formula I are in particular pharmaceutically utilizable or nontoxic salts. Such salts of compounds of the formula I which contain acidic groups, for example carboxylic acid groups, are, for example, alkali metal salts or alkaline earth metal salts, such as, for example, sodium salts, potassium salts, magnesium salts, and calcium salts, as well as salts with physiologically tolerable quaternary ammonium ions and acid addition salts with ammonia and physiologically tolerable organic amines such as, for example, triethylamine, ethanolamine, tris(2-hydroxyethyl)amine, α,α,α-tris(hydroxymethyl)methylamine or amino acids, in particular basic amino acids.

Compounds of the formula I which contain basic groups, for example an amino group, amidino group or guanidino group, form salts with inorganic acids, such as, for example, hydrochloric acid, sulfuric acid or phosphoric acid, and with organic carboxylic acids or sulfonic acids, such as, for example, acetic acid, citric acid, benzoic acid, maleic acid, fumaric acid, tartaric acid, methanesulfonic acid or p-toluenesulfonic acid. Compounds which contain both acidic and basic groups can also be present in the form of internal salts or betaines which are likewise included by the present invention.

Salts can be obtained from the compounds of the formula I according to customary procedures known to the person skilled in the art, for example by combining with an organic or inorganic acid or base in a solvent or dispersant, or alternatively from other salts by anion exchange or cation exchange.

The compounds of the formula I can be present in stereoisomeric forms. If the compounds of the formula I contain one or more centers of asymmetry, these can independently of one another have the S configuration or the R configuration. The invention includes all possible stereoisomers of the compounds of the formula I, for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention also relates to diastereomers in pure form and in the form of mixtures of two or more diastereomers in all ratios. In the presence of a cis/trans isomerism, for example on double bonds, the invention relates to both the cis form and the trans form and mixtures of these forms in all ratios. Individual stereoisomers can be prepared, if desired, by use of stereochemically homogeneous starting substances in the synthesis, or by stereoselective synthesis, or by separation of a mixture according to customary methods, for example by chromatography or crystallization, in the case of enantiomers for example by chromatography on chiral phases. If appropriate, derivatization can be carried out before separation of stereoisomers. A stereoisomer mixture can be separated at the stage of the compounds of the formula I or at the stage of a starting substance or of an intermediate in the course of the synthesis.

The compounds of the formula I according to the invention can moreover contain mobile hydrogen atoms, i.e. be present in various tautomeric forms. The present invention also relates to all these tautomers. The present invention furthermore includes solvates of compounds of the formula I, for example hydrates and adducts with alcohols, and derivatives of compounds of the formula I, for example esters, prodrugs and other physiologically tolerable derivatives, as well as active metabolites of compounds of the formula I. The invention relates in particular to prodrugs of the compounds of the formula I which are converted into compounds of the formula I under physiological conditions. Suitable prodrugs for the compounds of the formula I, i.e. chemically modified derivatives of the compounds of the formula I having properties improved in a desired manner, are known to the person skilled in the art. Closer details of prodrugs are found, for example, in Fleisher et al., Advanced Drug Delivery Reviews 19 (1996) 115–130; Design of Prodrugs, H. Bundgaard, Ed., Elsevier, 1985; H. Bundgaard, Drugs of the Future 16 (1991) 443; Saulnier et al., Bioorg. Med. Chem Lett. 4 (1994) 1985; Safadi et al., Pharmaceutical Res. 10 (1993) 1350. Suitable prodrugs of the compounds of the formula I are especially ester prodrugs of carboxylic acid groups as well as acyl prodrugs and carbamate prodrugs of acylatable nitrogen-containing groups such as amino groups, amidino groups and guanidino groups. In the acyl prodrugs or carbamate prodrugs, a hydrogen atom on a nitrogen atom is replaced by an acyl group or carbamate group. Suitable acyl groups and carbamate groups for the acyl prodrugs and carbamate prodrugs are, for example, the groups R$^p$—CO and R$^{pa}$O—CO, in which R$^p$ is hydrogen, (C$_1$–C$_{18}$)-alkyl, (C$_3$–C$_{12}$)-cycloalkyl, (C$_3$–C$_{12}$)-cycloalkyl-(C$_1$–C$_8$)-alkyl, (C$_6$–C$_{14}$)-aryl, (C$_6$–C$_{14}$)-aryl-(C$_1$–C$_8$)-alkyl, heteroaryl or heteroaryl-(C$_1$–C$_8$)-alkyl and R$^{pa}$ has the meanings indicated for R$^p$ with the exception of hydrogen.

The individual structural elements in the formula I preferably have the following meanings, which they can have independently of one another.

W is preferably a divalent radical from the group consisting of R$^1$—A—C(R$^{13}$) and

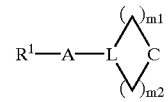

where the ring systems

can contain one or two identical or different heteroatoms from the group consisting of N and O, can be saturated or monounsaturated and can be substituted by 1 or 2 identical or different substituents R$^{13}$ and/or by one or two doubly bonded oxygen atoms, and where L is C(R$^{13}$) or N and where m1 and m2 independently of one another are one of the numbers 0, 1, 2, 3 and 4, but the sum m1+m2 is one of the numbers 3 and 4. Particularly preferably, W is the divalent radical R$^1$—A—C(R$^{13}$), where R$^{13}$ has the meanings indicated above. Very particularly preferably, W is the divalent radical R$^1$—A—C(R$^{13}$), in which R$^{13}$ has the meanings indicated above, but cannot be hydrogen. A preferred meaning of the radical R$^1$—A— in this case is (C$_1$–C$_4$)-alkyl.

Y is preferably a carbonyl group or thiocarbonyl group, particularly preferably a carbonyl group.

A is preferably a direct bond, one of the divalent radicals (C$_1$–C$_6$)-alkylene, (C$_5$–C$_6$)-cycloalkylene, phenylene, phenylene-$(C_1$–$C_4)$-alkyl, in particular phenylene-$(C_1$–$C_2)$-alkyl, or a divalent radical of a 5-membered or 6-membered saturated or unsaturated heterocycle which can contain one or two nitrogen atoms and can be monosubstituted or polysubstituted by $(C_1$–$C_6)$-alkyl or doubly bonded oxygen or sulfur.

B is preferably a divalent methylene radical or ethylene radical (=1,2-ethylene), where the methylene radical and the ethylene radical are unsubstituted or are substituted by one or more identical or different radicals from the group consisting of $(C_1$–$C_8)$-alkyl, $(C_2$–$C_8)$-alkenyl, $(C_2$–$C_8)$-alkynyl, $(C_3$–$C_{10})$-cycloalkyl, in particular $(C_3$–$C_6)$-cycloalkyl, $(C_3$–$C_{10})$-cycloalkyl-$(C_1$–$C_6)$-alkyl, in particular $(C_3$–$C_6)$-cycloalkyl-$(C_1$–$C_6)$-alkyl, optionally substituted $(C_6$–$C_{14})$-aryl, in particular optionally substituted $(C_6$–$C_{10})$-aryl, $(C_6$–$C_{14})$-aryl-$(C_1$–$C_6)$-alkyl optionally substituted in the aryl radical, in particular $(C_6$–$C_{10})$-aryl-$(C_1$–$C_6)$-alkyl optionally substituted in the aryl radical, optionally substituted heteroaryl and heteroaryl-$(C_1$–$C_6)$-alkyl optionally substituted in the heteroaryl radical. Particularly preferably, B is a methylene radical or ethylene radical substituted in this way, in particular a methylene radical substituted in this way. If an alkylene radical or alkenylene radical representing B is monosubstituted or polysubstituted, it is preferably monosubstituted, disubstituted or trisubstituted, particularly preferably monosubstituted or disubstituted, in particular monosubstituted. If a methylene radical or ethylene radical representing B is substituted, it is preferably substituted by one or two identical or different $(C_1$–$C_8)$-alkyl radicals, in particular by one $(C_1$–$C_8)$-alkyl radical, i.e. by straight-chain or branched alkyl radicals having 1, 2, 3, 4, 5, 6, 7 or 8 carbon atoms.

E is preferably tetrazolyl, $R^6CO$, $R^7CO$ or $R^{10}CO$, particularly preferably tetrazolyl or $RR^{10}CO$, very particularly preferably $R^{10}CO$.

The radicals R are preferably independently of one another hydrogen or $(C_1$–$C_8)$-alkyl, in particular hydrogen, methyl or ethyl, especially hydrogen.

$R^2$ is preferably hydrogen or $(C_1$–$C_8)$-alkyl, in particular $(C_1$–$C_6)$-alkyl, particularly preferably hydrogen, methyl or ethyl, especially hydrogen.

$R^3$ is preferably hydrogen, $(C_1$–$C_8)$-alkyl, optionally substituted $(C_6$–$C_{10})$-aryl, $(C_{6-C10})$-aryl-$(C_1$–$C_6)$-alkyl optionally substituted in the aryl radical, optionally substituted heteroaryl, heteroaryl-$(C_1$–$C_6)$-alkyl optionally substituted in the heteroaryl radical, $(C_3$–$C_8)$-cycloalkyl, $(C_3$–$C_8)$-cycloalkyl-$(C_1$–$C_6)$-alkyl, $(C_6$–$C_{12})$-bicycloalkyl, $(C_6$–$C12)$-bicycloalkyl-$(C_1$–$C_6)$-alkyl, $(C_6$–$C_{12})$-tricycloalkyl, $(C_6$–$C_{12})$-tricycloalkyl-$(C_1$–$C_6)$-alkyl, $(C_2$–$C_8)$-alkenyl, $(C_2$–$C_8)$-alkynyl, $R^{11}NH$, $COOR^{21}$, $CON(CH_3)R^4$, $CONHR^4$, $CON(CH_3)R^{15}$ or $CONHR^{15}$. Very particularly preferably, $R^3$ is hydrogen, $(C_1$–$C_8)$-alkyl, optionally substituted $(C_6$–$C_{10})$-aryl, $(C_6$–$C_{10})$-aryl-$(C_1$–$C_4)$-alkyl optionally substituted in the aryl radical, optionally substituted heteroaryl, heteroaryl-$(C_1$–$C_4)$-alkyl optionally substituted in the heteroaryl radical, $(C_3$–$C_8)$-cycloalkyl, $(C_3$–$C_8)$-cycloalkyl-$(C_1$–$C_4)$-alkyl, $(C_6$–$C_{12})$-bicycloalkyl, $(C_6$–$C_{12})$-bicycloalkyl-$(C_1$–$C_4)$-alkyl, $(C_6$–$C_{12})$-tricycloalkyl, $(C_6$–$C_{12})$-tricycloalkyl-$(C_1$–$C_4)$-alkyl, $R^{11}NH$, $COOR^{21}$, $CON(CH_3)R^4$, $CONHR^4$, $CON(CH_3)R^{15}$ or $CONHR^{15}$. Very particularly preferably, $R^3$ is hydrogen, $(C_1$–$C_8)$-alkyl, optionally substituted $(C_6$–$C_{10})$-aryl, $(C_6$–$C_{10})$-aryl-$(C_1$–$C_4)$-alkyl optionally substituted in the aryl radical, optionally substituted heteroaryl, heteroaryl-$(C_1$–$C_4)$-alkyl optionally substituted in the heteroaryl radical, $(C_3$–$C_8)$-cycloalkyl, $(C_3$–$C_8)$-cycloalkyl-$(C_1$–$C_4)$-alkyl, $R^{11}NH$, $COOR^{21}$, $CON(CH_3)R^4$, $CONHR^4$, $CON(CH_3)R^{15}$ or $CONHR^{15}$. Especially preferably, $R^3$ is hydrogen, $(C_1$–$C_8)$-alkyl, in particular $(C_1$–$C_4)$-alkyl, or optionally substituted $(C_6$–$C_{10})$-aryl.

$R^4$ is preferably $(C_1$–$C_8)$-alkyl which is unsubstituted or substituted as indicated above in the definition of $R^4$. Particularly preferably, $R^4$ is $(C_1$–$C_8)$-alkyl, in particular $(C_1$–$C_6)$-alkyl which is unsubstituted or is substituted by one or two identical or different substituents from the group consisting of hydroxyl, $(C_1$–$C_8)$-alkoxy, $R^5$, optionally substituted $(C_3$–$C_8)$-cycloalkyl, hydroxycarbonyl, aminocarbonyl, $(C_6$–$C_{10})$-aryl-$(C_1$–$C_4)$-alkoxycarbonyl which can also be substituted in the aryl radical, $(C_1$–$C_6)$-alkoxycarbonyl, $R^6$—CO, $R^7$—CO, tetrazolyl and trifluoromethyl. It is very particularly preferred if one of the substituents in the alkyl group representing $R^4$ is bonded in the 1-position of the alkyl group, i.e. to that carbon atom of the alkyl group to which also the nitrogen atom in the group $CONHR^4$ or in the group $CON(CH_3)R^4$ is bonded, and if this substituent is in the 1-position of one of the radicals hydroxycarbonyl, aminocarbonyl, $(C_6$–$C_{10})$-aryl-$(C_1$–$C_4)$-alkoxycarbonyl which can also be substituted in the aryl radical, $R^6$—CO, $R^7$—CO, $(C_1$–$C_8)$-alkoxycarbonyl or tetrazolyl. In this very particularly preferred case, the radical —$NHR^4$ or the radical —$N(CH_3)R^4$ is then the radical of an α-amino acid or of an N-methyl-α-amino acid or of a derivative thereof, where the radical of the amino acid is formally obtained by abstraction of a hydrogen atom from the amino group of the amino acid. If the substituent in the 1-position is the group $R^6$—CO, the radical —$NHR^4$ or the radical —$N(CH_3)R^4$ correspondingly is the radical of a dipeptide, tripeptide, tetrapeptide or pentapeptide. Especially preferred α-amino acids are in this case those having a lipophilic side chain, for example phenylglycine, phenylalanine, valine, leucine, isoleucine and homologs thereof, as well as derivatives of these amino acids such as esters, amides or the derivatives in which the carboxylic acid group is converted into the radical $R^6$—CO or $R^7$—CO.

$R^{10}$ is preferably hydroxyl or $(C_1$–$C_6)$-alkoxy, in particular hydroxyl or $(C_1$–$C_4)$-alkoxy.

$R^{11}$ is preferably hydrogen, $R^{12a}$, $R^{12a}$—CO, $R^{12a}$—C—CO, $R^{12b}$—CO, $R^{12b}$—CS or $R^{12a}$—$S(O)_2$, particularly preferably hydrogen, $R^{12a}$, $R^{12a}$—CO, $R^{12a}$—O—CO, $R^{12b}$—CO or $R^{12a}$—$S(O)_2$, very particularly preferably $R^{12a}$, $R^{12a}$—CO, $R^{12a}$—O—CO or $R^{12a}$—$S(O)_2$.

$R^{12a}$ is preferably $(C_1$–$C_{10})$-alkyl, $(C_2$–$C_8)$-alkenyl, $(C_2$–$C_8)$-alkynyl, $(C_5$–$C_{10})$-cycloalkyl, $(C_5$–$C_{10})$-cycloalkyl-$(C_1$–$C_8)$-alkyl, optionally substituted $(C_6$–$C_{14})$-aryl, $(C_6$–$C_{14})$-aryl-$(C_1$–$C_8)$-alkyl optionally substituted in the aryl radical, optionally substituted heteroaryl, heteroaryl-$(C_1$–$C_8)$-alkyl optionally substituted in the heteroaryl radical, or the radical $R^{15}$.

$R^{13}$ is preferably hydrogen, $(C_1$–$C_6)$-alkyl, in particular hydrogen or $(C_1$–$C_4)$-alkyl, where a preferred alkyl radical represented by $R^{13}$ is the methyl radical. $R^{13}$ is particularly preferably $(C_1$–$C_6)$-alkyl, in particular $(C_1$–$C_4)$-alkyl. $R^{13}$ is very particularly preferably methyl.

$R^{20}$ is preferably a direct bond or a divalent $(C_1$–$C_4)$-alkylene radical, particularly preferably a direct bond or a divalent $(C_1$–$C_2)$-alkylene radical, in particular a direct bond or a methylene radical or ethylene radical (1,2-ethylene), very particularly preferably a direct bond or a methylene radical.

$R^{21}$ is preferably hydrogen, $(C_1$–$C_8)$-alkyl, $(C_5$–$C_{10})$-cycloalkyl, $(C_5$–$C_{10})$-cycloalkyl-$(C_1$–$C_6)$-alkyl, optionally substituted $(C_6$–$C_{10})$-aryl, $(C_6$–$C_{10})$-aryl-$(C_1$–$C_6)$-alkyl optionally substituted in the aryl radical, the radical Het- or Het-$(C_1$–$C_6)$-alkyl, where alkyl radicals can also be monosubstituted or polysubstituted by fluorine and the radicals $R^{21}$, if they occur a number of times, are independent of one another and can be identical or different. $R^{21}$ is particularly preferably hydrogen, $(C_1–C_6)$-alkyl, $(C_5–C_6)$-cycloalkyl, $(C_5–C_6)$-cycloalkyl-$(C_1–C_4)$-alkyl, optionally substituted $(C_6–C_{10})$-aryl or $(C_6–C_{10})$-aryl-$(C_1–C_4)$-alkyl optionally substituted in the aryl radical, where alkyl radicals can be monosubstituted or polysubstituted by fluorine. $R^{21}$ is very particularly preferably hydrogen, $(C_1–C_6)$-alkyl, $(C_5–C_6)$-cycloalkyl, $(C_5–C_6)$-cycloalkyl-$(C_1–C_2)$-alkyl, optionally substituted $(C_6–C_{10})$-aryl or $(C_6–C_{10})$-aryl-$(C_1–C_2)$-alkyl optionally substituted in the aryl radical, where alkyl radials can be monosubstituted or polysubstituted by fluorine and where, again, the radicals $R^{21}$, if they occur a number of times, are independent of one another and can be identical or different.

$R^{30}$ is preferably one of the radicals $R^{32}$—CR=CR—$R^{31}$— and $R^{32}$—C≡C—$R^{31}$—, where the radicals R independently of one another can have the meanings indicated and can be identical or different.

$R^{32}$ is preferably hydrogen, $(C_2–C_8)$-alkenyl, $(C_2–C_8)$-alkynyl, $(C_3–C_{12})$-cycloalkyl, $(C_3–C_{12})$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, $(C_6–C_{12})$-tricycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical or $(C_1–C_8)$-alkyl which can optionally be substituted by 1 to 8 fluorine atoms. Particularly preferably, $R^{32}$ is hydrogen, $(C_2–C_6)$-alkenyl, $(C_2–C_6)$-alkynyl, $(C_5–C_6)$-cycloalkyl, $(C_5–C_6)$-cycloalkyl-$(C_1–C_6)$-alkyl, optionally substituted $(C_6–C_{10})$-aryl, $(C_6–C_{10})$-aryl-$(C_1–C_6)$-alkyl optionally substituted in the aryl radical, optionally substituted heteroaryl, heteroaryl-$(C_1–C_6)$-alkyl optionally substituted in the heteroaryl radical or $(C_1–C_6)$-alkyl which can optionally be substituted by 1 to 6 fluorine atoms. Very particularly preferably, $R^{32}$ is hydrogen, $(C_2–C_6)$-alkenyl, $(C_2–C_6)$-alkynyl, $(C_5–C_6)$-cycloalkyl, $(C_5–C_6)$-cycloalkyl-$(C_1–C_4)$-alkyl, optionally substituted $(C_6–C_{10})$-aryl, $(C_6–C_{10})$-aryl-$(C_1–C_4)$-alkyl optionally substituted in the aryl radical, optionally substituted heteroaryl, heteroaryl-$(C_1–C_4)$-alkyl optionally substituted in the heteroaryl radical or $(C_1–C_6)$-alkyl which can optionally be substituted by 1 to 6 fluorine atoms. If $R^{30}$ is $R^{32}$—S—$R^{31}$—, it is furthermore preferred if $R^{32}$ has a meaning other than hydrogen.

$R^{33}$ is preferably a direct bond or $(C_1–C_4)$-alkylene, particularly preferably a direct bond or $(C_1–C_2)$-alkylene, very particularly preferably a direct bond.

$R^{34}$ preferably is adivalent radical from the group consisting of $(C_5–C_{10})$-cycloalkylene, $(C_6–C_{12})$-bicycloalkylene, optionally substituted $(C_6–C_{14})$-arylene and optionally substituted heteroarylene, particularly preferably a divalent radical from the group consisting of $(C_5–C_6)$-cycloalkylene, optionally substituted $(C_6–C_{10})$-arylene and optionally substituted heteroarylene, very particularly preferably a divalent radical from the group consisting of optionally substituted $(C_6–C_{10})$-arylene and optionally substituted heteroarylene, moreover preferably for a divalent, optionally substituted $(C_6–C_{10})$-arylene radical.

$R^{35}$ is preferably a direct bond or $(C_1–C_4)$-alkylene, particularly preferably a direct bond or $(C_1–C_2)$-alkylene, in particular a direct bond or methylene or ethylene (1,2-ethylene), very particularly preferably $(C_1–C_2)$-alkylene.

$R^{36}$ is preferably a direct bond.

$R^{31}$ is preferably the divalent radical —$R^{33}$—$R^{34}$—$R^{35}$—$R^{36}$— in which one or more of the radicals $R^{33}$, $R^{34}$, $R^{35}$ and $R^{36}$ have preferred meanings. Particularly preferably, $R^{31}$ is a divalent radical from the group consisting of $(C_5–C_6)$-cycloalkylene, $(C_5–C_6)$-cycloalkylene-$(C_1–C_6)$-alkyl, optionally substituted $(C_6–C_{10})$-arylene, $(C_6–C_{10})$-arylene-$(C_1–C_6)$-alkyl optionally substituted in the arylene radical, optionally substituted heteroarylene, heteroarylene-$(C_1–C_6)$-alkyl optionally substituted in the heteroarylene radical, $(C_1–C_8)$-alkylene—CO, optionally substituted $(C_6–C_{10})$-arylene—CO, $(C_6–C_{10})$-arylene-$(C_1–C_6)$-alkyl—CO optionally substituted in the arylene radical, optionally substituted heteroarylene—CO, heteroarylene-$(C_1–C_6)$-alkyl—CO optionally substituted in the heteroarylene radical, optionally substituted $(C_6–C_{10})$-arylene-S(O)$_n$, $(C_6–C_{10})$-arylene-$(C_1–C_6)$-alkyl-S(O)$_n$ optionally substituted in the arylene radical, optionally substituted heteroarylene-S(O)$_n$ and heteroarylene-$(C_1–C_6)$-alkyl-S(O)$_n$ optionally substituted in the heteroarylene radical, where n is 1 or 2, and where the CO group and the S(O)$_n$ group are bonded to the nitrogen atom in the imidazolidine ring, and where in the case of the radicals cycloalkylenealkyl, arylenealkyl and heteroarylenealkyl the alkyl group is bonded to the nitrogen atom in the imidazolidine ring in the formula I. Very particularly preferably, $R^{31}$ is a divalent radical from the group consisting of optionally substituted $(C_6–C_{10})$-arylene and $(C_6–C_{10})$-arylene-$(C_1–C_4)$-alkyl optionally substituted in the aryl radical, where in the case of the arylenealkyl radical the alkyl group is bonded to the nitrogen atom in the imidazolidine ring in the formula I.

If $R^3$ is hydrogen or one of the radicals $(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical, $(C_3–C_8)$-cycloalkyl, $(C_3–C_8)$-cycloalkyl-$(C_1–C_8)$-alkyl, $(C_6–C_{12})$-bicycloalkyl, $(C_6–C_{12})$-bicycloalkyl-$(C_1–C_8)$-alkyl, $(C_6–C_{12})$-tricycloalkyl, $(C_6–C_{12})$-tricycloalkyl-$(C_1–C_8)$-alkyl, $(C_2–C_8)$-alkenyl, $(C_2–C_8)$-alkynyl, COOR$^{21}$, CON(CH$_3$)R$^4$, CONHR$^4$, COOR$^{15}$, CON(CH$_3$)R$^{15}$ or CONHR$^{15}$, e is preferably 0 and h is preferably 1. If $R^3$ is $R^{11}$NH, e is preferably 1 and h is preferably 0.

Preferred compounds of the formula I are those compounds in which one or more of the radicals have preferred meanings, all combinations of one or more preferred meanings or of specific meanings of radicals also being included by the present invention. Particularly preferred compounds of the formula I are those in which W is a divalent radical from the group consisting of $R^1$—A—C($R^{13}$), $R^1$—A—C($R^{13}$)=C,

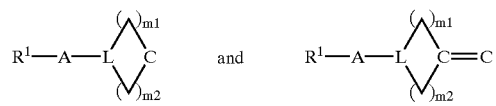

and where the ring systems

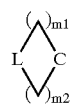

can contain one or two identical or different heteroatoms from the group consisting of N and O, can be saturated or monounsaturated and can be substituted by 1 or 2 identical or different substituents $R^{13}$ and/or by one or two doubly bonded oxygen atoms, and where L is $C(R^{13})$ or N and where m1 and m2 independently of one another are one of the numbers 0, 1, 2, 3, 4 and 5, but the sum m1+m2 is one of the numbers 3, 4 and 5;

Y is a carbonyl group or thiocarbonyl group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl or a divalent radical of a 5-membered or 6-membered saturated or unsaturated heterocycle which can contain one or two nitrogen atoms and can be monosubstituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent methylene radical or ethylene radical, where the methylene radical and the ethylene radical are unsubstituted or are substituted by one or more identical or different radicals from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is tetrazolyl, $R^6CO$, $R^7CO$ or $R^{10}CO$;

R is hydrogen, $(C_1-C_8)$-alkyl, $(C_3-C_{10})$-cycloalkyl, $(C_3-C_{10})$-cycloalkyl-$(C_1-C_6)$-alkyl, optionally substituted $(C_6-C_{10})$-aryl, $(C_6-C_{10})$-aryl-$(C_1-C_8)$-alkyl optionally substituted in the aryl radical, optionally substituted heteroaryl or heteroaryl-$(C_1-C_6)$-alkyl optionally substituted in the heteroaryl radical, where all radicals R independently of one another can have the meanings indicated and can be identical or different;

$R^1$ is hydrogen, $(C_5-C_{10})$-cycloalkyl, $(C_5-C_{10})$-cycloalkyl-$(C_1-C_6)$-alkyl, $R^{21}$-$((C_6-C_{14})$-aryl) optionally substituted in the aryl radical, $(R^{21}$—$((C_6-C_{14})$-aryl))-$(C_1-C_8)$-alkyl optionally substituted in the aryl radical, the radical Het-, Het-$(C_1-C_8)$-alkyl, one of the radicals X—NH—C(=NH)—$R^{20}$—, $X^1$—NH—$R^{20}$—, $R^{21}$O—$R^{20}$—, $R^{22}$C(O)—N($R^{21}$)—, $R^{22}$N($R^{21}$)—C(O)—, $R^{21}$O—N=, O= and S=, or $(C_1-C_{10})$-alkyl which can optionally be monosubstituted or polysubstituted by fluorine;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which can also be substituted in the aryl radical, hydroxyl, $(C_1-C_6)$-alkoxy, $(C_6-C_{14})$-aryl-$(C_1-C_6)$-alkoxy which can also be substituted in the aryl radical, or amino;

$X^1$ has one of the meanings of X or is R'—NH—C(=N—R"), where R' and R" independently of one another have the meanings of X;

$R^2$ is hydrogen, $(C_1-C_8)$-alkyl, optionally substituted $(C_6-C_{10})$-aryl or $(C_6-C_{10})$-aryl-$(C_1-C_8)$-alkyl optionally substituted in the aryl radical;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}$NH, $COOR^{21}$ $CON(CH_3)R^4$, $CONHR^4$, $COOR^{15}$, $CON(CH_3)R^{15}$ or $CONHR^{15}$;

$R^4$ is hydrogen or $(C_1-C_8)$-alkyl which is unsubstituted or is monosubstituted or polysubstituted by identical or different radicals from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{10})$-alkyl)aminocarbonyl, $(C_6-C_{14})$-aryl-$(C_1-C_8)$-alkoxycarbonyl which can also be substituted in the aryl radical, $(C_1-C_8)$-alkoxycarbonyl, $R^6$—CO, $R^7$—CO, tetrazolyl and trifluoromethyl;

$R^5$ is optionally substituted $(C_6-C_{14})$-aryl, $(C_6-C_{14})$-aryl-$(C_1-C_8)$-alkyl optionally substituted in the aryl radical or a radical of an optionally substituted monocyclic or bicyclic, 5-membered to 12-membered heterocyclic ring which can be aromatic, partially saturated or completely saturated and which can contain one, two or three identical or different heteroatoms from the group consisting of nitrogen, oxygen and sulfur;

$R^6$ is the radical of a natural or unnatural amino acid, imino acid, optionally N—$(C_1-C_8)$-alkylated or N—$((C_6-C_{14})$-aryl-$(C_1-C_8)$-alkylated) azaamino acid which can also be substituted in the aryl radical, or the radical of a dipeptide, tripeptide or tetrapeptide, as well as their esters and amides, where free functional groups can be protected by protective groups customary in peptide chemistry and where the nitrogen atoms in the amide bonds in the group $R^6$—CO can carry a radical R as a substituent;

$R^7$ is the radical of a 5-membered to 10-membered, saturated monocyclic or polycyclic heterocycle bonded via a nitrogen atom which can contain one, two, three or four identical or different additional ring heteroatoms from the group consisting of oxygen, nitrogen and sulfur and which can optionally be substituted on carbon atoms and on additional ring nitrogen atoms, where additional ring nitrogen atoms can carry identical or different radicals from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^{10}$ is hydroxyl, $(C_1-C_{10})$-alkoxy, $(C_6-C_{14})$-aryl-$(C_1-C_8)$-alkoxy which can also be substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy optionally substituted in the aryl radical, amino or mono- or di-$((C_1-C_{10})$-alkyl)amino;

$R^{11}$ is hydrogen, $R^{12a}$, $R^{12a}$—CO, $R^{12a}$—O—CO, $R^{12b}$—CO, $R^{12b}$—CS or $R^{12a}$—S(O)$_2$;

$R^{12a}$ is $(C_1-C_{10})$-alkyl, $(C_2-C_8)$-alkenyl, $(C_2-C_8)$-alkynyl, $(C_5-C_{10})$-cycloalkyl, $(C_5-C_{10})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-(($C_1$–$C_{10}$)-alkyl)amino or $R^{12a}$—NH;

$R^{13}$ is hydrogen or ($C_1$–$C_6$)-alkyl;

$R^{15}$ is $R^{16}$—($C_1$–$C_6$)-alkyl or $R^{16}$;

$R^{16}$ is a radical of a 6-membered to 14-membered bicyclic or tricyclic ring which is saturated or partially unsaturated and which can also contain one, two, three or four identical or different heteroatoms from the group consisting of nitrogen, oxygen and sulfur and which can also be substituted by one or more identical or different substituents from the group consisting of ($C_1$–$C_4$)-alkyl and oxo;

$R^{20}$ is a direct bond or ($C_1$–$C_4$)-alkylene;

$R^{21}$ is hydrogen, ($C_1$–$C_8$)-alkyl, ($C_5$–$C_{10}$)-cycloalkyl, ($C_5$–$C_{10}$)-cycloalkyl-($C_1$–$C_6$)-alkyl, optionally substituted ($C_6$–$C_{10}$)-aryl, ($C_6$–$C_{14}$)-aryl-($C_1$–$C_6$)-alkyl optionally substituted in the aryl radical, the radical Het- or Het-($C_1$–$C_6$)-alkyl, where alkyl radicals can be monosubstituted or polysubstituted by fluorine and the radicals $R^{21}$, if they occur a number of times, can be identical or different;

$R^{22}$ is one of the radicals $R^{21}$—, $R^{21}N(R^{21})$—, $R^{21}C(O)$—, $R^{21}O$—$C(O)$— or $R^{21}N(R^{21})$—$C(=N(R^{21}))$—;

$R^{30}$ is one of the radicals $R^{21}$—$(C(R)(R))_m$—$R^{31}$—, $R^{32}$—CR=CR—$R^{31}$—, $R^{32}C{\equiv}C$—$R^{31}$—, —$R^{32}$— and —SR—$R^{31}$—, where the radicals R independently of one another can have the meanings indicated and can be identical or different, and m is 1, 2 or 3;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_2$–$C_8$)-alkenyl, ($C_2$–$C_8$)-alkynyl, ($C_3$–$C_{12}$)-cycloalkyl, ($C_3$–$C_{12}$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical or ($C_1$–$C_8$)-alkyl-which can optionally be substituted by 1 to 8 fluorine atoms;

$R^{33}$ is a direct bond or a divalent ($C_1$–$C_6$)-alkylene radical;

$R^{34}$ is a divalent radical from the group consisting of ($C_5$–$C_{10}$)-cycloalkylene, ($C_6$–$C_{12}$)-bicycloalkylene, optionally substituted ($C_6$–$C_{14}$)-arylene and optionally substituted heteroarylene;

$R^{35}$ is a direct bond or a divalent ($C_1$–$C_8$)-alkylene radical;

$R^{36}$ is a direct bond, the group —CO—or the group —S(O)$_n$—;

Het is a radical of a monocyclic or polycyclic, 5-membered to 12-membered, aromatic or nonaromatic ring, which contains 1, 2, 3 or 4 identical or different heteroatoms from the group consisting of N and C as rings members and can optionally be substituted by one or more, identical or different substituents;

e and h independently of one another are 0 or 1 and can be identical or different;

n is 1 or 2;

in all their stereoisomeric forms and mixtures thereof in all ratios, and their physiologically tolerable salts.

Very particularly preferred compounds of the formula I are those in which

W is a divalent radical from the group consisting of $R^1$—A—$C(R^{13})$ and

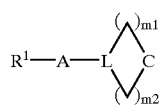

where the ring systems

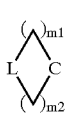

can contain one or two identical or different heteroatoms from the group consisting of N and O, can be saturated or monounsaturated and can be substituted by 1 or 2 identical or different substituents $R^{13}$ and/or by one or two doubly bonded oxygen atoms, and where L is $C(R^{13})$ or N and where m1 and m2 independently of one another are one of the numbers 0, 1, 2, 3 and 4, but the sum m1+m2 is one of the numbers 3 and 4;

Y is a carbonyl group or thiocarbonyl group;

A is a direct bond, one of the divalent radicals ($C_1$–$C_6$)-alkylene, ($C_5$–$C_6$)-cycloalkylene, phenylene, phenylene-($C_1$–$C_4$)-alkyl or a divalent radical of a 5-membered or 6-membered saturated or unsaturated heterocycle which can contain one or two nitrogen atoms and can be monosubstituted or disubstituted by ($C_1$–$C_6$)-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or are substituted by one or two identical or different radicals from the group consisting of ($C_1$–$C_8$)-alkyl, ($C_2$–$C_8$)-alkenyl, ($C_2$–$C_8$)-alkynyl, ($C_3$–$C_6$)-cycloalkyl, ($C_3$–$C_6$)-cycloalkyl-($C_1$–$C_6$)-alkyl, optionally substituted ($C_6$–$C_{10}$)-aryl, ($C_6$–$C_{10}$)-aryl-($C_1$–$C_6$)-alkyl optionally substituted in the aryl radical, optionally substituted heteroaryl and heteroaryl-($C_1$–$C_6$)-alkyl optionally substituted in the heteroaryl radical;

E is tetrazolyl or $R^{10}CO$;

R is hydrogen or ($C_1$–$C_8$)-alkyl where all radicals R independently of one another can have the meanings indicated and can be identical or different;

$R^1$ is hydrogen, $R^{21}$—(($C_6$–$C_{10}$)-aryl) optionally substituted in the aryl radical, ($R^{21}$—(($C_6$–$C_{10}$)-aryl))-($C_1$–$C_6$)-alkyl optionally substituted in the aryl radical, the radical Het-, Het-($C_1$–$C_6$)-alkyl, one of the radicals X—NH—C(=NH)—$R^{20}$—, $X^1$—NH—$R^{20}$—, $R^{22}N(R^{21})$—C(O)—, O= and S=, or ($C_1$–$C_{10}$)-alkyl which can optionally be monosubstituted or polysubstituted by fluorine;

X is hydrogen, ($C_1$–$C_6$)-alkyl, ($C_1$–$C_6$)-alkylcarbonyl, ($C_1$–$C_6$)-alkoxycarbonyl, ($C_1$–$C_8$)-alkylcarbonyloxy-($C_1$–$C_6$)-alkoxycarbonyl, optionally substituted ($C_6$–$C_{10}$)-arylcarbonyl, optionally substituted ($C_6$–$C_{10}$)-aryloxycarbonyl, ($C_6$–$C_{14}$)-aryl-($C_1$–$C_6$)-alkoxycarbonyl which can also be substituted in the aryl radical, hydroxyl, ($C_1$–$C_6$)-alkoxy or amino;

$X^1$ has one of the meanings of X or is R'—NH—C(=N—R"), where R' and R" independently of one another have the meanings of X;

$R^2$ is hydrogen or $(C_1–C_8)$-alkyl;

$R^3$ is hydrogen, $(C_1–C_8)$-alkyl, optionally substituted $(C_6–C_{10})$-aryl, $(C_6–C_{10})$-aryl-$(C_1–C_6)$-alkyl optionally substituted in the aryl radical, optionally substituted heteroaryl, heteroaryl-$(C_1–C_6)$-alkyl optionally substituted in the heteroaryl radical, $(C_3–C_8)$-cycloalkyl, $(C_3–C_8)$-cycloalkyl-$(C_1–C_6)$-alkyl, $(C_6–C_{12})$-bicycloalkyl, $(C_6–C_{12})$-bicycloalkyl-$(C_1–C_6)$-alkyl, $(C_6–C_{12})$-tricycloalkyl, $(C_6–C_{12})$-tricycloalkyl-$(C_1–C_6)$-alkyl, $(C_2–C_8)$-alkenyl, $(C_2–C_8)$-alkynyl, $R^{11}$NH, COOR$^{21}$, CON(CH$_3$)R$^4$, CONHR$^4$, CON(CH$_3$)R$^{15}$ or CONHR$^{15}$;

$R^4$ is $(C_1–C_8)$-alkyl which is unsubstituted or is monosubstituted or polysubstituted by identical or different radicals from the group consisting of hydroxyl, $(C_1–C_8)$-alkoxy, $R^5$, optionally substituted $(C_3–C_8)$-cycloalkyl, hydroxycarbonyl, aminocarbonyl, $(C_6–C_{10})$-aryl-$(C_1–C_4)$-alkoxycarbonyl which can also be substituted in the aryl radical, $(C_1–C_6)$-alkoxycarbonyl, $R^6$—CO, $R^7$—CO, tetrazolyl and trifluoromethyl;

$R^5$ is optionally substituted $(C_6–C_{12})$-aryl, $(C_6–C_{12})$-aryl-$(C_1–C_8)$-alkyl optionally substituted in the aryl radical or a radical of an optionally substituted monocyclic or bicyclic 5-membered to 12-membered heterocyclic ring which can be aromatic, partially saturated or completely saturated and which can contain one, two or three identical or different heteroatoms from the group consisting of nitrogen, oxygen and sulfur;

$R^6$ is the radical of a natural or unnatural amino acid, imino acid, optionally N—$(C_1–C_8)$-alkylated or N—$((C_6–C_{12})$-aryl-$(C_1–C_8)$-alkylated) azaamino acid which can also be substituted in the aryl radical, or the radical of a dipeptide or tripeptide, as well as their esters and amides, where free functional groups can be protected by protective groups customary in peptide chemistry and where the nitrogen atoms in the amide bonds in the group $R^6$—CO can carry a radical R as a substituent;

$R^7$ is the radical of a 5-membered to 7-membered, saturated monocyclic or bicyclic heterocycle bonded via a nitrogen atom, which can contain one, two, three or four identical or different additional ring heteroatoms from the group consisting of oxygen, nitrogen and sulfur and which can optionally be substituted on carbon atoms and on additional ring nitrogen atoms, where additional ring nitrogen atoms can carry identical or different radicals from the group consisting of hydrogen, $R^h$, HCO, $R^h$CO, $R^h$O—CO, HO—CO—$(C_1–C_4)$-alkyl and $R^h$O—CO—$(C_1–C_4)$-alkyl as substituents and $R^h$ is $(C_1–C_6)$-alkyl, $(C_3–C_8)$-cycloalkyl, $(C_3–C_8)$-cycloalkyl-$(C_1–C_8)$-alkyl, optionally substituted $(C_6–C_{10})$-aryl or $(C_6–C_{10})$-aryl-$(C_1–C_4)$-alkyl optionally substituted in the aryl radical;

$R^{10}$ is hydroxyl, $(C_1–C_8)$-alkoxy, $(C_6–C_{10})$-aryl-$(C_1–C_6)$-alkoxy which can also be substituted in the aryl radical, optionally substituted $(C_6–C_{10})$-aryloxy, $(C_1–C_8)$-alkylcarbonyloxy-$(C_1–C_4)$-alkoxy, $(C_6–C_{10})$-arylcarbonyloxy-$(C_1–C_4)$-alkoxy optionally substituted in the aryl radical, amino or mono- or di-$((C_1–C_8)$-alkyl) amino;

$R^{11}$ is hydrogen, $R^{12a}$, $R^{12a}$—CO, $R^{12a}$—O—CO, $R^{12b}$—CO or $R^{12a}$—S(O)$_2$;

$R^{12a}$ is $(C_1–C_{10})$-alkyl, $(C_2–C_8)$-alkenyl, $(C_2–C_8)$-alkynyl, $(C_5–C_{10})$-cycloalkyl, $(C_5–C_{10})$-cycloalkyl-$(C_1–C_8)$-alkyl, optionally substituted $(C_6–C_{14})$-aryl, $(C_6–C_{14})$-aryl-$(C_1–C_8)$-alkyl optionally substituted in the aryl radical, optionally substituted heteroaryl, heteroaryl-$(C_1–C_8)$-alkyl optionally substituted in the heteroaryl radical, or the radical $R^{15}$;

$R^{12b}$ is amino, di-$((C_1–C_{10})$-alkyl)amino or $R^{12a}$—NH;

$R^{13}$ is hydrogen or $(C_1–C_6)$-alkyl;

$R^{15}$ is $R^{16}$—$(C_1–C_6)$-alkyl or $R^{16}$;

$R^{16}$ is a radical of a 6-membered to 14-membered bicyclic or tricyclic radical which is saturated or partially unsaturated and which can also contain one, two, three or four identical or different heteroatoms from the group consisting of nitrogen, oxygen and sulfur and which can also be substituted by one or more identical or different substituents from the group consisting of $(C_1–C_4)$-alkyl and oxo;

$R^{20}$ is a direct bond or $(C_1–C_2)$-alkylene;

$R^{21}$ is hydrogen, $(C_1–C_6)$-alkyl, $(C_5–C_6)$-cycloalkyl, $(C_5–C_6)$-cycloalkyl-$(C_1–C_4)$-alkyl, optionally substituted $(C_6–C_{10})$-aryl, $(C_6–C_{10})$-aryl-$(C_1–C_4)$-alkyl optionally substituted in the aryl radical, the radical Het- or Het-$(C_1–C_4)$-alkyl, where alkyl radicals can be monosubstituted or polysubstituted by fluorine and the radicals $R^{21}$, if they occur a number of times, can be identical or different;

$R^{22}$ is one of the radicals $R^{21}$—, $R^{21}$N(R$^{21}$)— or $R^{21}$N(R$^{21}$)—C(=N(R$^{21}$));

$R^{30}$ is one of the radicals $R^{21}$—(C(R)(R))$_m$—$R^{31}$—, $R^{32}$—CR=CR—$R^{31}$—, $R^{32}$—C≡C—$R^{31}$—, $R^{32}$—O—$R^{31}$— and $R^{32}$—S—$R^{31}$—, where the radicals R independently of one another can have the meanings indicated and can be identical or different, and m is 1, 2 or 3;

$R^{31}$ is the divalent radical —$R^{33}$—$R^{34}$—$R^{35}$—$R^{36}$ where $R^{36}$ is bonded to the nitrogen atom in the imidazolidine ring in the formula I;

$R^{32}$ is hydrogen, $(C_2–C_6)$-alkenyl, $(C_2–C_6)$-alkynyl, $(C_5–C_6)$-cycloalkyl, $(C_5–C_6)$-cycloalkyl-$(C_1–C_6)$-alkyl, optionally substituted $(C_6–C_{10})$-aryl, $(C_6–C_{10})$-aryl-$(C_1–C_6)$-alkyl optionally substituted in the aryl radical, optionally substituted heteroaryl, heteroaryl-$(C_1–C_6)$-alkyl optionally substituted in the heteroaryl radical or $(C_1–C_6)$-alkyl which can optionally be substituted by 1 to 6 fluorine atoms;

$R^{33}$ is a direct bond or a divalent $(C_0–C_4)$-alkylene radical;

$R^{34}$ is a divalent radical from the group consisting of $(C_5–C_6)$-cycloalkylene, optionally substituted $(C_6–C_{10})$-arylene and optionally substituted heteroarylene;

$R^{35}$ is a direct bond or a divalent $(C_1–C_6)$-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1 or 2 identical or different heteroatoms from the group consisting of N and O as ring members and can optionally be substituted by one or more, identical or different substituents;

e and h independently of one another are 0 or 1 and can be identical or different;

n is 1 or 2;

in all their stereoisomeric forms and mixtures thereof in all ratios, and their physiologically tolerable salts.

Moreover preferred compounds of the formula I are those in which

W is the divalent radical $R^1$—A—$C(R^{13})$;

Y is a carbonyl group;

A is a direct bond, one of the divalent radicals $(C_1-C_6)$-alkylene, phenylene, phenylene-$(C_1-C_2)$-alkyl or a divalent radical of a 5-membered or 6-membered saturated or unsaturated heterocycle which can contain one or two nitrogen atoms and can be monosubstituted or disubstituted by $(C_1-C_6)$-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or are substituted by a radical from the group consisting of $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is tetrazolyl or $R^{10}CO$;

R is hydrogen or $(C_1-C_8)$-alkyl where all radicals R independently of one another can have the meanings indicated and can be identical or different;

$R^1$ is hydrogen, $R^{21}$—$((C_6-C_{10})$-aryl) optionally substituted in the aryl radical, $(R^{21}$—$((C_6-C_{10})$-aryl))-$(C_1-C_6)$-alkyl optionally substituted in the aryl radical, the radical Het-, Het-$(C_1-C_4)$-alkyl, one of the radicals X—NH—C(=NH)—$R^{20}$—, $X^1$—NH—$R^{20}$— and O=, or $(C_1-C_{10})$-alkyl which can optionally be monosubstituted or polysubstituted by fluorine;

X is hydrogen, $(C_1-C_6)$-alkyl, $(C_1-C_6)$-alkylcarbonyl, $(C_1-C_6)$-alkoxycarbonyl, $(C_1-C_6)$-alkylcarbonyloxy-$(C_1-C_6)$-alkoxycarbonyl, optionally substituted $(C_6-C_{10})$-arylcarbonyl, optionally substituted $(C_6-C_{10})$-aryloxycarbonyl, $(C_6-C_{14})$-aryl-$(C_1-CE)$-alkoxycarbonyl which can also be substituted in the aryl radical, hydroxyl, $(C_1-C_6)$-alkoxy or amino;

$X^1$ has one of the meanings of X or is R'—NH—C(=N—R''), where R' and R'' independently of one another have the meanings of X;

$R^2$ is hydrogen or $(C_1-C_6)$-alkyl;

$R^3$ is hydrogen, $(C_1-C_8)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl, heteroaryl-$(C_1-C_4)$-alkyl optionally substituted in the heteroaryl radical, $(C_3-C_8)$-cycloalkyl, $(C_3-C_8)$-cycloalkyl-$(C_1-C_4)$-alkyl, $(C_6-C_{12})$-bicycloalkyl, $(C_6-C_{12})$-bicycloalkyl-$(C_1-C_4)$-alkyl, $(C_6-C_{12})$-tricycloalkyl, $(C_6-C_{12})$-tricycloalkyl-$(C_1-C_4)$-alkyl, $(C_2-C_8)$-alkenyl, $(C_2-C_8)$-alkynyl, $R^{11}NH$, $COOR^{21}$, $CON(CH_3)R^4$, $CONHR^4$, $CON(CH_3)R^{15}$ or $CONHR^{15}$;

$R^4$ is $(C_1-C_6)$-alkyl which is unsubstituted or is mono- or disubstituted by identical or different radicals from the group consisting of hydroxyl, $(C_1-C_8)$-alkoxy, $R^5$, optionally substituted $(C_3-C_8)$-cycloalkyl, hydroxycarbonyl, aminocarbonyl, $(C_6-C_{10})$-aryl-$(C_1-C_4)$-alkoxycarbonyl which can also be substituted in the aryl radical, $(C_1-C_6)$-alkoxycarbonyl, $R^6$—CO, $R^7$—CO, tetrazolyl and trifluoromethyl;

$R^5$ is optionally substituted $(C_6-C_{10})$-aryl, $(C_6-C_{10})$-aryl-$(C_1-C_4)$-alkyl optionally substituted in the aryl radical or a radical of an optionally substituted monocyclic or bicyclic 5-membered to 12-membered heterocyclic ring which can be aromatic, partially saturated or completely saturated and which can contain one, two or three identical or different heteroatoms from the group consisting of nitrogen, oxygen and sulfur;

$R^6$ is a radical of a natural or unnatural amino acid or the radical of a dipeptide or tripeptide, as well as their esters and amides, where free functional groups can be protected by protective groups customary in peptide chemistry and where the nitrogen atoms in the amide bonds in the group $R^6$—CO can carry a radical R as a substituent;

$R^7$ is the radical of a 5-membered to 7-membered, saturated monocyclic heterocycle bonded via a nitrogen atom, which can contain one or two identical or different additional ring heteroatoms from the group consisting of oxygen, nitrogen and sulfur and which can optionally be substituted on carbon atoms and on additional ring nitrogen atoms, where additional ring nitrogen atoms can carry identical or different radicals from the group consisting of hydrogen, $R^h$, HCO, $R^hCO$, $R^hO$—CO, HO—CO—$(C_1-C_4)$-alkyl and $R^hO$—CO—$(C_1-C_4)$-alkyl as substituents and $R^h$ is $(C_1-C_4)$-alkyl, optionally substituted $(C_6-C_{10})$-aryl or $(C_6-C_{10})$-aryl-$(C_1-C_4)$-alkyl optionally substituted in the aryl radical;

$R^{10}$ is hydroxyl, $(C_1-C_6)$-alkoxy, $(C_6-C_{10})$-aryl-$(C_1-C_4)$-alkoxy which can also be substituted in the aryl radical, optionally substituted $(C_6-C_{10})$-aryloxy, $(C_1-C_6)$-alkylcarbonyloxy-$(C_1-C_4)$-alkoxy, $(C_6-C_{10})$-arylcarbonyloxy-$(C_1-C_4)$-alkoxy optionally substituted in the aryl radical, amino or mono- or di-$((C_1-C_8)$-alkyl)amino;

$R^{11}$ is hydrogen, $R^{12a}$, $R^{12a}$—CO, $R^{12a}$—O—CO, $R^{12B}$—CO or $R^{12A}$—$S(O)_2$;

$R^{12a}$ is $(C_1-C_8)$-alkyl, $(C_2-C_8)$-alkenyl, $(C_2-C_8)$-alkynyl, $(C_5-C_6)$-cycloalkyl, $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl, heteroaryl-$(C_1-C_4)$-alkyl optionally substituted in the heteroaryl radical, or the radical $R^{15}$;

$R^{12b}$ is amino, di-$((C_1-C_8)$-alkyl)amino or $R^{12a}$—NH;

$R^{13}$ is hydrogen or $(C_1-C_6)$-alkyl;

$R^{15}$ is $R^{16}$—$(C_1-C_6)$-alkyl or $R^{16}$;

$R^{16}$ is a radical of a 6-membered to 12-membered bicyclic or tricyclic ring which is saturated or partially unsaturated and which can also contain one, two, three or four identical or different heteroatoms from the group consisting of nitrogen, oxygen and sulfur and which can also be substituted by one or more identical or different substituents from the group consisting of $(C_1-C_4)$-alkyl and oxo;

$R^{20}$ is a direct bond or methylene;

$R^{21}$ is hydrogen, $(C_1-C_6)$-alkyl, optionally substituted $(C_6-C_{10})$-aryl, $(C_6-C_{10})$-aryl-$(C_1-C_2)$-alkyl optionally substituted in the aryl radical, the radical Het- or Het-$(C_1-C_2)$-alkyl, where alkyl radicals can be monosubstituted to tetrasubstituted by fluorine and the radicals $R^{21}$, if they occur a number of times, can be identical or different;

$R^{30}$ is one of the radicals $R^{32}$—(C(R)(R))$_m$—$R^{31}$—, $R^{32}$—CR=CR—$R^{31}$—, $R^{32}$—C≡C—$R^{31}$—, $R^{32}$—O—$R^{31}$— and $R^{32}$—S—$R^{31}$—, where the radicals R independently of one another can have the meanings indicated and can be identical or different, and m is 1, 2 or 3;

$R^{31}$ is a divalent radical from the group consisting of optionally substituted ($C_6$–$C_{10}$)-arylene, ($C_6$–$C_{10}$)-arylene-($C_1$–$C_4$)-alkyl optionally substituted in the arylene radical, ($C_5$–$C_6$)-cycloalkylene, ($C_5$–$C_6$)-cycloalkylene-($C_1$–$C_4$)-alkyl, optionally substituted heteroarylene or heteroarylene-($C_1$–$C_4$)-alkyl optionally substituted in the heteroarylene radical, where in the case of the arylenealkyl radical, the cycloalkylenealkyl radical and the heteroarylenealkyl radical the alkyl group is bonded to the nitrogen atom in the imidazolidine ring in the formula I;

$R^{32}$ is hydrogen, ($C_2$–$C_6$)-alkenyl, ($C_2$–$C_6$)-alkynyl, ($C_5$–$C_6$)-cycloalkyl, ($C_5$–$C_6$)-cycloalkyl-($C_1$–$C_4$)-alkyl, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical or ($C_1$–$C_6$)-alkyl which can optionally be substituted by 1 to 6 fluorine atoms;

Het is a radical of a monocyclic or polycyclic, 5-membered to 10-membered, aromatic or nonaromatic ring which contains 1 or 2 identical or different heteroatoms from the group consisting of N and O as ring members and can optionally be substituted by one or more, identical or different substituents;

e and h independently of one another are 0 or 1 and can be identical or different;

in all their stereoisomeric forms and mixtures thereof in all ratios, and their physiologically tolerable salts.

A series of especially preferred compounds includes those compounds of the formula I in which B is unsubstituted methylene or methylene which is substituted by a ($C_1$–$C_8$)-alkyl radical, in all their stereoisomeric forms and mixtures thereof in all ratios, and their physiologically tolerable salts. Particularly especially preferred in this series are compounds of the formula I in which B is methylene which is substituted by a ($C_1$–$C_8$)-alkyl radical, in all their stereoisomeric forms and mixtures thereof in all ratios, and their physiologically tolerable salts.

A further series of especially preferred compounds includes those compounds of the formula I in which $R^{30}$ is one of the radicals $R^{32}$—(C(R)(R))$_m$—$R^{31}$—, $R^{32}$—CR=CR—$R^{31}$—, $R^{32}$—C≡C—$R^{31}$—, $R^{32}$—O—$R^{31}$— and $R^{32}$—S—$R^{31}$—, in particular one of the radicals $R^{32}$—CR=CR—$R^{31}$— and $R^{32}$—C≡C—$R^{31}$—, where the radicals R independently of one another can have the meanings indicated and can be identical or different and m is 1, 2 or 3, and $R^{31}$ is a divalent ($C_6$–$C_{10}$)-arylene-($C_1$–$C_4$)-alkyl radical optionally substituted in the arylene radical, where the alkyl group of the arylenealkyl radical is bonded to the nitrogen atom in the imidazolidine ring in the formula I; in all their stereoisomeric forms and mixtures thereof in all ratios, and their physiologically tolerable salts.

A further series of especially preferred compounds includes those compounds of the formula I in which $R^{13}$ is hydrogen or methyl, in all their stereoisomeric forms and mixtures thereof in all ratios, and their physiologically tolerable salts. Particularly especially preferred in this series are compounds of the formula I in which the group $R^1$—A— is not hydrogen and at the same time also the group $R^{13}$ is not hydrogen, i.e. compounds in which W is not $CH_2$, in all their stereoisomeric forms and mixtures thereof in all ratios, and their physiologically tolerable salts, where it is very particularly especially preferred if $R^{13}$ in these compounds is methyl, that is, if compounds are present in which W is the divalent radical $R^1$—A—C($CH_3$) and therein $R^1$—A— has a meaning other than hydrogen, for example the meaning methyl.

A further series of especially preferred compounds includes those compounds of the formula I in which in the radical —N(R)—(C(R)(R))$_e$—C($R^2$)($R^3$)—(C(R)(R))$_h$—E, which is linked to the group —B—CO— by an amide bond, the chain of carbon atoms between the group N(R) and the first group which is bonded to this chain and which is an acid group such as a carboxylic acid group, sulfonic acid group, phosphonic acid group or a derivative thereof such as an ester or an amide or a tetrazolyl group, contains two or more than two carbon atoms, in all their stereoisomeric forms and mixtures thereof in all ratios, and their physiologically tolerable salts. This first acid group (or the derivative thereof) which, starting from the group N(R), is bonded to this chain of carbon atoms, can be represented by the group E or by the group $R^3$, if the latter, for example, is COO$R^{21}$, CONH$R^4$, COR$^6$, COR$^7$ etc. Particularly especially preferred in this series are compounds of the formula I in which in the radical —N(R)—(C(R)(R))$_e$—C($R^2$)($R^3$)—(C(R)(R))$_h$—E the chain of carbon atoms between the group N(R) and the first group which is bonded to this chain and which is an acid group or a derivative thereof comprises just two carbon atoms, in all their stereoisomeric forms and mixtures thereof in all ratios, and their physiologically tolerable salts. Particularly especially preferred compounds of the formula I of this type can be, for example, compounds in which e is 1, that is compounds which contain the group —N(R)—(C(R)(R)—C($R^2$)($R^3$)—(C(R)(R))$_h$—E, where in the case of these compounds h can be 1 or 0 and where it is preferred in the case of these compounds if $R^3$ is $R^{11}$ NH and at the same time h is 0, in all their stereoisomeric forms and mixtures thereof in all ratios, and their physiologically tolerable salts. Particularly especially preferred compounds of the formula I of this type can, for example, also be compounds in which e is 0, h is 1 and $R^3$ is not an acid group or a derivative thereof, in all their stereoisomeric forms and mixtures thereof in all ratios, and their physiologically tolerable salts, that is compounds which contain a radical —N(R)—(C($R^2$)($R^{3a}$)—(C(R)(R)—E in which $R^{3a}$ is defined as $R^{3a}$ but cannot be a carboxylic acid group or a derivative thereof such as an ester or an amide. In these compounds, $R^{3a}$ is preferably hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, ($C_3$–$C_8$)-cycloalkyl, ($C_3$–$C_8$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, ($C_2$–$C_8$)-alkenyl or ($C_2$–$C_8$)-alkynyl. In these compounds, $R^{3a}$ is particularly preferably hydrogen, ($C_1$–$C_6$)-alkyl, optionally substituted ($C_6$–$C_{10}$)-aryl, ($C_6$–$C_{10}$)-aryl-($C_1$–$C_4$)-alkyl optionally substituted in the aryl radical, optionally substituted heteroaryl, heteroaryl-($C_1$–$C_4$)-alkyl optionally substituted in the heteroaryl radical, ($C_5$–$C_6$)-cycloalkyl, ($C_5$–$C_6$)-cycloalkyl-($C_1$–$C_4$)-alkyl, ($C_{10-C12}$)-tricycloalkyl or ($C_{10}$–$C_{12}$)-tricycloalkyl-($C_1$–$C_4$)-alkyl. It is furthermore preferred in the compounds of this series if the group —N(R)— in the radical —N(R)—(C(R)(R))$_e$—C(R$^2$)(R$^3$)—C(R)(R))$_h$—E is the group —NH—.

A further series of especially preferred compounds comprises those compounds of the formula I in which in the radical —N(R)—(C(R)(R))$_e$—C(R$^2$)(R$^3$)—(C(R)(R))$_h$—E the chain of carbon atoms between the group N(R) and the first group bonded to this chain, which is an acid group or a derivative thereof, only comprises one carbon atom, in all their stereoisomeric forms and mixtures thereof in all ratios and their physiologically tolerable salts, but where in these compounds the first acid group or the derivative thereof which, starting from the group N(R), is bonded to the chain of carbon atoms, must fulfill the following condition: the first acid group or the derivative thereof is an amide group which in an alkyl substituent on the amide nitrogen does not contain a carboxylic acid group or a derivative thereof such as an ester group or an amide group bonded to this alkyl substituent, or the first acid group is a free acid group (or a salt thereof), or the first acid group or the derivative thereof is an ester group. Compounds of this series can be, for example, compounds of the formula I in which e is 0 and R$^3$ is COOR$^{21}$, COOR$^{15}$ CONHR$^{15}$ or CON(CH$_3$)R$^{15}$, preferably CONHR$^{15}$, and h is 0 or 1, preferably 1. Compounds of this series can, for example, also be compounds of the formula I in which e is 0, h is 0 or 1, preferably 1, and R$^3$ is CON(CH$_3$)R$^4$ or CONHR$^4$, but in which a (C$_1$–C$_{10}$)-alkyl radical representing R$^4$ cannot be substituted by a carboxylic acid group or a derivative thereof such as an ester or an amide, that is, for example, compounds in which R$^4$ is hydrogen or in particular (C$_1$–C$_{10}$)-alkyl which is unsubstituted or is substituted by one or more identical or different radicals from the group consisting of hydroxyl, (C$_1$–C$_8$)-alkoxy, R$^5$, optionally substituted (C$_3$–C$_8$)-cycloalkyl, tetrazolyl, trifluoromethyl.

Generally, compounds of the formula I are preferred which have a uniform configuration at chiral centers, for example when appropriately substituted on the carbon atom carrying the radicals R$^2$ and R$^3$ or on the center W in the imidazolidine ring in the formula I, where the individual chiral centers independently of one another can have the R configuration or the S configuration.

The compounds of the formula I can be prepared, for example, by fragment condensation of a compound of the formula II

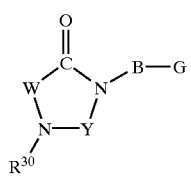

(II)

with a compound of the formula III,

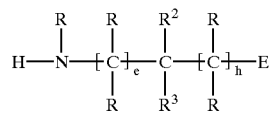

(III)

where, in the formulae II and III, the groups W, Y, B, E, R, R$^2$, R$^3$, R$^{30}$ as well as e and h are defined as indicated above or alternatively functional groups can be present in protected form or in the form of precursor groups, and where G is hydroxycarbonyl, (C$_1$–C$_6$)-alkoxycarbonyl or activated carboxylic acid derivatives such as acid chlorides or active esters. With respect to the compounds of the formula III it is also possible, if compounds of the formula I are to be prepared in which, for example, R$^3$ in the formula I is a carboxylic acid derivative or contains such a derivative, that the radical R$^3$ initially is a hydroxycarbonyl group present in protected form or contains such a group, and that the desired final group R$^3$ is synthesized in one or more further steps only after the condensation of the compounds of the formulae II and III.

For the condensation of the compounds of the formula II with those of the formula III, the coupling methods of peptide chemistry well known per se to the person skilled in the art are advantageously used (see, for example, Houben-Weyl, Methoden der Organischen Chemie [Methods of Organic Chemistry], Volume 15/1 and 15/2, Georg Thieme Verlag, Stuttgart, 1974). Possible condensing agents or coupling reagents are, for example, carbonyldiimidazole, carbodiimides such as dicyclohexylcarbodiimide or diisopropylcarbodiimide, O-((cyano(ethoxycarbonyl) methylene)amino)—N,N,N',N'-tetramethyluronium tetrafluoroborate (TOTU) or propylphosphonic anhydride (PPA).

The condensations can be carried out under well known standard conditions. In the condensation, as a rule it is necessary for nonreacting amino groups present to be protected by reversible protective groups. The same applies to carboxyl groups not involved in the reaction, which during the condensation are preferably present as (C$_1$–C$_6$)-alkyl esters, benzyl esters or tert-butyl esters. Amino group protection is unnecessary if the amino groups are still present in the form of precursors, for example as nitro groups or cyano groups, and are only formed after the condensation, for example by hydrogenation. After the condensation, the protective groups present are removed in a suitable manner. For example, NO$_2$ groups (guanidino protection in amino acids), benzyloxycarbonyl groups and benzyl groups in benzyl esters can be removed by hydrogenation. The protective groups of the tert-butyl type are removed under acidic conditions, while the 9-fluorenylmethyloxycarbonyl radical is removed by secondary amines. The compounds of the formula I can also be prepared, for example, by synthesizing the compounds stepwise on a solid phase according to customary methods, where the individual structural elements of the molecule can be introduced in different sequences.

Compounds of the formula II in which w is R$^1$—A—C (R$^{13}$) and Y is a carbonyl group can be prepared, for example, by first reacting compounds of the formula IV

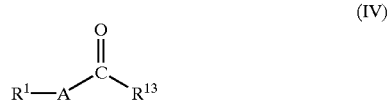

(IV)

in a Bucherer reaction to give compounds of the formula V

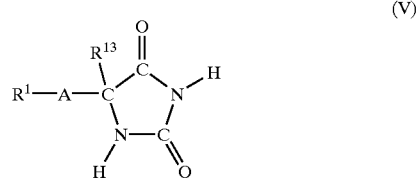

(V)

(H. T. Bucherer, V. A. Lieb, J. Prakt. Chem. 141 (1934), 5), where, in the formulae IV and V, the groups R$^1$, R$^{13}$ and A are defined as indicated above. Compounds of the formula VI,

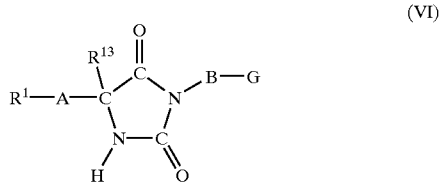

in which $R^1$, $R^{13}$, A, B and G are defined as indicated above, can then be obtained by, for example, first reacting the compounds of the formula V with an alkylating reagent which introduces the radical —B—G into the molecule. The reaction of compounds of the formula VI with a second reagent of the formula $R^{30}$—LG, in which $R^{30}$ has the meanings indicated above and LG is a nucleophilically substitutable leaving group, for example halogen, in particular chlorine, bromine or iodine, sulfonyloxy such as tosyloxy, methylsulfonyloxy or trifluoromethylsulfonyloxy, $(C_1-C_4)$-alkoxy, optionally substituted phenoxy or a heterocyclic leaving group such as, for example, imidazolyl, then leads to the corresponding compounds of the formula II.

Generally, depending on the meanings of the radical $R^{30}$ and other radicals, it can also be advantageous not to introduce the final radical $R^{30}$ into the molecule by means of the reagent $R^{30}$—LG, but after linkage of a precursor of the group $R^{30}$ to the imidazolidine ring, to build up the radical $R^{30}$ on the imidazolidine ring. This can be carried out, for example, at the stage of the compound of the formula VI or the compound of the formula II prepared therefrom or at the stage of another intermediate of the synthesis. For example, a compound of the formula VI can be reacted with a compound of the formula RG—$R^{31}$—LG to the give the compound of the formula VII

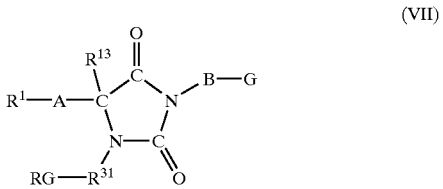

in which A, B, G, $R^1$, $R^{13}$ and $R^{31}$ have the meanings indicated above. In the formula RG—$R^{31}$—LG, LG, as above, is a nucleophilically substitutable leaving group, for example halogen, in particular chlorine, bromine or iodine, or a sulfonyloxy radical. RG— in the formula RG—$R^{31}$—LG and in the formula VII is a reactive group which can be converted into one of the radicals $R^{31}$—C(R)(R))$_m$—, $R^{32}$—CR=CR—, $R^{32}$—C≡C—, $R^{32}$—O— and $R^{32}$—S—. RG can be, for example, halogen, cyano or a carbonyl group. The conversion of the group RG into the desired target group can take place in one or more steps and can be carried out according to standard processes familiar to the person skilled in the art. By way of example, this procedure is explained below for the preparation of compounds of the formula II in which $R^{30}$ is $R^{32}$—CR=CR—.

Thus, compounds of the formula VI can be converted into compounds of the formula VII in which the group RG is a group which is a precursor for an aldehyde group and which is then converted into an aldehyde group in the next reaction step. For example, a compound of the formula VI can first be reacted with a cyano compound of the formula NC—$R^{31}$—LG to give a compound of the formula VII, in which RG is cyano. The cyano group can then be converted into an aldehyde group by reduction (for example analogously to D. M. Flanagan and M. M. Joullie, Synthetic Communications 1990, 20, 459–467). The aldehyde group can then be reacted in a Horner-Emmons reaction, for example with a phosphorane of the formula $R^{32}$—C(R)=P(O)(OC$_2$H$_5$)$_2$ using a suitable base such as, for example, sodium hydride, or in another customary carbonyl olefination reaction to give a compound of the formula II, in which $R^{30}$ is $R^{32}$—CR=CR—$R^{31}$—. Numerous further conversions can be carried out in compounds of the formula II according to this procedure.

Furthermore, compounds of the formula VII in which RG is halogen can be prepared from compounds of the formula VI using a reagent of the formula Hal—$R^{31}$—LG in which Hal is halogen, in particular chlorine, bromine or iodine. Compounds of this type can be reacted, for example, in a Heck reaction in the presence of a palladium(0) catalyst with olefins of the formula $R^{32}$—CR=CHR, for example with styrenes, to give compounds of the formula II in which $R^{30}$ is $R^{32}$—CR=CR—$R^{31}$—, for example to give stilbene derivatives (compare R. F. Heck, Org. Reactions 1982, 27, 345). Analogously, compounds of the formula II in which $R^{30}$ is $R^{32}$—C≡C—$R^{31}$—, for example tolan derivatives, can be obtained from compounds of the formula VII in which RG is halogen in a Heck reaction in the presence of a palladium(O) catalyst using acetylenes of the formula $R^{31}$—C≡CH, for example using phenylacetylenes.

A further example of conversions which may be mentioned is reactions of compounds in which $R^{30}$ is $R^{32}$—O—$R^{31}$—. Compounds of the formula VI can be reacted with compounds of the formula PG—O—$R^{31}$—LG in which LG is defined as above and PG is an alcohol protective group, for example a benzyl group or an easily removable ether radical. If the group PG, for example, is a benzyl group, the compound of the formula VII obtained is already a compound of the formula II in which $R^{30}$ is benzyl—O—$R^{31}$—. In this compound of the formula II, the benzyl group, however, can also be removed by catalytic hydrogenation (or another protective group can be removed in a suitable manner) and the hydroxyl group released can then be etherified according to standard processes, further compounds of the formula II being obtained in which $R^{30}$ is $R^{31}$—O—$R^{31}$—. Such etherifications can be carried out, for example, with optionally substituted alkyl halides in the presence of bases such as potassium carbonate or with alcohols under the conditions of the Mitsunobu reaction. The same applies to compounds in which $R^{30}$ is $R^{31}$—S—$R^{31}$—.

In compounds of the formula II, but likewise also in compounds of the formula I, double bonds and triple bonds in the group $R^{30}$ can be converted into one another and into single bonds. Compounds of the formulae II or I in which $R^{30}$ is $R^{32}$—CR=CR—$R^{31}$— can be converted by catalytic hydrogenation into compounds in which $R^{30}$ is $R^{32}$—(C(R)(R))$_m$—$R^{31}$— and m=2. Compounds in which $R^{30}$ is $R^{32}$—C≡C—$R^{31}$— can be converted into compounds having a C—C single bond by complete hydrogenation or into compounds having a C—C double bond by partial hydrogenation. Compounds in which $R^{30}$ is $R^{32}$—CR=CR—$R^{31}$— can be converted into the corresponding dibromides by bromination of the double bond with elementary bromine and subsequently into compounds in which $R^{30}$ is $R^{32}$—C≡C—$R^{31}$— by dehydrohalogenation, for example tolan derivatives (see, for example, G. W. Kabalka, K. Yang, N. K. Reddy, C. Narayana, Synthetic Communications 1998, 28(5), 925–929; S. Nakatsuji, K. Matsuda, Y. Uesugi, K. Nakashima, S. Akiyama and W. Fabian, J. Chem. Sco. Perk.

Trans. I 1992, 755–758; K. Fukunaga and H. Yamaguchi, Synthesis 1981, 879–880).

According to this procedure, numerous further compounds of the formula I can be synthesized, the reactions to be carried out always being standard processes which are familiar to the person skilled in the art.

Very generally, the individual steps in the preparation of the compounds of the formula I can be carried out according to or analogously to known methods familiar to the person skilled in the art. Depending on the individual case, it may here be appropriate, as already explained, in all steps in the synthesis of the compounds of the formula I to block functional groups which could lead to side reactions or undesired reactions by means of a protective group strategy suited to the synthesis problem as is known to the person skilled in the art.

The explained procedure of not introducing functional groups into the molecule directly in the final form, but first introducing precursors into the molecule and then synthesizing the final functional group at the stage of an intermediate, can, as already mentioned, correspondingly also be used for other parts of the molecule of the formula I, for example for the group $R^1$ or the group $R^3$.

Compounds of the formula II in which W is

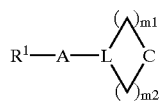

and Y is a carbonyl group can be prepared, for example, by reacting compounds of the formula VIII,

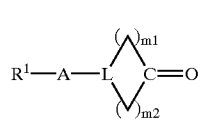

(VIII)

in which $R^1$, A, L, m1 and m2 are defined as indicated above, in a Bucherer reaction as described above for the preparation of the compounds of the formula V to give compounds of the formula IX

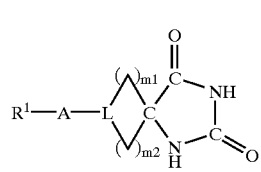

(IX)

and converting these using a reagent which introduces the radical —B—G into the molecule as described above for the preparation of the compounds of the formula VI into compounds of the formula X

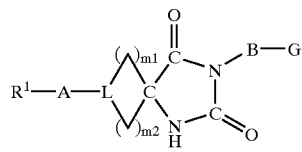

(X)

where in the compounds of the formulae IX and X the groups $R^1$, A, B, G and L and also m1 and m2 have the meanings indicated above. The compounds of the formula X can then in turn be reacted according to the reactions of the compounds of the formula VI described above.

If W is $R^1$—A—C($R^3$)=C or the radical

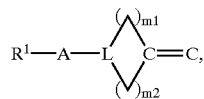

this structural element can be introduced, for example, by condensing the corresponding aldehyde or the corresponding ketone analogously to known methods with a dioxo or thioxo-oxo-imidazolidine which contains an unsubstituted methylene group in the position which corresponds to the group W.

The amino compounds of the formula III are commercially available or can be synthesized according to or analogously to well known standard processes from starting compounds which are commercially available or are obtainable according to or analogously to literature procedures.

Compounds of the formula I in which W is $R^1$—A—C($R^{13}$) can also be obtained as follows:

By reaction of α-amino acids or N-substituted α-amino acids obtainable according to standard procedures or preferably their esters, for example the methyl ester, ethyl ester, tert-butyl ester or benzyl ester, for example of compounds of the formula XI

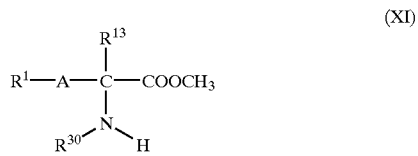

(XI)

in which $R^1$, $R^{13}$, $R^{30}$ and A are defined as indicated above, with an isocyanate or isothiocyanate, for example of the formula XII

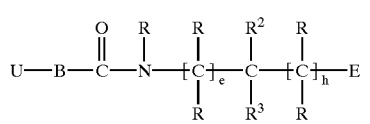

(XII)

in which B, E, R, $R^2$, $R^3$, e and h are defined as indicated above and U is isocyanato or isothiocyanato, urea derivatives or thiourea derivatives, for example of the formula XIII

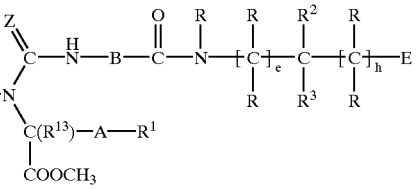

(XIII)

are obtained for which the definitions indicated above apply and in which Z is oxygen or sulfur. The compounds of the formula XIII can be cyclized by heating with acid to give compounds of the formula Ia

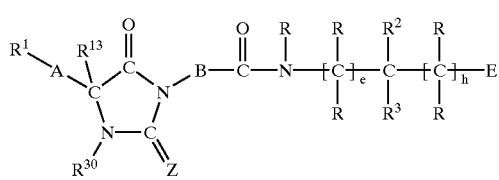

(Ia)

for which the meanings indicated above apply. The cyclization of the compounds of the formula XIII to give the compounds of the formula Ia can also be carried out by treatment with bases in inert solvents, for example by treatment with sodium hydride in an aprotic solvent such as dimethylformamide. During the cyclization, functional groups can in turn be present in protected form.

Compounds of the formula I in which W is $R^1$—A—C($R^{13}$) can also be obtained by reacting a compound of the formula XI with an isocyanate or isothiocyanate of the formula XIV

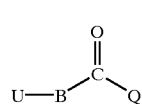

(XIV)

in which B and U are defined as indicated above for the formula XII and Q is an alkoxy group, for example a ($C_1$–$C_4$)-alkoxy group such as methoxy, ethoxy or tert-butoxy, a ($C_6$–$C_{14}$)-aryloxy group, for example phenoxy, or a ($C_6$–$C_{14}$)-aryl-($C_1$–$C_4$)-alkoxy group, for example benzyloxy. In this case a compound of the formula XV

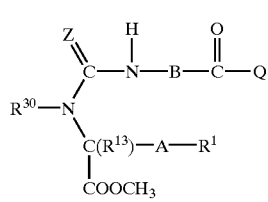

(XV)

is obtained in which Z is oxygen or sulfur and A, B, Q, $R^1$, $R^{13}$ and $R^{30}$ are defined as indicated above for the formulae XI and XIV, which is then cyclized under the influence of an acid or of a base, such as described above for the cyclization of the compounds of the formula XIII, to give a compound of the formula XVI,

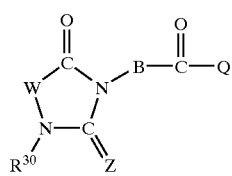

(XVI)

in which W is $R^1$—A—C(Rl3) and Z, B, Q and $R^{30}$ are defined as indicated above. From the compound of the formula XVI, a compound of the formula Ia can then be obtained by hydrolysis of the group CO—Q to the carboxylic acid COOH and subsequent coupling with a compound of the formula III, as described above for the coupling of the compounds of the formulae II and III. Here too, during the cyclization functional groups can be present in protected form or in the form of precursors. Instead of compounds of the formula XI, it is also possible to start from analogous compounds which contain a hydrogen atom in the amino group instead of the group $R^{30}$ and then later to introduce the group $R^{30}$ into the molecule in one or more steps as explained.

A further method for the preparation of compounds of the formula Ia is, for example, the reaction of compounds of the formula XVII

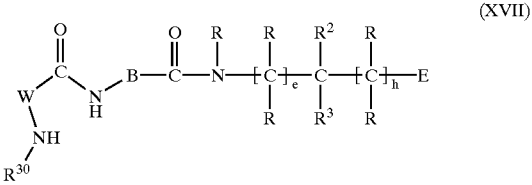

(XVII)

in which W is $R^1$—A—C($R^{13}$) and for which otherwise the definitions indicated above apply, with phosgene or thiophosgene or corresponding equivalents (analogously to S. Goldschmidt and M. Wick, Liebigs Ann. Chem. 575 (1952), 217–231 and C. Tropp, Chem. Ber. 61 (1928), 1431–1439).

A guanidino group contained in the radical $R^1$ can be obtained, for example, with the following reagents from an amino group which in turn, for example, is obtainable from a nitro group or a cyano group by reduction:

1. O-Methylisourea (S. Weiss and H. Krommer, Chemiker-Zeitung 98 (1974), 617–618)
2. S-Methylisothiourea (R. F. Borne, M. L. Forrester and I. W. Waters, J. Med. Chem. 20 (1977), 771–776)
3. Nitro-S-methylisothiourea (L. S. Hafner and R. E. Evans, J. Org. Chem. 24 (1959) 1157)
4. Formamidinosulfonic acid (K. Kim, Y.-T. Lin and H. S. Mosher, Tetrah. Lett. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953), 4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-, N,N'-dialkoxycarbonyl-, N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, Arzneim. Forsch./Drug Res. 34 (1984), 531–542).

Amidines can be prepared from the corresponding cyano compounds by addition of alcohols, for example methanol or ethanol, in acidic anhydrous medium, for example dioxane, methanol or ethanol, and subsequent aminolysis, for example treatment with ammonia in alcohols such as, for example, isopropanol, methanol or ethanol (G. Wagner, P. Richter and Ch. Garbe, Pharmazie 29 (1974), 12–55). A further method for preparing amidines is the addition of hydrogen sulfide to the cyano group, followed by methylation of the resulting thioamide and subsequent reaction with ammonia (GDR Patent No. 235 866). Furthermore, hydroxylamine can be added to the cyano group, N-hydroxyamidines being formed which, if desired, can likewise be converted into the amidines, for example by hydrogenation.

With respect to the preparation of the compounds of the formula I, reference is furthermore made to the complete disclosure of WO-A-95/14008, EP-A-796 855 and the applications corresponding to them, as well as to WO-A-96/33976. In particular, also with respect to the preparation of the compounds of the formulae V and VI in racemic form and in enantiomerically pure form, reference is made to the corresponding details in WO-A-96/33976, which are part of the present disclosure.

The compounds of the formula I are valuable pharmaceutical active compounds which are suitable, for example, for the therapy and prophylaxis of inflammatory disorders, allergic disorders or asthma. The compounds of the formula I and their physiologically tolerable salts can be administered according to the invention to animals, preferably to mammals, and in particular to humans, as pharmaceuticals for therapy or prophylaxis. They can be administered per se, in mixtures with one another or in the form of pharmaceutical preparations which permit enteral or parenteral administration and which as active ingredient contain an efficacious dose of at least one compound of the formula I and/or its physiologically tolerable salts in addition to customary pharmaceutically acceptable vehicles and/or additives.

The present invention therefore also relates to the compounds of the formula I and/or their physiologically tolerable salts for use as pharmaceuticals, the use of the compounds of the formula I and/or their physiologically tolerable salts for the production of pharmaceuticals for the therapy and prophylaxis of the diseases described above or in the following, for example for the therapy and prophylaxis of inflammatory disorders, and the use of the compounds of the formula I and/or their physiologically tolerable salts in the therapy and prophylaxis of these diseases. The present invention furthermore relates to pharmaceutical preparations (or pharmaceutical compositions) which contain an efficacious dose of at least one compound of the formula I and/or its physiologically tolerable salts in addition to a customary pharmaceutically acceptable carrier.

The pharmaceuticals can be administered systemically or locally. They can be administered, for example, orally in the form of pills, tablets, film-coated tablets, sugar-coated tablets, granules, hard and soft gelatin capsules, powders, solutions, syrups, emulsions, suspensions or in other pharmaceutical forms. However, administration can also be carried out vaginally or rectally, for example in the form of suppositories, or parenterally or by implantation, for example in the form of injection solutions or infusion solutions, microcapsules or rods, or topically or percutaneously, for example in the form of ointments, solutions or tinctures, or in another way, for example in the form of nasal sprays or aerosol mixtures. Parenterally, administration can be carried out, for example, intravenously, intramuscularly, subcutaneously, intraarticularly, intrasynovially or in another manner.

The pharmaceutical preparations according to the invention are prepared in a manner known per se, pharmaceutically inert inorganic or organic vehicles being used in addition to the compound(s) of the formula I and/or its/their physiologically tolerable salts. For the preparation of pills, tablets, sugar-coated tablets and hard gelatin capsules, it is possible to use, for example, lactose, cornstarch or derivatives thereof, talc, stearic acid or its salts etc. Vehicles for soft gelatin capsules and suppositories are, for example, fats, waxes, semisolid and liquid polyols, natural or hardened oils etc. Suitable vehicles for the preparation of solutions, for example injection solutions, or of emulsions or syrups are, for example, water, alcohols, diols, glycerol, polyols, sucrose, invert sugar, glucose, vegetable oils etc. Suitable vehicles for microcapsules, implants or rods are, for example, copolymers of glycolic acid and lactic acid. The pharmaceutical preparations normally contain approximately 0.5 to 90% by weight of the compounds of the formula I and/or their physiologically tolerable salts. The amount of active compound of the formula I and/or its salts in the pharmaceutical preparations is normally 0.2 to 500 mg, preferably 1 to 200 mg, but also larger amounts of active compound can be contained.

In addition to the active compounds and vehicles, the pharmaceutical preparations can additionally contain additives (or excipients), such as, for example, fillers, disintegrants, binders, lubricants, wetting agents, stabilizers, emulsifiers, preservatives, sweeteners, colorants, flavorings, aromatizers, thickeners or diluents, buffer substances, solvents, solubilizers, means for achieving a depot effect, salts for altering the osmotic pressure, coating agents or antioxidants. They can also contain two or more compounds of the formula I and/or their physiologically tolerable salts. Furthermore, they can also contain one or more other therapeutically or prophylactically active substances, for example substances having antiinflammatory action, in addition to at least one compound of the formula I and/or its physiologically tolerable salts.

If the compounds of the formula I or pharmaceutical preparations comprising them are administered as aerosols, for example in the form of nasal aerosols or by inhalation, this can be carried out, for example, using a spray, an atomizer, a pump atomizer, an inhalation apparatus, a metered inhaler or a dry powder inhaler. Pharmaceutical forms for administration of the compounds of the formula I as an aerosol can be prepared according to processes well known to the person skilled in the art. For example, solutions or dispersions of the compounds of the formula I in water, water/alcohol mixtures or suitable saline solutions using customary additives, for example benzyl alcohol or other suitable preservatives, absorption enhancers for increasing the bioavailability, solubilizers, dispersents and others, and, if appropriate, customary propellants, for example fluorochlorohydrocarbons and/or fluorohydrocarbons, are suitable for their preparation.

The compounds of the formula I have, for example, the ability to inhibit cell-cell interaction processes and cell-matrix interaction processes in which interactions between VLA-4 with its ligands play a part. The efficacy of the compounds of the formula I can be demonstrated, for example, in an assay in which the binding of cells which contain the VLA-4 receptor, for example of leukocytes, to ligands of this receptor is measured, for example to VCAM-1 which for this purpose can advantageously also be prepared by genetic engineering. Details of such an assay are described below. In particular, the compounds of the formula I are able to inhibit the adhesion and the migration of leukocytes, for example the adhesion of leukocytes to endothelial cells which— as explained above—is controlled via the VCAM-1/VLA-4 adhesion mechanism. Other than as antiinflammatory agents, the compounds of the formula I and their physiologically tolerable salts are therefore generally suitable for the therapy and prophylaxis of diseases which are based on the interaction between the VLA-4 receptor and its ligands or can be affected by an inhibition of this interaction, and in particular they are suitable for the therapy and prophylaxis of diseases which are caused at least partially by an undesired extent of leukocyte adhesion and/or leukocyte migration or are associated therewith, and for whose prevention, alleviation or cure the adhesion and/or migration of leukocytes should be decreased.

The present invention therefore also relates to the compounds of the formula I for the inhibition of the adhesion and/or migration of leukocytes or for the inhibition of the VLA-4 receptor and to the use of the compounds of the formula I for the preparation of pharmaceuticals therefor, that is of pharmaceuticals for the therapy or prophylaxis of diseases in which leukocyte adhesion and/or leukocyte migration exhibits an undesired extent, or for the therapy or prophylaxis of diseases in which VLA-4-dependent adhesion processes play a part, and to the use of the compounds of the formula I and/or their physiologically tolerable salts in the therapy and prophylaxis of diseases of this type.

The compounds of the formula I can be employed as antiinflammatories in the case of inflammatory symptoms of very different cause in order to prevent, to reduce or to suppress the undesirable or harmful sequelae of inflammation. They are used, for example, for the therapy or prophylaxis of arthritis, of rheumatoid arthritis, of polyarthritis, of inflammatory bowel disease (ulcerative colitis), of systemic lupus erythematosus, for the therapy or prophylaxis of inflammatory disorders of the central nervous system such as, for example, multiple sclerosis, or for the therapy or prophylaxis of asthma or of allergies, for example allergies of the delayed type (type IV allergy). They are furthermore suitable for the therapy or prophylaxis of cardiovascular disorders, of arteriosclerosis, of restenoses, of diabetes, of damage to organ transplants, of immune disorders, of autoimmune disorders, of tumor growth or formation of tumor metastases in various malignancies, of malaria as well as of other diseases in which blocking of the integrin VLA-4 and/or influencing of the leukocyte activity appears appropriate for prevention, alleviation or cure.

The dose when using the compounds of the formula I can vary within wide limits and, as usual, is to be tailored to the individual conditions in each individual case, a fact which is known to the physician. It depends, for example, on the nature and severity of the disease to be treated, on the compound employed or on whether an acute or chronic disease state is treated or whether prophylaxis is conducted, or on whether, in addition to the compounds of the formula I, further active compounds are administered. In general, in the case of oral administration a daily dose of approximately 0.01 to 100 mg/kg, preferably 0.1 to 10 mg/kg, in particular 0.3 to 2 mg/kg (in each case per kg of body weight) is appropriate in an adult weighing about 75 kg to achieve effective results. In the case of intravenous administration, the daily dose is in general approximately 0.01 to 50 mg/kg, preferably 0.01 to 10 mg/kg of body weight. In particular when relatively large amounts are administered, the daily dose can be divided into two or more, for example 2, 3 or 4, part administrations. If appropriate, depending on individual behavior, it may be necessary to deviate upward or downward from the indicated daily dose.

The compounds of the formula I and their salts can furthermore be employed for diagnostic purposes, for example in in-vitro diagnoses, and as auxiliaries in biochemical investigations in which VLA-4 blocking or influencing of cell-cell or cell-matrix interactions is demanded. They can furthermore be used as intermediates for the preparation of other compounds, in particular of other pharmaceutical active compounds, which are obtainable from the compounds of the formula I, for example, by modification or introduction of radicals or functional groups.

EXAMPLES

The products were identified by means of mass spectra (MS) and/or NMR spectra. Basic compounds which were purified by chromatography using an eluent which contained, for example, acetic acid or trifluoroacetic acid, and then freeze-dried, or which were treated with an acid, for example with trifluoroacetic acid, and for working up were freeze-dried, for example, sometimes still contained the acid used, depending on how the freeze drying or working up was carried out, and were thus obtained partially or completely in the form of a salt of the acid used, for example in the form of the acetic acid salt or trifluoroacetic acid salt. Indicated mixing ratios of solvents or reagents are volume ratios.

The abbreviations have the following meanings:

| MTBE | methyl tert-butyl ether |
|---|---|
| DMF | N,N-dimethylformamide |
| THF | tetrahydrofuran |
| DCC | N,N'-dicyclohexylcarbodiimide |
| TOTU | O-(cyano(ethoxycarbonyl)methylene)amino)-N,N,N',N'-tetramethyluronium tetrafluoroborate |
| HOBt | 1-hydroxybenzotriazole |
| TFA | trifluoroacetic acid |
| Phosphazene P1 | tert-butylimino-tris(dimethylamino)-phosphorane |

The compounds were prepared in the ways shown in schemes 1 to 3 according to the general processes described below. tBu is tert-butyl, alkyl in scheme 1 is methyl or ethyl. In the process according to scheme 1, for the preparation of the intermediate of the formula VIa an α-amino acid alkyl ester substituted in the α position by the groups $R^{13}$ and $R^1$—A— was reacted with a tert-butyl isocyanatocarboxylate to give the urea and this was cyclized using sodium hydride (steps A and B). It is also possible to start from an hydantoin substituted in the 4 position by the groups $R^{13}$ and $R^1$—A— and to alkylate this with a tert-butyl bromocarboxylate (step C). The intermediate of the formula VIa can be employed in situ in the following synthesis step or can be isolated.

According to one of the variants carried out, the intermediate of the formula VIa was reacted with a compound of the formula $R^{30}$—LG (see general synthesis description), for example with 4-chloromethylstilbene of the formula $C_6H_5$—CH═CH—$C_6H_4$—(4-$CH_2$Cl) (step D). Subsequently, the tert-butyl ester group was cleaved to give the acid by means of trifluoroacetic acid, a compound of the formula IIa being obtained (step E).

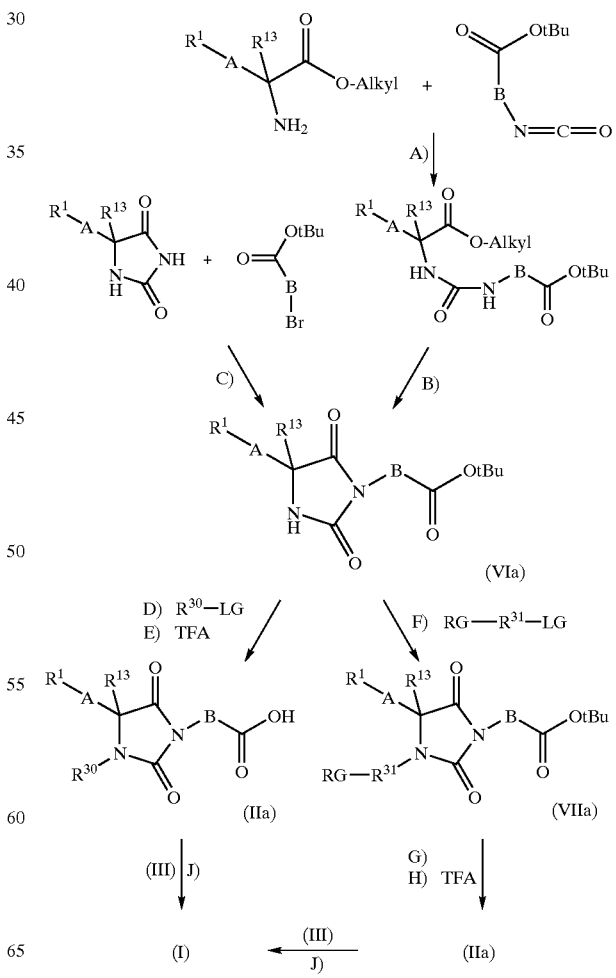

Scheme 1

According to another variant, the compound of the formula VIa was converted using a compound of the formula RG—R$^{31}$—LG (see general synthesis description) to a compound of the formula VIIa (step F), in which the group RG—R$^{31}$— was then converted into the group R$^{30}$ (general step G). Conversions carried out in step G are shown in detail in schemes 2 and 3.

Scheme 2 shows the conversion of a cyano-substituted hydantoin of the formula VIIb, i.e. a compound of the formula VIIa where RG=cyano, by reduction of the cyano group to the aldehyde group (step K) and reaction of the aldehyde group in a Horner-Emmons reaction to give the compound of the formula VIIc (step L). Compounds of the formula VIIb were obtained by alkylation of compounds of the formula VIa, for example using 4-cyanobenzyl bromide.

Scheme 2

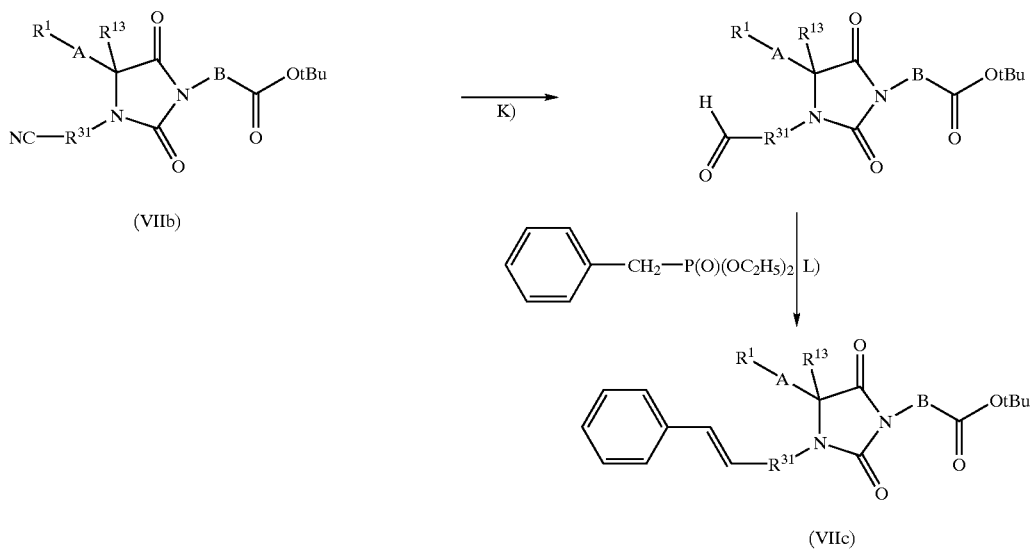

Scheme 3 shows the conversion of a halogen-substituted hydantoin of the formula VIId, i.e. a compound of the formula VIIa where RG=halogen (in the formula VIId Hal is halogen, in particular iodine or bromine). Compounds of the formula VIId were obtained by alkylation of compounds of the formula VIa, for example using 4-iodobenzyl bromide to give 3-(4-iodobenzyl) hydantoins and were reacted with styrenes in a Heck reaction in the presence of a palladium catalyst to give compounds of the formula VIIe (step M) or with phenylacetylenes to give compounds of the formula VIIf (step N)(see R. F. Heck, Org. React. 1982, 27, p. 345).

Scheme 3

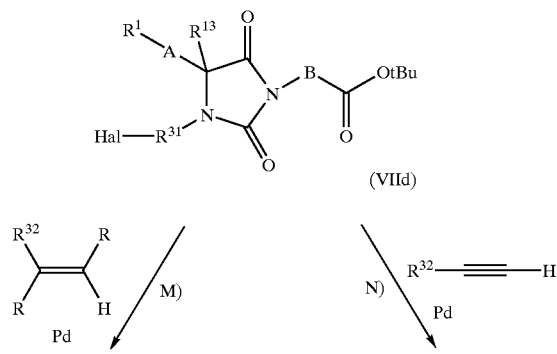

-continued

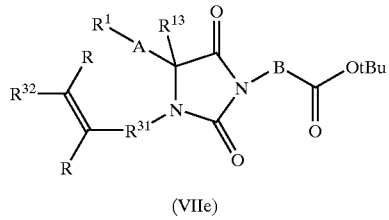

(VIIe)

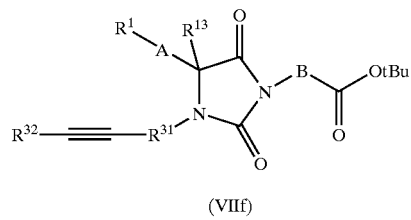

(VIIf)

In the compounds obtained in the steps L, M, N or generally in step G, the tert-butyl ester group was then in turn converted into the carboxylic acid group using trifluoroacetic acid (step H). The intermediate of the formula IIa obtained in the steps E or H was then coupled to an amino compound of the formula formula III, in which an optionally present carboxylic acid group was protected as the tert-butyl ester, and finally the target compound of the formula I was obtained after removal of the tert-butyl ester protective group (step J; scheme 1). The starting compounds employed in the individual steps follow from the structures of the individual examples.

In the individual synthesis steps, the reaction was carried out according to the following general process procedures.

Steps A and B

The α-amino acid alkyl ester (90 mmol) was dissolved in 200 ml of DMF and treated with 1 equivalent of the tert-butyl isocyanatocarboxylate. The mixture was stirred at room temperature for 12 h (complete conversion after TLC checking). The solution of the resulting urea in DMF (total volume 230 ml) was employed in the following reaction without further purification and working up.

For the cyclization of the urea to the hydantoin, an aliquot of the urea solution was cooled to 0° C. and treated with 1.2 equivalents (based on the urea) of sodium hydride (as a 55% strength suspension in mineral oil). The mixture was stirred at 0° C. for 15 min and then at room temperature for 2 h. (complete conversion according to TLC checking (heptane/MTBE, 1/1)). The solvent was removed on a rotary evaporator. The residue was purified by flash chromatography (silica gel, heptane/MTBE, 6/4). The cyclized hydantoin was obtained in a yield of >90%.

Step C

For the preparation of the compounds of the formula VIa, the starting hydantoin can be dissolved in DMF and treated with 1.2 equivalents of sodium hydride (55% strength suspension in mineral oil). In general, the mixture is then stirred at room temperature for 4 h. After addition of 1.7 equivalents of the tert-butyl bromocarboxylate, stirring is continued at room temperature overnight. The solvent is removed on a rotary evaporator. The residue is purified by flash chromatography.

Step D (Reacting with 4-Chloromethylstilbene)

1.1 equivalents each (based on the hydantoin) of 4-chloromethylstilbene and sodium hydride were added to the hydantoin obtained in step B and the mixture was stirred at room temperature for 4 h. The reaction was quenched by addition of water and the solvent was stripped off on a rotary evaporator. The oily residue was taken up in ethyl acetate and washed with water. The organic phase was dried over magnesium sulfate and the solvent was removed in vacuo. The residue was purified by flash chromatography (silica gel, hexane/MTBE, 6/4). In addition to a fraction which contained the pure 3-alkylated hydantoin derivative in a yield of 50–60%, further fractions were obtained which contained the product in slightly impure form.

Step F (Reaction with 4-Cyanobenzyl Bromide)

The alkylated hydantoin obtained in step B (14 mmol) was dissolved in 50 ml DMF and treated with 1.2 equivalents of cesium carbonate and 1 equivalent of 4-cyanobenzyl bromide and the mixture was stirred at room temperature for 16–20 h. The reaction mixture was quenched by addition of water and the solvent was stripped off on a rotary evaporator. The oily residue was taken up in ethyl acetate and washed with water. The organic phase was dried over magnesium sulfate and the solvent was removed in vacuo. The 3-(4-cyanobenzyl)hydantoin derivative was obtained in a yield of about 60%.

Step K

The 3-(4-cyanobenzyl)hydantoin derivative obtained in step F (about 14 mmol) was dissolved in 360 ml of a mixture of pyridine/acetic acid/water (2/1/1), cooled to 0° C. and treated with 25.1 g of sodium hypophosphite (monohydrate) and 4.17 g of moist Raney nickel. After stirring at 60° C. for 6 h, the solvents were removed in vacuo and the residue was taken up in ethyl acetate. The solvent was washed with 10% strength citric acid solution, saturated sodium bicarbonate solution and saturated sodium chloride solution and dried over magnesium sulfate. After filtration and concentration, the 3-(4-formylbenzyl)hydantoin derivative obtained was employed in the next step without further purification.

Step L 150 mg (6.24 mmol) of sodium hydride (60% strength suspension in oil) were added to 1.16 g (4.8 mmol) of diethyl benzylphosphonate (dissolved in 20 ml of DMF). The mixture was stirred at room temperature for 15 minutes. 2.0 g (4.8 mmol) of the 3-(4-formylbenzyl)hydantoin derivative obtained in step K were then added and the mixture was stirred at room temperature for 16 h. The solvent was stripped off under reduced pressure and the residue was taken up in ethyl acetate. The solution was washed with water, dried over magnesium sulfate and filtered. The filtrate was concentrated in vacuo and the oily residue was chromatographed on silica gel (n-heptane/ethyl acetate, 6/1). The fractions containing the target compound were combined and the solvent was removed. About 60% of the desired stilbene were obtained.

Step F (Reaction with 4-Iodobenzyl Bromide)

The alkylated hydantoin obtained in step B (14 mmol) was dissolved in 50 ml of DMF, treated with 1.1 equivalents each of phosphazene P-1 as a base and 4-iodobenzyl bromide and the mixture was stirred at room temperature for 2–3 h. The reaction mixture was quenched by addition of water and the solvent was stripped off on a rotary evaporator. The oily residue was taken up in ethyl acetate and washed with water. The organic phase was dried over magnesium sulfate and the solvent was removed in vacuo. The residue was purified by flash chromatography (silica gel, hexane/MTBE, 6/4). The pure 3-(4-ibdobenzyl)hydantoin derivative was obtained in a yield of about 60%.

Step M

The 3-(4-iodobenzyl)hydantoin derivative obtained in step F (7 mmol) was dissolved in 30 ml of DMF and treated with 2 equivalents of the styrene of the formula $R^{32}$—CR=CHR and palladium(II) acetate/triphenylphosphine. The mixture was heated at 90° C. for 14 h (complete conversion according to TLC checking (ethyl acetate/petroleum ether, ¼)). The solvent was removed in vacuo and the residue was purified by flash chromatography (silica gel, ethyl acetate/petroleum ether, ¼). The product was obtained in a yield of about 80%.

Step N

The 3-(4-iodobenzyl)hydantoin derivative (7 mmol) was dissolved in 30 ml DMF and treated with 2 equivalents of the phenylacetylene of the formula $R^{32}$—C≡CH and palladium(II) acetate/triphenylphosphine. The mixture was heated at 90° C. for 14 h (complete conversion according to TLC checking (ethyl acetate/petroleum ether, ¼). The solvent was removed in vacuo and the residue was purified by flash chromatography (silica gel, ethyl acetate/petroleum ether, ¼). The product was obtained in a yield of about 80%.

Steps E and H

The tert-butyl ester obtained in steps D, L, M or N was shaken at room temperature for 1 h in trifluoroacetic acid/dichloromethane (1/1; about 20 ml/mmol) for conversion into the carboxylic acid. The trifluoroacetic acid was removed on a rotary evaporator and the residue was freeze-dried. The carboxylic acid was obtained in a quantitative yield.

Step J

The carboxylic acid obtained in step E or H (about 2 mmol) was dissolved in 10 ml of DMF and treated with 1 equivalent of the amino compound to be coupled, in which a carboxylic acid group was present as the tert-butyl ester, and 1 equivalent of HOBt. The mixture was cooled to 0° C., treated with 1 equivalent of DCC and stirred at 0° C. for 1 h. It was then stirred at room temperature for 4 h (complete conversion according to TLC checking (dichloromethane/methanol, 20/1)).

The mixture was filtered and the solvent was removed in vacuo. Purification of the residue by flash chromatography (silica gel, dichloromethane/methanol, 20/1) afforded the coupling product in a yield of >80%. For the cleavage of the tert-butyl ester protective group, the coupling product was dissolved in trifluoroacetic acid/dichloromethane (1/1; about 20 ml/mmol) and shaken at room temperature for 1 h. The solvent was removed on a rotary evaporator. The residue was freeze-dried, in some cases after addition of acetic acid/water, or purified by chromatography. The acid designated below in the individual examples was obtained in quantitative yield.

Instead of using amino compounds in solution, the carboxylic acids obtained in step E or H can also be coupled to resin-bonded amino compounds, which can also be synthesized on the resin. If an aminocarboxylic acid is to be employed in the coupling as an amino compound, for the linkage of the aminocarboxylic acid or of the C-terminal unit of an amino compound, which is to be synthesized on the resin, to the polymeric carrier, the resin (Wang, polystyrene, Bachem) is treated with 2 equivalents of the Fmoc-protected amino carboxylic acid, 2 equivalents of HOBt and 2 equivalents of TOTU. 2 equivalents of diisopropylethylamine, dissolved in DMF (10 ml/g of resin), are added to the mixture. The mixture is shaken at 40° C. for 12 h. 1 equivalent of acetic anhydride and 1 equivalent of diisopropylethylamine is then added to the mixture and it is shaken at room temperature for a further 30 min. The solvent is removed by filtration, and the residue is washed 5 times in each case with DMF, toluene and dichloromethane. The loading of the resin is determined on a sample by Fmoc cleavage according to standard methods of peptide synthesis (depending on the amino acid employed, the loading is in general 0.3 to 0.6 mmol/g of resin). For the removal of the Fmoc group, the resin is then suspended in a 20% strength solution of piperidine in DMF (10 ml of solution/g of resin) and shaken for 20 min. The solution is filtered off and the process is repeated. The resin is then washed repeatedly with DMF and dichloromethane. The resin-bonded amino acid (100 mg of resin) is treated with 2 equivalents of the carboxylic acid to be coupled, 2 equivalents of HOBt and 2 equivalents of TOTU. 2 equivalents of diisopropylethylamine, dissolved in 2 ml of DMF, are added to the mixture. The mixture is shaken at room temperature for 12 h. It is filtered and then washed 5 times in each case with DMF, toluene and dichloromethane. For the removal of the coupling product from the support, the purified resin is treated with 1 ml of trifluoroacetic acid/dichloromethane (1/1) and shaken for 1 h. The cleavage solution is concentrated, the residue is filtered with ethyl acetate through a cartridge packed with silica gel for purification and the solvent is removed. If compounds were prepared according to this procedure, it is indicated below that resin-bonded amino compounds were employed.

General Process for the Preparation of 3-substituted tert-butyl 3-amino Propionates Employed in Step J The appropriate 3-substituted acrylic acid (0.1 mol) was dissolved in 100 ml of dichloromethane with 1.1 equivalents of oxalyl chloride. The mixture was stirred at room temperature for 4 h. The solvent was removed on a rotary evaporator. The residue was taken up in 100 ml of tert-butanol and stirred at room temperature for 2 h. After the reaction was complete, the solvent was removed on a rotary evaporator. The residue was dissolved in diethyl ether and washed with water, sodium hydrogencarbonate solution and again with water. The organic phase was dried over magnesium sulfate and the solvent was removed in vacuo. The 3-substituted tert-butyl acrylate was obtained in a yield of >80%.

For the introduction of the amino group, 0.95 equivalent of n-butyllithium (in n-hexane) were added dropwise over a period of 1 h to a solution of (R)-(+)—N-benzyl-N-(1-phenylethyl)amine (60 mmol) in 100 ml of THF at −70° C. The mixture was stirred at this temperature for 1 h, then a solution of the 3-substituted tert-butyl acrylate (0.9 equivalent) in 75 ml of THF was added dropwise over a period of 1 h. The mixture was stirred at −70° C. for 2 h. After removing the cooling, 115 ml of 5% strength citric acid solution were added dropwise. The solution was stirred for 1 h, treated with ethyl acetate and washed with water. The organic phase was washed with sodium hydrogencarbonate solution and water and dried over magnesium sulfate. The solvent was removed in vacuo. The residue was purified by flash chromatography (silica gel, heptane/ethyl acetate, 9/1). The 3-substituted tert-butyl 3-(N-benzyl-N-(1-phenylethyl)amino)propionate was obtained in a yield of about 50% as a yellow oil. For the removal of the benzyl group and of the phenylethyl group, the substance (about 30 mmol) was dissolved in 200 ml of a mixture of ethyl acetate/acetic acid (4/1) and treated with 1.5 g of Pd(OH)$_2$. It was hydrogenated at room temperature for 8 h under a hydrogen atmosphere. The catalyst was filtered off and the filtrate was concentrated on a rotary evaporator. The residue was taken up in ether/water. The aqueous phase was neutralized with sodium hydrogencarbonate and extracted repeatedly with ether. The combined organic phases were dried over magnesium sulfate and carefully concentrated on a rotary evaporator. The 3-substituted tert-butyl 3-aminopropionate was obtained as a highly liquid, readily volatile oil in a yield of >50%.

Example 1

(R)-3-((S)-2-(4,4-Dimethyl-3-(4-styrylbenzyl)-2,5-dioxoimidazolidin-1-yl)-2-(2-methylpropyl)acetylamino)-3-methylpropionic Acid

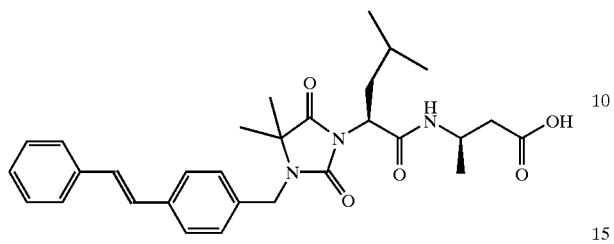

The compound was prepared according to the general preparation processes, steps A, B, D, E and J. In step D, tert-butyl (S)-2-(4,4-dimethyl-2,5-dioxoimidazolidin-1-yl)-2-(2-methylpropyl)acetate was alkylated with 4-chloromethylstilbene. In step J, tert-butyl (R)-3-amino-3-methylpropionate was employed as an amino compound.

Yield: 170 mg
ES(+)-MS: 520.4 (M+H)

Example 2

(R)-3-((S)-2-(4,4-Dimethyl-3-(4-(2-phenylethyl)benzyl)-2,5-dioxoimidazolidin-1-yl)-2-(2-methylpropyl)acetylamino)-3-methylpropionic Acid

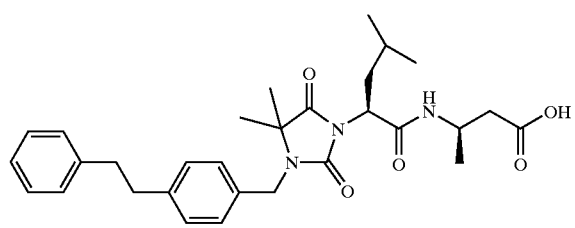

The compound was prepared by catalytic hydrogenation of the styryl compound obtained in Example 1 (Pd/C, 1 bar hydrogen overpressure, methanol, room temperature).

Yield: 102 mg
ES(+)-MS: 522.4 (M+H)

Example 3

(R)-3-((S)-2-(4,4-Dimethyl-3-(4-styrylbenzyl)-2,5-dioxoimidazolidin-1-yl)-2-(2-methylpropyl)acetylamino)-3-phenylpropionic Acid

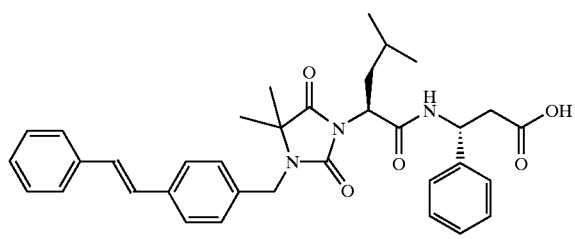

The compound was prepared according to the general preparation processes, steps A, B, D, E and J. In step J, the amino compound employed was tert-butyl (R)-3-amino-3-phenylpropionate.

Yield: 130 mg

ES(+)-MS: 582.6 (M+H)

Example 4

3-((S)-2-(4,4-Dimethyl-3-(4-styrylbenzyl)-2,5-dioxo-imidazolidin-1-yl)-2-(2-methylpropyl)acetylamino)propionic Acid

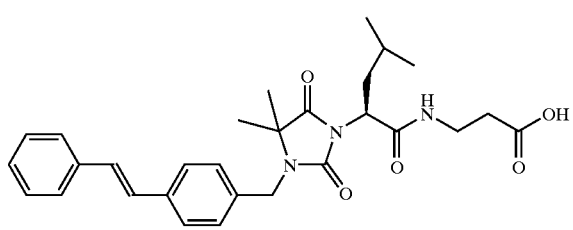

The compound was prepared according to the general preparation processes, steps A, B, D, E and J. In step J, the amino compound employed was β-alanine tert-butyl ester.

Yield: 102 mg

ES(+)-MS: 506.5 (M+H)

Example 5

(R)-3-((S)-2-(4,4-Dimethyl-3-(4-styrylbenzyl)-2,5-dioxo-imidazolidin-1-yl)-2-(2-methylpropyl)acetylamino)-3-(3,4-methylenedioxyphenyl)propionic Acid

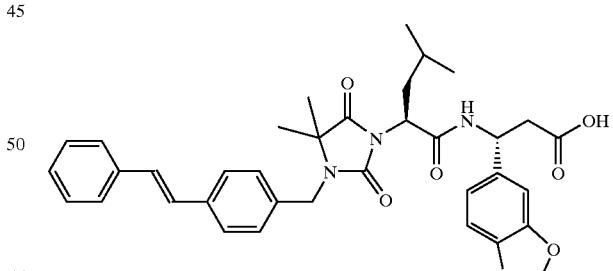

The compound was prepared according to the general preparation processes, steps A, B, D, E and J. In step J, the amino compound employed was tert-butyl (R)-3-amino-3-(3,4-methylenedioxyphenyl)propionate.

Yield: 320 mg

ES(+)-MS: 626.2 (M+H)

Example 6

(R)-3-((S)-2-(4,4-Dimethyl-2,5-dioxo-3-(4-phenyloxy-20 benzyl)imidazolidin-1-yl)-2-(2-methylpropyl)acetylamino)-3-(3,4-methylenedioxyphenyl)propionic Acid

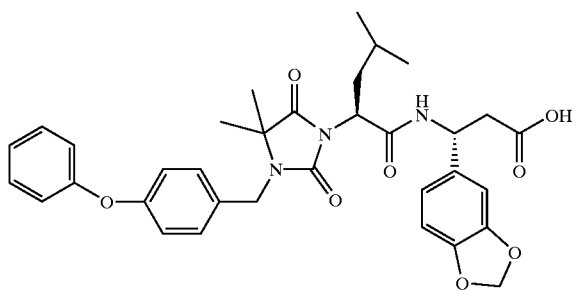

The compound was prepared according to the general reparation processes, steps A, B, D, E and J. In step D, tert-butyl (S)-2-(4,4-dimethyl-2,5-dioxoimidazolidin-1-yl)-2-(2-methylpropyl)acetate was alkylated with 4-phenoxybenzyl bromide. In step J, the amino compound employed was tert-butyl (R)-3-amino-(3,4-methylenedioxyphenyl)propionate.

Yield: 205 mg

ES(+)-MS: 616.3 (M+H)

Example 7

(R)-3-((S)-2-(3-(4-Benzyloxybenzyl)-4,4-dimethyl-2,5-dioxoimidazolidin-1-yl)-2-(2-methylpropyl)acetylamino)-3-methylpropionic Acid

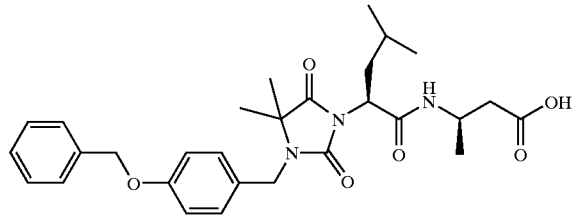

The compound was prepared according to the general preparation processes, steps A, B, D, E and J. In step D, tert-butyl (S)-2-(4,4-dimethyl-2,5-dioxoimidazolidin-1-yl)-2-(2-methylpropyl)acetate was alkylated with 4-benzyloxybenzyl bromide. In step J, the amino compound employed was tert-butyl (R)-3-amino-3-methylpropionate.

Yield: 11.5 mg

ES(+)-MS: 524.4 (M+H)

Example 8

(R)-3-((S)-2-(4,4-Dimethyl-3-(4-(2-(2-methylphenyl)-vinyl)benzyl)-2,5-dioxoimidazolidin-1-yl)-2-(2-methyl-propyl)acetylamino)-3-methylpropionic Acid

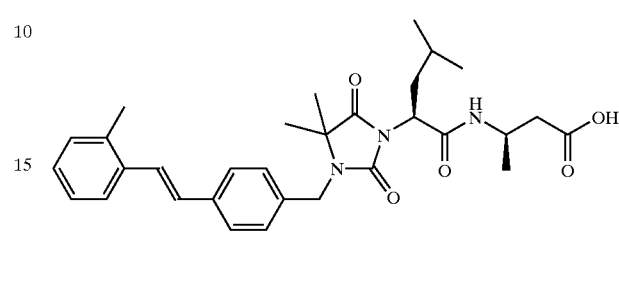

The compound was prepared according to the general preparation processes, steps A, B, F (reaction with 4-cyanobenzyl bromide), K, L, H and J. In step J, the amino compound employed was tert-butyl (R)-3-amino-3-methylpropionate.

Yield: 260 mg

ES(+)-MS: 534.4 (M+H)

Example 9

(R)-3-((S)-2-(4,4-Dimethyl-3-(4-(2-(2-methylphenyl)-vinyl)benzyl)-2,5-dioxoimidazolidin-1-yl)-2-(2-methyl-propyl)acetylamino)-3-phenylpropionic Acid

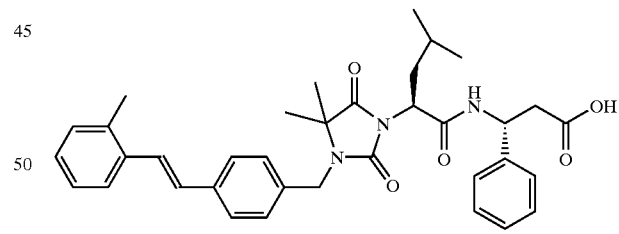

The compound was prepared according to the general preparation processes, steps A, B, F (reaction with 4-cyanobenzyl bromide), K, L, H and J. In step J, the amino compound employed was tert-butyl (R)-3-amino-3-phenyl propionate.

Yield: 85 mg

ES(+)-MS: 596.4 (M+H)

Example 10

3-((S)-2-(4,4-Dimethyl-3-(4-styrylbenzyl)-2,5-dioxo-imidazolidin-1-yl)-2-(2-methylpropyl)acetylamino)-3-(3-methoxyphenyl)propionic Acid

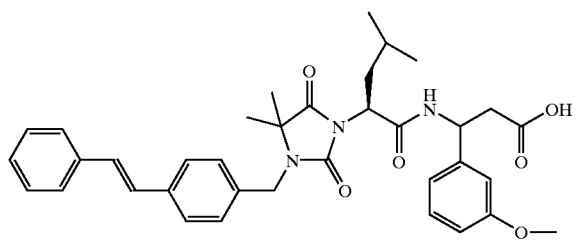

The compound was prepared according to the general preparation processes, steps A, B, D, E and J. In step J, the amino compound employed was 3-amino-3-(3-methoxyphenyl)propionic acid bonded to Wang resin.

Yield: 2.9 mg

ES(+)-MS: 612.7(M+H)

Example 11

3-((S)-2-(4,4-Dimethyl-3-(4-styrylbenzyl)-2,5-dioxo-imidazolidin-1-yl)-2-(2-methylpropyl)acetylamino)-3-(4-fluorophenyl)propionic Acid

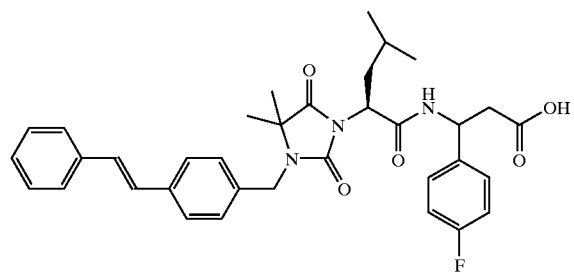

The compound was prepared according to the general preparation processes, steps A, B, D, E and J. In step J, the amino compound employed was 3-amino-3-(4-fluorophenyl)propionic acid bonded to Wang resin.

Yield: 4.1 mg

ES(+)-MS: 600.7 (M+H)

Example 12

3-((S)-2-(4,4-Dimethyl-3-(4-styrylbenzyl)-2,5-dioxo-imidazolidin-1-yl)-2-(2-methylpropyl)acetylamino)-3-(3-fluoro-4-methoxyphenyl)propionic Acid

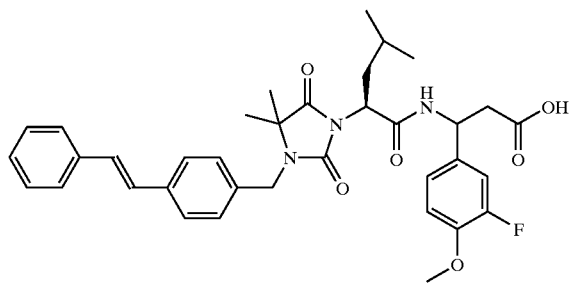

The compound was prepared according to the general preparation processes, steps A, B. D, E and J. In step J, the amino compound employed was 3-amino-3-(3-fluoro-4-methoxyphenyl)propionic acid bonded to Wang resin.

Yield: 2.3 mg

ES(+)-MS: 630.7(M+H)

Example 13

3-((S)-2-(4,4-Dimethyl-3-(4-styrylbenzyl)-2,5-dioxo-imidazolidin-1-yl)-2-(2-methylpropyl)acetylamino)-3-(3-methylphenyl)propionic Acid

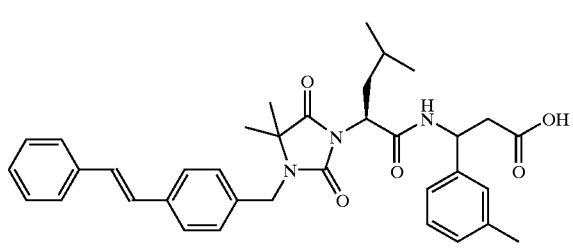

The compound was prepared according to the general preparation processes, steps A, B, D, E and J. In step J, the amino compound employed was 3-amino-3-(3-methylphenyl)propionic acid bonded to Wang resin.

Yield: 5.0 mg

ES(+)-MS: 596.7(M+H)

Example 14

3-((S)-2-(4,4-Dimethyl-3-(4-styrylbenzyl)-2,5-dioxo-imidazolidin-1-yl)-2-(2-methylpropyl)acetylamino)-3-(2-fluorophenyl)propionic Acid

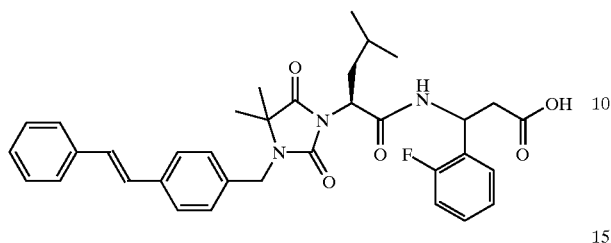

The compound was prepared according to the general preparation processes, steps A, B, D, E and J. In step J, the amino compound employed was 3-amino-3-(2-fluorophenyl)propionic acid bonded to Wang resin.

Yield: 4.9 mg

ES(+)-MS: 600.7(M+H)

Example 15

3-((S)-2-(4,4-Dimethyl-3-(4-styrylbenzyl)-2,5-dioxo-imidazolidin-1-yl)-2-(2-methylpropyl)acetylamino)-3-(3-fluorophenyl)propionic acid

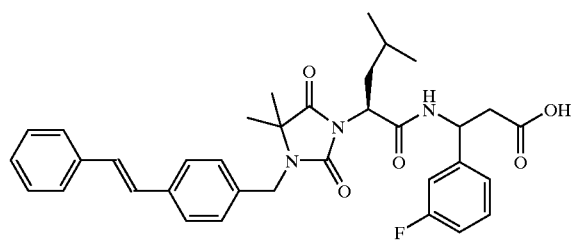

The compound was prepared according to the general preparation processes, steps A, B, D, E and J. In step J, the amino compound employed was 3-amino-(3-fluorophenyl)propionic acid bonded to Wang resin.

Yield: 4.2 mg

ES(+)-MS: 600.7(M+H)

Example 16

3-(4-Butylphenyl)-3-((S)-2-(4,4-dimethyl-3-(4-styrylbenzyl)-2,5-dioxoimidazolidin-1-yl)-2-(2-methyl-propyl)acetylamino)propionic Acid

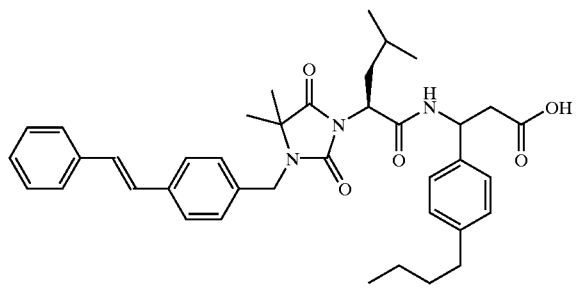

The compound was prepared according to the general preparation processes, steps A, B, D, E and J. In step J, the amino compound employed was 3-amino-3-(4-butylphenyl)propionic acid bonded to Wang resin.

Yield: 8.5 mg

ES(+)-MS: 638.7(M+H)

Example 17

3-(4-Chlorophenyl)-3-((S)-2-(4,4-dimethyl-3-(4-styrylbenzyl)-2,5-dioxoimidazolidin-1-yl)-2-(2-methyl-propyl)acetylamino)propionic Acid

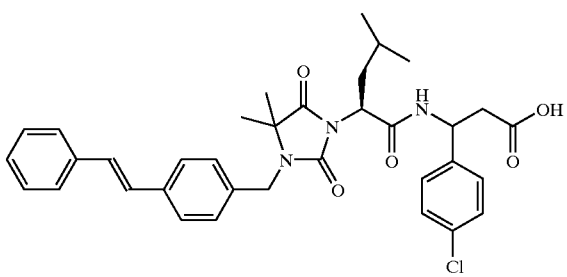

The compound was prepared according to the general preparation processes, steps A, B, D, E and J. In step J, the amino compound employed was 3-amino-3-(4-chlorophenyl)propionic acid bonded to Wang resin.

Yield: 7.9 mg

ES(+)-MS: 617.7(M+H)

Example 18

(R)-3-((S)-2-(4,4-Dimethyl-3-(4-(2-phenylethinyl)benzyl)-2,5-dioxoimidazolidin-1-yl)-2-(2-methylpropyl)acetylamino)-3-methylpropionic Acid

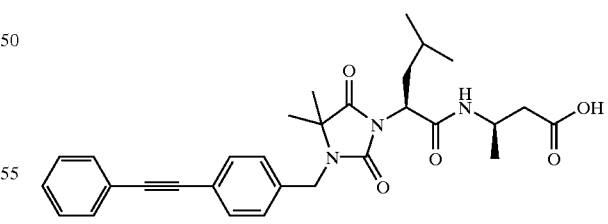

The compound was prepared according to the general preparation processes, steps A, B, F (reaction with 4-iodobenzyl bromide), N (reaction with phenylacetylene), H and J. In step J, the amino compound employed was tert-butyl (R)-3-amino-3-methylpropionate.

Yield: 15 mg

Example 19

(R)-3-((S)-2-(4,4-Dimethyl-3-(4-(2-(2-fluorophenyl)ethinyl)-benzyl)-2,5-dioxoimidazolidin-1-yl)-2-(2-methyl-propyl)acetylamino)-3-methylpropionic Acid

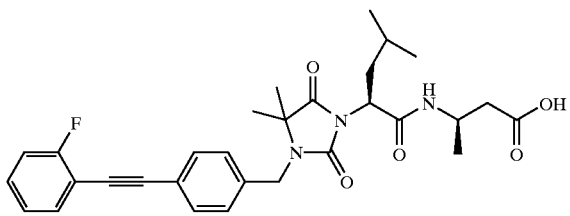

The compound was prepared according to the general preparation processes, steps A, B, F (reaction with 4-iodobenzyl bromide), N (reaction with 2-fluorophenylacetylene, H and J. In step J, the amino compound employed was tert-butyl (R)-3-amino-3-methylpropionate.

Yield: 20 mg

Investigation of the biological activity

The test method used for the activity of the compounds of the formula I on the interaction between VCAM-1 and VLA-4 is an assay which is specific for this interaction. The cellular binding components, i.e. the VLA-4 integrins, are supplied in their natural form as surface molecules on human U937 cells (ATCC CRL 1593), which belong to the leukocytes group. The specific binding components used are genetically engineered recombinant soluble fusion proteins, consisting of the extracytoplasmatic domain of human VCAM-1 and the constant region of a human immunoglobulin of the subclass IgG1.

TEST METHOD

Assay for the Measurement of the Adhesion of U937 Cells (ATCC CRL 1593) to hVCAM-1(1–3)-IgG 1. Preparation of Human VCAM-1(1–3)-IgG and Human CD4-IgG A genetic construct for the expression of the extracellular domain of human VCAM-1, associated with the genetic sequence of the heavy chain of human immunoglobulin IgGI (hinge, CH2 and CH3 regions), from Dr. Brian Seed, Massachusetts General Hospital, Boston, USA was employed (cf. Damle and Aruffo, Proc. Natl. Acad. Sci. USA 1991, 88, 6403–6407). The soluble fusion protein hVCAM-1(1–3)-IgG contained the three amino-terminal extracellular immunoglobulin-like domains of human VCAM-1 (Damle and Aruffo, Proc. Natl. Acad. Sci. USA 1991, 88, 6403–6407). CD4-IgG (Zettlmeissl et al., DNA and Cell Biology 1990, 9, 347) served as a fusion protein for negative controls. The recombinant proteins were expressed as soluble proteins after DEAE/dextran-mediated DNA transfection in COS cells (ATCC CRL1651) according to standard procedures (Ausubel et al., Current Protocols in Molecular Biology, John Wiley & Sons, Inc., 1994).

2. Assay for the Measurement of the Adhesion of U937 Cells to hVCAM-1(1–3)-IgG 2.1 96-well microtiter test plates (Nunc Maxisorb) were incubated at room temperature for 1 hour with 100 µl/well of a goat-anti-human IgG antibody solution (10 µg/ml in 50 mM tris, pH 9.5). After removal of the antibody solution, washing was carried out once with PBS.

2.2 150 µl/well of a blocking buffer (1% BSA in PBS) was incubated on the plates at room temperature for 0.5 hour. After removal of the blocking buffer, washing was carried out once with PBS.

2.3 100 µl per well of a cell culture supernatant of transfected COS cells were incubated on the plates at room temperature for 1.5 hours. The COS cells were transfected with a plasmid which codes for the three N-terminal immunoglobulin-like domains of VCAM-1, coupled to the Fc part of human IgG, (hVCAM-1(1–3)-IgG). The content of hVCAM-1(1–3)-IgG was about 0.5–1 µg/ml. After removal of the culture supernatant, washing was carried out once with PBS.

2.4 The plates were incubated at room temperature for 20 minutes with 100 µl/well of Fc receptor blocking buffer (1 mg/ml of γ-globulin, 100 mM NaCl, 100 µM $MgCl_2$, 100 µM $MnCl_2$, 100 µM $CaCl_2$, 1 mg/ml of BSA in 50 mM HEPES, pH 7.5). After removal of the Fc receptor blocking buffer, washing was carried out once with PBS.

2.5 20 µl of binding buffer (100 mM NaCl, 100 µM $MgCl_2$, 100 µM $MnCl_2$, 100 µM $CaCl_2$, 1 mg/ml of BSA in 50 mM HEPES, pH 7.5) were initially introduced, and the substances to be tested were added in 10 µl of binding buffer and incubated for 20 minutes. The controls used were antibodies against VCAM-1 (BBT, No. BBA6) and against VLA-4 (Immunotech, No. 0764).

2.6 U937 cells were incubated in Fc receptor blocking buffer for 20 minutes and then added by pipette in a concentration of $1 \times 10^6$/ml and in an amount of 100 µl per well (final volume 125 µl/well).

2.7 The plates were slowly immersed at an angle of 45° in stop buffer (100 mM NaCl, 100 µM $MgCl_2$, 100 µM $MnCl_2$, 100 µM $CaCl_2$ in 25 mM tris, pH 7.5) and shaken off. The process was repeated.

2.8 50 µl/well of a dye solution (16.7 µg/ml of Hoechst Dye 33258, 4% formaldehyde, 0.5% Triton X-100 in PBS) were then incubated on the plates for 15 minutes.

2.9 The plates were shaken off and slowly immersed at an angle of 450 in stop buffer (100 mM NaCl, 100 µM $MgCl_2$, 100 µM $MnCl_2$, 100 µM $CaCl_2$ in 25 mM tris, pH 7.5). The process was repeated. The plates with the contained liquid (stop buffer) were then measured in a cytofluorimeter (Millipore) (sensitivity: 5, filter: excitation wavelength: 360 nm, emission wavelength: 460 nm).

The intensity of the light emitted by the stained U937 cells is a measure of the number of the U937 cells adherent to the hVCAM-1(1–3)-IgG and remaining on the plate and thus a measure of the ability of the added test substance to inhibit this adhesion. From the inhibition of the adhesion at various concentrations of the test substance, the concentration $IC_{50}$ was calculated which leads to a 50% inhibition of adhesion.

The following test results were obtained:

| Compound of example | U937/VCAM-1 cell adhesion test $IC_{50}$ (µM) |
| --- | --- |
| 1 | 3.2 |
| 2 | 118.2 |
| 3 | 0.56 |
| 4 | 27.8 |
| 5 | 0.15 |
| 6 | 16.4 |
| 7 | 2.9 |
| 8 | 2.0 |
| 9 | 0.18 |
| 10 | 24.5 |
| 11 | 18.0 |

| Compound of example | U937/VCAM-1 cell adhesion test IC$_{50}$ ($\mu$M) |
|---|---|
| 12 | 17.5 |
| 13 | 64.6 |
| 14 | 15.3 |
| 15 | 61.5 |
| 16 | 34.9 |
| 17 | 36.6 |

What is claimed is:

1. A compound of the formula I,

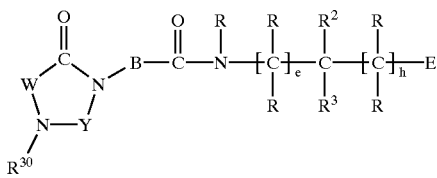

(I)

in which

W is a divalent radical $R^1$—A—$C(R^{13})$;

Y is a carbonyl group or thiocarbonyl group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl or a divalent radical of a 5-membered or 6-membered saturated or unsaturated heterocycle, which optionally contains one or two nitrogen atoms and is optionally mono- or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent radical selected from the group consisting of $(C_1-C_6)$-alkylene, $(C_2-C_6)$-alkenylene, phenylene, phenylene-$(C_1-C_3)$-alkyl, $(C_1-C_3)$-alkylenephenyl and $(C_1-C_3)$-alkylenephenyl-$(C_1-C_3)$-alkyl, where the $(C_1-C_6)$-alkylene radical and the $(C_2-C_6)$-alkenylene radical are unsubstituted or substituted by one or more identical or different radicals selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^6CO$, $R^7CO$ or $R^{10}CO$;

R is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl or heteroaryl-$(C_1-C_8)$-alkyl optionally substituted in the heteroaryl radical, where each R independently has one of the meanings indicated and all radicals R may be identical or different;

$R^1$ is hydrogen, $(C_3-C_{12})$-cycloalkyl, $(C_3-C_{12})$-cycloalkyl-$(C_1-C_8)$-alkyl, $R^2$—$((C_6-C_{14})$-aryl) optionally substituted in the aryl radical, $(R^{21}$—$((C_6-C_{14})$-aryl)-$(C_1-C_8)$-alkyl optionally substituted in the aryl radical, the radical Het-, Het-$(C_1-C_8)$-alkyl, one of the radicals X—NH—C(=NH)—$R^{20}$—, $X^1$—NH—$R^{20}$—, $R^{21}O$—$R^{20}$—, $R^{21}N(R^{21})$—$R^{20}$—, $R^{21}C(O)$—, $R^{21}O$—C(O)—, $R^{22}N(R^{21})$—C(O)—, $R^{22}C(O)$—N$(R^{21})$—, $R^{21}O$—N=, O= and S=, or $(C_1-C_{10})$-alkyl which is optionally mono- or polysubstituted by fluorine;

X is hydrogen, $(C_1-C_6)$-alkyl, $(C_1-C_6)$-alkylcarbonyl, $(C_1-C_6)$-alkoxycarbonyl, $(C_1-C_{10})$-alkylcarbonyloxy-$(C_1-C_6)$-alkoxycarbonyl, optionally substituted $(C_6-C_{14})$-arylcarbonyl, optionally substituted $(C_6-C_{14})$-aryloxycarbonyl, $(C_6-C_{14})$-aryl-$(C_1-C_6)$-alkoxycarbonyl which is optionally substituted in the aryl radical, cyano, hydroxyl, $(C_1-C_6)$-alkoxy, $(C_6-C_{14})$-aryl-$(C_1-C_6)$-alkoxy, which is optionally substituted in the aryl radical, or amino;

$X^1$ has one of the meanings of X or is R'—NH—C(=N—R''), where R' and R'' independently of one another have the meanings of X;

$R^2$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical or $(C_3-C_8)$-cycloalkyl;

$R^3$ is hydrogen, $(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, $(C_3-C_8)$-cycloalkyl, $(C_3-C_8)$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, $(C_2-C_8)$-alkenyl, $(C_2-C_8)$-alkynyl, $R^{11}NH$, $CON(CH_3)R^4$, $CONHR^4$, $COOR^{21}$, $COOR^{15}$, $CON(CH_3)R^{15}$ or $CONHR^{15}$;

$R^4$ is hydrogen or $(C_1-C_{10})$-alkyl which is unsubstituted or mono- or polysubstituted by identical or different radicals selected from the group consisting of hydroxyl, $(C_1-C_8)$-alkoxy, $R^5$, optionally substituted $(C_3-C_8)$-cycloalkyl, hydroxycarbonyl, aminocarbonyl, mono- or di-$((C_1-C_{18})$-alkyl)aminocarbonyl, $(C_6-C_{14})$-aryl-$(C_1-C_8)$-alkoxycarbonyl which is optionally substituted in the aryl radical, $(C_1-C_8)$-alkoxycarbonyl, $R^6$—CO, $R^7CO$, tetrazolyl and trifluoromethyl;

$R^5$ is optionally substituted $(C_6-C_{14})$-aryl, $(C_6-C_{14})$-aryl-$(C_1-C_8)$-alkyl optionally substituted in the aryl radical, or a radical of an optionally substituted monocyclic or bicyclic, 5-membered to 12-membered heterocyclic ring which may be aromatic, partially saturated or completely saturated and which contains one, two or three identical or different heteroatoms selected from the group consisting of nitrogen, oxygen and sulfur;

$R^6$ is the radical of a natural or unnatural amino acid, imino acid, optionally N—$(C_1-C_8)$-alkylated or N—$((C_6-C_{14})$-aryl-$(C_1-C_8)$-alkylated) azaamino acid which is optionally substituted in the aryl radical, or the radical of a dipeptide, tripeptide, or tetrapeptide, and their esters and amides, where free functional groups may be protected by protective groups customary in peptide chemistry and where the nitrogen atoms in the amide bonds in the group $R^6$—CO optionally carry a radical R as a substituent;

$R^7$ is the radical of a 5-membered to 10-membered, saturated monocyclic or polycyclic heterocycle bonded via a nitrogen atom, which optionally may contain one, two, three or four identical or different additional ring heteroatoms selected from the group consisting of oxygen, nitrogen and sulfur and which is optionally substituted on carbon atoms and on additional ring nitrogen atoms, where additional ring nitrogen atoms optionally may carry identical or different radicals selected from the group consisting of hydrogen, $R^h$, HCO, $R^hCO$, $R^hO-CO$, $HO-CO-(C_1-C_4)$-alkyl and $R^hO-CO-(C_1-C_4)$-alkyl as substituents and $R^h$ is $(C_1-C_8)$-alkyl, $(C_3-C_8)$-cycloalkyl, $(C_3-C_8)$-cycloalkyl-$(C_1-C_8)$-alkyl, optionally substituted $(C_6-C_{14})$-aryl or $(C_6-C_{14})$-aryl-$(C_1-C_8)$-alkyl optionally substituted in the aryl radical;

$R^8$ is hydrogen, $(C_1-C_{10})$-alkyl, optionally substituted $(C_6-C_{14})$-aryl or $(C_6-C_{14})$-aryl-$(C_1-C_8)$-alkyl which is optionally substituted in the aryl radical, where the radicals $R^8$ are independent of one another;

$R^9$ is hydrogen, aminocarbonyl, $(C_1-C_{10})$-alkylaminocarbonyl, $(C_3-C_8)$-cycloalkylaminocarbonyl, optionally substituted $(C_6-C_{14})$-arylaminocarbonyl, $(C_1-C_{10})$-alkyl, optionally substituted $(C_6-C_{14})$-aryl or $(C_3-C_8)$-cycloalkyl;

$R^{10}$ is hydroxyl, $(C_1-C_{10})$-alkoxy, $(C_6-C_{14})$-aryl-$(C_1-C_8)$-alkoxy which is optionally substituted in the aryl radical, optionally substituted $(C_6-C_{14})$-aryloxy, $(C_1-C_8)$-alkylcarbonyloxy-$(C_1-C_6)$-alkoxy, $(C_6-C_{14})$-arylcarbonyloxy-$(C_1-C_6)$-alkoxy optionally substituted in the aryl radical, amino or mono- or di-$((C_1-C_{10})$-alkyl)amino;

$R^{11}$ is hydrogen, $R^{12a}$, $R^{12a}-CO$, $H-CO$, $R^{12a}-O-CO$, $R^{12b}-CO$, $R^{12b}-CS$, $R^{12a}-S(O)_2$ or $R^{12b}-S(O)_2$;

$R^{12a}$ is $(C_1-C_{10})$-alkyl, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{12b}$ is amino, di-$((C_1-C_{10})$-alkyl)amino or $R^{12a}-NH$;

$R^{13}$ is hydrogen, optionally substituted $(C_6-C_{14})$-aryl, $(C_6-C_{14})$-aryl-$(C_1-C_6)$-alkyl optionally substituted in the aryl radical, $(C_3-C_8)$-cycloalkyl, $(C_3-C_8)$-cycloalkyl-$(C_1-C_6)$-alkyl or $(C_1-C_6)$-alkyl which is optionally mono- or polysubstituted by fluorine;

$R^{15}$ is $R^{16}-(C_1-C_6)$-alkyl or $R^{16}$;

$R^{16}$ is a radical of a 6-membered to 24-membered bicyclic or tricyclic ring which is saturated or partially unsaturated and which optionally may contain one, two, three or four identical or different heteroatoms selected from the group consisting of nitrogen, oxygen and sulfur and which is optionally substituted by one or more identical or different substituents selected from the group consisting of $(C_1-C_4)$-alkyl and oxo;

$R^{20}$ is a direct bond or a divalent $(C_1-C_6)$-alkylene radical;

$R^{21}$ is hydrogen, $(C_1-C_8)$-alkyl, $(C_3-C_{12})$-cycloalkyl, $(C_3-C_{12})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, the radical Het- or Het-$(C_1-C_8)$-alkyl, where alkyl radicals are optionally mono- or polysubstituted by fluorine and the radicals $R^{21}$ are independent of one another if they occur more than once and may be identical or different;

$R^{22}$ is $R^{21}-$, $R^{21}-O-$, $R^{21}N(R^{21})-$, $R^{21}C(O)-$, $R^{21}O-C(O)-$, $R^{21}N(R^{21})-C(O)-$, $R^{21}N(R^{21})-C(=N(R^{21}))-$ or $R^{21}C(O)-N(R^{21})-$;

$R^{30}$ is one of the radicals $R^{32}-CR=CR-R^{31}-$ or $R^{32}-C\equiv C-R^{31}-$, where the radicals R independently of one another have one of the meanings indicated and may be identical or different;

$R^{31}$ is the divalent radical $-R^{33}-R^{34}-R^{35}-R^{36}-$, where $R^{36}$ is bonded to the nitrogen atom in the imidazolidine ring in the formula I;

$R^{32}$ is hydrogen, $(C_2-C_8)$-alkenyl, $(C_2-C_8)$-alkynyl, $(C_3-C_{12})$-cycloalkyl, $(C_3-C_{12})$-cycloalkyl-$(C_1-C_8)$-alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical or $(C_1-C_8)$-alkyl which are optionally substituted by 1 to 8 fluorine atoms;

$R^{33}$ is a direct bond or a divalent $(C_1-C_6)$-alkylene radical;

$R^{34}$ is a divalent radical selected from the group consisting of $(C_3-C_{12})$-cycloalkylene, $(C_6-C_{12})$-bicycloalkylene, $(C_6-C_{12})$-tricycloalkylene, optionally substituted $(C_6-C_{14})$-arylene and optionally substituted heteroarylene;

$R^{35}$ is a direct bond or a divalent $(C_1-C_8)$-alkylene radical;

$R^{36}$ is a direct bond, the group $-CO-$ or the group $-S(O)_n-$,

Het is a radical of a monocyclic or polycyclic, 4-membered to 14-membered, aromatic or nonaromatic ring, which contains 1, 2, 3 or 4 identical or different heteroatoms selected from the group consisting of N, O and S as ring members and is optionally substituted by one or more, identical or different substituents;

e and h independently of one another are 0 or 1 and may be identical or different;

n is 1 or 2;

in all its stereoisomeric forms and mixtures thereof in all ratios, or its physiologically tolerable salts.

2. A compound of the formula I as claimed in claim 1, in which

W is a divalent radical $R^1-A-C(R^{13})$;

Y is a carbonyl group or thiocarbonyl group;

A is a direct bond, one of the divalent radicals $(C_1-C_6)$-alkylene, $(C_3-C_7)$-cycloalkylene, phenylene, phenylene-$(C_1-C_6)$-alkyl, phenylene-$(C_2-C_6)$-alkenyl or a divalent radical of a 5-membered or 6-membered saturated or unsaturated heterocycle which optionally contains one or two nitrogen atoms and is optionally monosubstituted or disubstituted by $(C_1-C_6)$-alkyl or doubly bonded oxygen or sulfur, where in the radicals phenylenealkyl and phenylenealkenyl the radical $R^1$ is bonded to the phenylene group;

B is a divalent methylene radical or ethylene radical, where the methylene radical and the ethylene radical are unsubstituted or are substituted by one or more identical or different radicals selected from the group consisting of $(C_1-C_8)$-alkyl, $(C_2-C_8)$-alkenyl, $(C_2-C_8)$-alkynyl, $(C_3-C_{10})$-cycloalkyl, $(C_3-C_{10})$-cycloalkyl-$(C_1-C_6)$-alkyl, optionally substituted $(C_6-C_{14})$-aryl, $(C_6-C_{14})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^6CO$, $R^7CO$ or $R^{10}CO$;

R is hydrogen, $(C_1-C_8)$-alkyl, $(C_3-C_{10})$-cycloalkyl, $(C_3-C_{10})$-cycloalkyl-$(C_1-C_6)$-alkyl, optionally substituted $(C_6-C_{10})$-aryl, $(C_6-C_{10})$-aryl-$(C_1-C_8)$-alkyl optionally substituted in the aryl radical, optionally substituted heteroaryl or heteroaryl-($C_1$–$C_6$)-alkyl optionally substituted in the heteroaryl radical, where each R independently has one of the meanings indicated and all radicals R may be identical or different;

$R^1$ is hydrogen, ($C_5$–$C_{10}$)-cycloalkyl, ($C_5$–$C_{10}$)-cycloalkyl-($C_1$–$C_6$)-alkyl, $R^{21}$—(($C_6$–$C_{14}$)-aryl) optionally substituted in the aryl radical, ($R^{21}$—(($C_6$–$C_{14}$)-aryl))-($C_1$–$C_8$)-alkyl optionally substituted in the aryl radical, the radical Het-, Het-($C_1$–$C_8$)-alkyl, one of the radicals X—NH—C(=NH)—$R^{20}$—, $X^1$—NH—$R^{20}$—, $R^{21}$O—$R^{20}$—, $R^{22}$C(O)—N($R^{21}$), $R^{22}$N($R^{21}$)-C(O)—, $R^{21}$O—N=, O= and S=, or ($C_1$–$C_{10}$)-alkyl which are optionally monosubstituted or polysubstituted by fluorine;

X is hydrogen, ($C_1$–$C_6$)-alkyl, ($C_1$–$C_6$)-alkylcarbonyl, ($C_1$–$C_6$)-alkoxycarbonyl, ($C_1$–$C_{10}$)-alkylcarbonyloxy-($C_1$–$C_6$)-alkoxycarbonyl, optionally substituted ($C_6$–$C_{14}$)-arylcarbonyl, optionally substituted ($C_6$-$C_{14}$)-aryloxycarbonyl, ($C_6$–$C_{14}$)-aryl-($C_1$–$C_6$)-alkoxycarbonyl which is optionally substituted in the aryl radical, hydroxyl, ($C_1$–$C_6$)-alkoxy, ($C_6$–$C_{14}$)-aryl-($C_1$–$C_6$)-alkoxy which is optionally substituted in the aryl radical, or amino;

$X^1$ has one of the meanings of X or is $R^1$—NH—C(=N—R"), where R' and R" independently of one another have the meanings of X;

$R^2$ is hydrogen, ($C_1$–$C_8$)-alkyl, optionally substituted ($C_6$–$C_{10}$)-aryl or ($C_6$–$C_{10}$)-aryl-($C_1$–$C_8$)-alkyl optionally substituted in the aryl radical;

$R^3$ is hydrogen, ($C_1$–$C_8$)-alkyl, optionally substituted ($C_6$–$C_{14}$)-aryl, ($C_6$–$C_{14}$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, ($C_3$–$C_8$)-cycloalkyl, ($C_3$–$C_8$)-cycloalkyl-($C_1$–$C_8$)-alkyl, ($C_6$–$C_{12}$)-bicycloalkyl, ($C_6$–$C_{12}$)-bicycloalkyl-($C_1$–$C_8$)-alkyl, ($C_6$–$C_{12}$)-tricycloalkyl, ($C_6$–$C_{12}$)-tricycloalkyl-($C_1$–$C_8$)-alkyl, ($C_2$–$C_8$)-alkenyl, ($C_2$–$C_8$)-alkynyl, $R^{11}$NH, COOR$^{21}$CON(CH$_3$)$R^4$, CONHR$^4$, COOR$^{15}$, CON(CH$_3$)$R^{15}$ or CONHR$^{15}$;

$R^4$ is hydrogen or ($C_1$–$C_8$)-alkyl which is unsubstituted or is monosubstituted or polysubstituted by identical or different radicals selected from the group consisting of hydroxyl, ($C_1$–$C_8$)-alkoxy, $R^5$, optionally substituted ($C_3$–$C_8$)-cycloalkyl, hydroxycarbonyl, aminocarbonyl, mono- or di-(($C_1$–$C_{10}$)-alkyl)aminocarbonyl, ($C_6$–$C_{14}$)-aryl-($C_1$–$C_8$)-alkoxycarbonyl which is optionally substituted in the aryl radical, ($C_1$–$C_8$)-alkoxycarbonyl, $R^6$—CO, $R^7$—CO, tetrazolyl and trifluoromethyl;

$R^5$ is optionally substituted ($C_6$–$C_{14}$)-aryl, ($C_6$–$C_{14}$)-aryl-($C_1$–$C_8$)-alkyl optionally substituted in the aryl radical or a radical of an optionally substituted monocyclic or bicyclic, 5-membered to 12-membered heterocyclic ring, which may be aromatic, partially saturated or completely saturated and which contains one, two or three identical or different heteroatoms selected from the group consisting of nitrogen, oxygen and sulfur;

$R^6$ is the radical of a natural or unnatural amino acid, imino acid, optionally N—($C_1$–$C_8$)-alkylated or N—(($C_6$–$C_{14}$)-aryl-($C_1$–$C_8$)-alkylated) azaamino acid which is optionally substituted in the aryl radical, or the radical of a dipeptide, tripeptide or tetrapeptide, as well as their esters and amides, where free functional groups may be protected by protective groups customary in peptide chemistry and where the nitrogen atoms in the amide bonds in the group $R^6$—CO optionally carry a radical R as a substituent;

$R^7$ is the radical of a 5-membered to 10-membered, saturated monocyclic or polycyclic heterocycle bonded via a nitrogen atom, which optionally may contain one, two, three or four identical or different additional ring heteroatoms selected from the group consisting of oxygen, nitrogen and sulfur and which is optionally substituted on carbon atoms and on additional ring nitrogen atoms, where additional ring nitrogen atoms optionally carry identical or different radicals selected from the group consisting of hydrogen, $R^h$, HCO, $R^h$CO, $R^h$O—CO, HO—CO—($C_1$–$C_4$)-alkyl and $R^h$O—CO—($C_1$–$C_4$)-alkyl as substituents and $R^h$ is ($C_1$–$C_8$)-alkyl, ($C_3$–$C_8$)-cycloalkyl, ($C_3$–$C_8$)-cycloalkyl-($C_1$–$C_8$)-alkyl, optionally substituted ($C_6$–$C_{14}$)-aryl or ($C_6$–$C_{14}$)-aryl-($C_1$–$C_8$)-alkyl optionally substituted in the aryl radical;

$R^{10}$ is hydroxyl, ($C_1$–$C_{10}$)-alkoxy, ($C_6$–$C_{14}$)-aryl-($C_1$–$C_8$)-alkoxy which is optionally substituted in the aryl radical, optionally substituted ($C_6$–$C_{14}$)-aryloxy, ($C_1$–$C_8$)-alkylcarbonyloxy-($C_1$–$C_6$)-alkoxy, ($C_6$–$C_{14}$)-arylcarbonyloxy-($C_1$–$C_6$)-alkoxy optionally substituted in the aryl radical, amino or mono- or di-(($C_1$–$C_{10}$)-alkyl)amino;

$R^{11}$ is hydrogen, $R^{12a}$, $R^{12a}$—CO $R^{12a}$—O—CO, $R^{12b}$—CO, $R^{12b}$—CS or $R^{12a}$—S(O)$_2$;

$R^{12a}$ is ($C_1$–$C_{10}$)-alkyl, ($C_2$–$C_8$)-alkenyl, ($C_2$–$C_8$)-alkynyl, ($C_5$–$C_{10}$)-cycloalkyl, ($C_5$–$C_{10}$)-cycloalkyl-($C_1$–$C_8$)-alkyl, optionally substituted ($C_6$–$C_4$)-aryl, ($C_6$–$C_4$)-aryl-($C_1$–$C_8$)-alkyl optionally substituted in the aryl radical, optionally substituted heteroaryl, heteroaryl-($C_1$–$C_8$)-alkyl optionally substituted in the heteroaryl radical, or the radical $R^{12b}$ is amino, di-(($C_1$–$C_{10}$)-alkyl)amino or $R^{12a}$—NH;

$R^{13}$ is hydrogen or ($C_1$–$C_6$)-alkyl;

$R^{15}$ is $R^{16}$—($C_1$–$C_6$)-alkyl or $R^{16}$;

$R^{16}$ is a radical of a 6-membered to 14-membered bicyclic or tricyclic ring which is saturated or partially unsaturated and which optionally may contain one, two, three or four identical or different heteroatoms selected from the group consisting of nitrogen, oxygen and sulfur and which is optionally substituted by one or more identical or different substituents selected from the group consisting of ($C_1$–$C_4$)-alkyl and oxo;

$R^{20}$ is a direct bond or ($C_1$–$C_4$)-alkylene;

$R^{20}$ is hydrogen, ($C_1$–$C_8$)-alkyl, ($C_5$–$C_{10}$)-cycloalkyl, ($C_5$–$C_{10}$)-cycloalkyl-($C_1$–$C_6$)-alkyl, optionally substituted ($C_6$–$C_{10}$)-aryl, ($C_6$–$C_{14}$)-aryl-($C_1$–$C_6$)-alkyl optionally substituted in the aryl radical, the radical Het- or Het-($C_1$–$C_6$)-alkyl, where alkyl radicals may be monosubstituted or polysubstituted by fluorine and the radicals $R^{21}$, if they occur a number of times, may be identical or different;

$R^{22}$ is one of the radicals $R^{21}$—, $R^{21}$N($R^{21}$)—, $R^{21}$C(O)—, $R^{21}$O—C(O)—or $R^{21}$N($R^{21}$)—C(=N($R^{21}$))—;

$R^{30}$ is one of the radicals $R^{32}$—CR=CR—$R^{31}$— or $R^{32}$—C≡C—$R^{31}$—, where the radicals R independently of one another have one of the meanings indicated and may be identical or different;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, ($C_2$–$C_8$)-alkenyl, ($C_2$–$C_8$)-alkynyl, ($C_3$–$C_2$)-cycloalkyl, ($C_3$–$C_{12}$)-cycloalkyl-($C_1$–$C_8$)- alkyl, $(C_6-C_{12})$-bicycloalkyl, $(C_6-C_{12})$-bicycloalkyl-$(C_1-C_8)$-alkyl, $(C_6-C_{12})$-tricycloalkyl, $(C_6-C_{12})$-tricycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical or $(C_1-C_8)$-alkyl which is optionally substituted by 1 to 8 fluorine atoms;

$R^{33}$ is a direct bond or a divalent $(C_1-C_6)$-alkylene radical;

$R^{34}$ is a divalent radical selected from the group consisting of $(C_5-C_{10})$-cycloalkylene, $(C_6-C_{12})$-bicycloalkylene, optionally substituted $(C_6-C_{14})$-arylene and optionally substituted heteroarylene;

$R^{35}$ is a direct bond or a divalent $(C_1-C_8)$-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring, which contains 1, 2, 3 or 4 identical or different heteroatoms selected from the group consisting of N and O as rings members and is optionally substituted by one or more, identical or different substituents;

e and h independently of one another are 0 or 1 and may be identical or different;

n is 1 or 2;

in all its stereoisomeric forms and mixtures thereof in all ratios, or its physiologically tolerable salts.

3. A compound of the formula I as claimed in claim 2, in which

W is a divalent radical $R^1$—A—C($R^{13}$);

Y is a carbonyl group or thiocarbonyl group;

A is a direct bond, one of the divalent radicals $(C_1-C_6)$-alkylene, $(C_5-C_6)$-cycloalkylene, phenylene, phenylene-$(C_1-C_4)$-alkyl or a divalent radical of a 5-membered or 6-membered saturated or unsaturated heterocycle which optionally may contain one or two nitrogen atoms and may be monosubstituted or disubstituted by $(C_1-C_6)$-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or are substituted by one or two identical or different radicals selected from the group consisting of $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^{10}$CO;

R is hydrogen or $(C_1-C_8)$-alkyl where each R independently has one of the meanings indicated and all radicals R may be identical or different;

$R^1$ is hydrogen, $R^{21}$—(($C_6-C_{10})$-aryl) optionally substituted in the aryl radical, ($R^{21}$—(($C_6-C_{10})$-aryl))-$(C_1-C_6)$-alkyl optionally substituted in the aryl radical, the radical Het-, Het-$(C_1-C_6)$-alkyl, one of the radicals X—NH—C(=NH)—$R^{20}$—, $X^1$—NH—$R^{20}$—, $R^{22}$N($R^{21}$)—C(O)—, O= and S=, or $(C_1-C_{10})$-alkyl which is optionally monosubstituted or polysubstituted by fluorine;

X is hydrogen, $(C_1-C_6)$-alkyl, $(C_1-C_6)$-alkylcarbonyl, $(C_1-C_6)$-alkoxycarbonyl, $(C_1-C_8)$-alkylcarbonyloxy-$(C_1-C_6)$-alkoxycarbonyl, optionally substituted $(C_6-C_{10})$-arylcarbonyl, optionally substituted $(C_6-C_{10})$-aryloxycarbonyl, $(C_6-C_{14})$-aryl-$(C_1-C_6)$-alkoxycarbonyl which is optionally substituted in the aryl radical, hydroxyl, $(C_1-C_6)$-alkoxy or amino;

$X^1$ has one of the meanings of X or is R'—NH—C(=N—R"), where R' and R" independently of one another have the meanings of X;

$R^2$ is hydrogen or $(C_1-C_8)$-alkyl;

$R^3$ is hydrogen, $(C_1-C_8)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl, heteroaryl-$(C_1-C_6)$-alkyl optionally substituted in the heteroaryl radical, $(C_3-C_8)$-cycloalkyl, $(C_3-C_8)$-cycloalkyl-$(C_1-C_6)$-alkyl, $(C_6-C_{12})$-bicycloalkyl, $(C_6-C_{12})$-bicycloalkyl-$(C_1-C_6)$-alkyl, $(C_6-C_{12})$-tricycloalkyl, $(C_6-C_{12})$-tricycloalkyl-$(C_1-C_6)$-alkyl, $(C_2-C_8)$-alkenyl, $(C_2-C_8)$-alkynyl, $R^{11}$NH, COOR$^{21}$, CON(CH$_3$)R$^4$, CONHR$^4$, CON(CH$_3$)R$^{15}$ or CONHR$^{15}$;

$R^4$ is $(C_1-C_8)$-alkyl which is unsubstituted or is monosubstituted or polysubstituted by identical or different radicals selected from the group consisting of hydroxyl, $(C_1-C_8)$-alkoxy, $R^5$, optionally substituted $(C_3-C_8)$-cycloalkyl, hydroxycarbonyl, aminocarbonyl, $(C_6-C_{10})$-aryl-$(C_1-C_4)$-alkoxycarbonyl which is optionally substituted in the aryl radical, $(C_1-C_6)$-alkoxycarbonyl, $R^6$—CO, $R^7$—CO, tetrazolyl and trifluoromethyl;

$R^5$ is optionally substituted $(C_6-C_{12})$-aryl, $(C_6-C_{12})$-aryl-$(C_1-C_8)$-alkyl optionally substituted in the aryl radical or a radical of an optionally substituted monocyclic or bicyclic 5-membered to 12-membered heterocyclic ring which may be aromatic, partially saturated or completely saturated and which contains one, two or three identical or different heteroatoms selected from the group consisting of nitrogen, oxygen and sulfur;

$R^6$ is the radical of a natural or unnatural amino acid, imino acid, optionally N—$(C_1-C_8)$-alkylated or N—(($C_6-C_{12})$-aryl-$(C_1-C_8)$-alkylated) azaamino acid which is optionally substituted in the aryl radical, or the radical of a dipeptide or tripeptide, as well as their esters and amides, where free functional groups may be protected by protective groups customary in peptide chemistry and where the nitrogen atoms in the amide bonds in the group $R^6$—CO may carry a radical R as a substituent;

$R^7$ is the radical of a 5-membered to 7-membered, saturated monocyclic or bicyclic heterocycle bonded via a nitrogen atom, which optionally may contain one, two, three or four identical or different additional ring heteroatoms selected from the group consisting of oxygen, nitrogen and sulfur and which is optionally substituted on carbon atoms and on additional ring nitrogen atoms, where additional ring nitrogen atoms optionally carry identical or different radicals selected from the group consisting of hydrogen, $R^h$, HCO, $R^h$CO, $R^h$O—CO, HO—CO—$(C_1-C_4)$-alkyl and $R^h$O—CO—$(C_1-C_4)$-alkyl as substituents and $R^h$ is $(C_1-C_6)$-alkyl, $(C_3-C_8)$-cycloalkyl, $(C_3-C_8)$-cycloalkyl-$(C_1-C_8)$-alkyl, optionally substituted $(C_6-C_{10})$-aryl or $(C_6-C_{10})$-aryl-$(C_1-C_4)$-alkyl optionally substituted in the aryl radical;

$R^{10}$ is hydroxyl, $(C_1-C_8)$-alkoxy, $(C_6-C_{10})$-aryl-$(C_1-C_6)$-alkoxy which is optionally substituted in the aryl radical, optionally substituted $(C_6-C_{10})$-aryloxy, $(C_1-C_8)$-alkylcarbonyloxy-$(C_1-C_4)$-alkoxy, $(C_6-C_{10})$-arylcarbonyloxy-$(C_1-C_4)$-alkoxy optionally substituted in the aryl radical, amino or mono- or di-$((C_1-C_8)$-alkyl)amino;

$R^{11}$ is hydrogen, $R^{12a}$, $R^{12a}$—CO, $R^{12a}$—O—CO $R^{12b}$CO or $R^{12a}$—S(O)$_2$;

$R^{12a}$ is $(C_1-C_{10})$-alkyl, $(C_2-C_8)$-alkenyl, $(C_2-C_8)$-alkynyl, $(C_5-C_{10})$-cycloalkyl, $(C_5-C_{10})$-cycloalkyl-$(C_1-C_8)$-alkyl, optionally substituted $(C_6-C_{14})$-aryl, $(C_6-C_{14})$-aryl-$(C_1-C_8)$-alkyl optionally substituted in the aryl radical, optionally substituted heteroaryl, heteroaryl-$(C_1-C_8)$-alkyl optionally substituted in the heteroaryl radical, or the radical $R^{15}$;

$R^{12b}$ is amino, di-$((C_1-C_{10})$-alkyl)amino or $R^{12a}$—NH;

$R^{13}$ is hydrogen or $(C_1-C_6)$-alkyl;

$R^{15}$ is $R^{16}$—$(C_1-C_6)$-alkyl or $R^{16}$;

$R^{16}$ is a radical of a 6-membered to 14-membered bicyclic or tricyclic radical which is saturated or partially unsaturated and which optionally may also contain one, two, three or four identical or different heteroatoms selected from the group consisting of nitrogen, oxygen and sulfur and which is optionally substituted by one or more identical or different substituents selected from the group consisting of $(C_1-C_4)$-alkyl and oxo;

$R^{20}$ is a direct bond or $(C_1-C_2)$-alkylene;

$R^{21}$ is hydrogen, $(C_1-C_6)$-alkyl, $(C_5-C_6)$-cycloalkyl, $(C_5-C_6)$-cycloalkyl-$(C_1-C_4)$-alkyl, optionally substituted $(C_6-C_{10})$-aryl, $(C_6-C_{10})$-aryl-$(C_1-C_4)$-alkyl optionally substituted in the aryl radical, the radical Het- or Het-$(C_1-C_4)$-alkyl, where alkyl radicals may be monosubstituted or polysubstituted by fluorine and the radicals $R^{21}$, if they occur a number of times, may be identical or different;

$R^{22}$ is one of the radicals $R^{21}$—, $R^{21}N(R^{21})$— or $R^{21}N(R^{21})$—C(=N($R^{21}$))—;

$R^{30}$ is one of the radicals $R^{32}$—CR=CR—$R^{31}$— or $R^{32}$—C≡C—$R^{31}$—, where the radicals R independently of one another have one of the meanings indicated and may be identical or different;

$R^{31}$ is the divalent radical —$R^{33}$—$R^{34}$—$R^{35}$—$R^{36}$—, where $R^{36}$ is bonded to the nitrogen atom in the imidazolidine ring in the formula I;

$R^{32}$ is hydrogen, $(C_2-C_6)$-alkenyl, $(C_2-C_6)$-alkynyl, $(C_5-C_6)$-cycloalkyl, $(C_5-C_6)$-cycloalky $(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl, heteroaryl-$(C_1-C_6)$-alkyl optionally substituted in the heteroaryl radical or $(C_1-C_6)$-alkyl which is optionally substituted by 1 to 6 fluorine atoms;

$R^{33}$ is a direct bond or a divalent $(C_1-C_4)$-alkylene radical;

$R^{34}$ is a divalent radical selected from the group consisting of $(C_5-C_6)$-cycloalkylene, optionally substituted $(C_6-C_{10})$-arylene and optionally substituted heteroarylene;

$R^{35}$ is a direct bond or a divalent $(C_1-C_6)$-alkylene radical;

$R^{36}$ is a direct bond, the group —CO— or the group —S(O)$_n$—;

Het is a radical of a monocyclic or polycyclic, 5-membered to 12-membered, aromatic or nonaromatic ring which contains 1 or 2 identical or different heteroatoms selected from the group consisting of N and O as ring members and is optionally substituted by one or more, identical or different substituents;

e and h independently of one another are 0 or 1 and may be identical or different;

n is 1 or 2;

in all its stereoisomeric forms and mixtures thereof in all ratios, or its physiologically tolerable salts.

4. A compound of the formula I as claimed in claim 3, in which

W is the divalent radical $R^1$—A—C($R^{13}$);

Y is a carbonyl group;

A is a direct bond, one of the divalent radicals $(C_1-C_6)$-alkylene, phenylene, phenylene-$(C_1-C_2)$-alkyl or a divalent radical of a 5-membered or 6-membered saturated or unsaturated heterocycle which optionally may contain one or two nitrogen atoms and is optionally monosubstituted or disubstituted by $(C_1-C_6)$-alkyl or doubly bonded oxygen or sulfur, where in the radical phenylenealkyl the radical $R^1$ is bonded to the phenylene group;

B is a divalent methylene radical or ethylene radical, where the methylene radical and the ethylene radical are unsubstituted or are substituted by a radical selected from the group consisting of $(C_1-C_8)$-alkyl, $(C_2-C_8)$-alkenyl, $(C_2-C_8)$-alkynyl, $(C_3-C_6)$-cycloalkyl, $(C_3-C_6)$-cycloalkyl-$(C_1-C_6)$-alkyl, optionally substituted $(C_6-C_{10})$-aryl, $(C_6-C_{10})$-aryl-$(C_1-C_6)$-alkyl optionally substituted in the aryl radical, optionally substituted heteroaryl and heteroaryl-$(C_1-C_6)$-alkyl optionally substituted in the heteroaryl radical;

E is $R^{10}$CO;

R is hydrogen or $(C_1-C_8)$-alkyl where each R independently has one of the meanings indicated and all radicals R may be identical or different;

$R^1$ is hydrogen, $R^{21}$—$((C_6-C_{10})$-aryl) optionally substituted in the aryl radical, $(R^{21}$-$((C_6-C_{10})$-aryl))-$(C_1-C_6)$-alkyl optionally substituted in the aryl radical, the radical Het-, Het-$(C_1-C_4)$-alkyl, one of the radicals X—NH—C(=NH)—$R^{20}$—, $X^1$—NH—$R^{20}$— and O=, or $(C_1-C_{10})$-alkyl which is optionally monosubstituted or polysubstituted by fluorine;

X is hydrogen, $(C_1-C_6)$-alkyl, $(C_1-C_6)$-alkylcarbonyl, $(C_1-C_6)$-alkoxycarbonyl, $(C_1-C_6)$-alkylcarbonyloxy-$(C_1-C_6)$-alkoxycarbonyl, optionally substituted $(C_6-C_{10})$-arylcarbonyl, optionally substituted $(C_6-C_{10})$-aryloxycarbonyl, $(C_6-C_{14})$-aryl-$(C_1-C_6)$-alkoxycarbonyl which is optionally substituted in the aryl radical, hydroxyl, $(C_1-C_6)$-alkoxy or amino;

$X^1$ has one of the meanings of X or is R'—NH—C(=N—R"), where R' and R" independently of one another have the meanings of X;

$R^2$ is hydrogen or $(C_1-C_6)$-alkyl;

$R^3$ is hydrogen, $(C_1-C_8)$-alkyl, optionally substituted $(C_6-C_{10})$-aryl, $(C_6-C_{10})$-aryl-$(C_1-C_4)$-alkyl optionally substituted in the aryl radical, optionally substituted heteroaryl, heteroaryl-$(C_1-C_4)$-alkyl optionally substituted in the heteroaryl radical, $(C_3-C_8)$-cycloalkyl, $(C_3-C_8)$-cycloalkyl-$(C_1-C_4)$-alkyl, $(C_6-C_{12})$-bicycloalkyl, $(C_6-C_{12})$-bicycloalkyl-$(C_1-C_4)$-alkyl, $(C_6-C_12)$-tricycloalkyl, $(C_6-C_{12})$-tricycloalkyl-$(C_1-C_4)$-alkyl, $(C_2-C_8)$-alkenyl, $(C_2-C_8)$-alkynyl, $R^{11}$NH, COOR$^{21}$, CON(CH$_3$)R$^4$, CONHR$^4$, CON(CH$_3$)R$^{15}$ or CONHR$^{15}$;

$R^4$ is $(C_1-C_6)$-alkyl which is unsubstituted or is mono- or disubstituted by identical or different radicals selected from the group consisting of hydroxyl, $(C_1–C_8)$-alkoxy, $R^5$, optionally substituted $(C_3–C_8)$-cycloalkyl, hydroxycarbonyl, aminocarbonyl, $(C_6–C_{10})$-aryl-$(C_1–C_4)$-alkoxycarbonyl which is optionally substituted in the aryl radical, $(C_1–C_6)$-alkoxycarbonyl, $R^6$—CO, $R^7$—CO, tetrazolyl and trifluoromethyl;

$R^5$ is optionally substituted $(C_6–C_{10})$-aryl, $(C_6–C_{10})$-aryl-$(C_1–C_4)$-alkyl optionally substituted in the aryl radical or a radical of an optionally substituted monocyclic or bicyclic 5-membered to 12-membered heterocyclic ring which may be aromatic, partially saturated or completely saturated and which contains one, two or three identical or different heteroatoms selected from the group consisting of nitrogen, oxygen and sulfur;

$R^6$ is a radical of a natural or unnatural amino acid or the radical of a dipeptide or tripeptide, as well as their esters and amides, where free functional groups may be protected by protective groups customary in peptide chemistry and where the nitrogen atoms in the amide bonds in the group $R^6$—CO optionally carry a radical R as a substituent;

$R^7$ is the radical of a 5-membered to 7-membered, saturated monocyclic heterocycle bonded via a nitrogen atom, which optionally contain one or two identical or different additional ring heteroatoms selected from the group consisting of oxygen, nitrogen and sulfur and which is optionally substituted on carbon atoms and on additional ring nitrogen atoms, where additional ring nitrogen atoms optionally carry identical or different radicals selected from the group consisting of hydrogen, $R^h$, HCO, $R^hCO$, $R^hO$—CO, HO—CO—$(C_1–C_4)$-alkyl and $R^hO$—CO—$(C_1–C_4)$-alkyl as substituents and $R^h$ is $(C_1–C_4)$-alkyl, optionally substituted $(C_6–C_{10})$-aryl or $(C_6–C_{10})$-aryl-$(C_1–C_4)$-alkyl optionally substituted in the aryl radical;

$R^{10}$ is hydroxyl, $(C_1–C_6)$-alkoxy, $(C_6–C_{10})$-aryl-$(C_1–C_4)$-alkoxy which is optionally substituted in the aryl radical, optionally substituted $(C_6–C_{10})$-aryloxy, $(C_1–C_6)$-alkylcarbonyloxy-$(C_1–C_4)$-alkoxy, $(C_6–C_{10})$-arylcarbonyloxy-$(C_1–C_4)$-alkoxy optionally substituted in the aryl radical, amino or mono- or di-$((C_1–C_8)$-alkyl)amino;

$R^{11}$ is hydrogen, $R^{12a}$, $R^{12a}$—CO, $R^{12a}$—O—CO, $R^{12b}$—CO or $R^{12a}$—S(O)$_2$;

$R^{12a}$ is $(C_1–C_8)$-alkyl, $(C_2–C_8)$-alkenyl, $(C_2–C_8)$-alkynyl, $(C_5–C_6)$-cycloalkyl, $(C_5–C_6)$-cycloalkyl-$(C_1–C_4)$-alkyl, optionally substituted $(C_6–C_{10})$-aryl, $(C_6–C_{10})$-aryl-$(C_1–C_4)$-alkyl optionally substituted in the aryl radical, optionally substituted heteroaryl, heteroaryl-$(C_1–C_4)$-alkyl optionally substituted in the heteroaryl radical, or the radical $R^{15}$;

$R^{12b}$ is amino, di-$((C_1–C_8)$-alkyl)amino or $R^{12a}$—NH;

$R^{13}$ is hydrogen or $(C_1–C_6)$-alkyl;

$R^{15}$ is $R^{16}$—$(C_1–C_6)$-alkyl or $R^{16}$;

$R^{16}$ is a radical of a 6-membered to 12-membered bicyclic or tricyclic ring which is saturated or partially unsaturated and which optionally may contain one, two, three or four identical or different heteroatoms selected from the group consisting of nitrogen, oxygen and sulfur and which is optionally substituted by one or more identical or different substituents selected from the group consisting of $(C_1–C_4)$-alkyl and oxo;

$R^{20}$ is a direct bond or methylene;

$R^{21}$ is hydrogen, $(C_1–C_6)$-alkyl, optionally substituted $(C_6–C_{10})$-aryl, $(C_6–C_{10})$-aryl-$(C_1–C_2)$-alkyl optionally substituted in the aryl radical, the radical Het- or Het-$(C_1–C_2)$-alkyl, where alkyl radicals optionally monosubstituted to tetrasubstituted by fluorine and the radicals $R^{21}$, if they occur a number of times, may be identical or different;

$R^{30}$ is one of the radicals $R^{32}$—CR=CR—$R^{31}$— or $R^{32}$—C≡C—$R^{31}$—, where the radicals R independently of one another have one of the meanings indicated and may be identical or different;

$R^{31}$ is a divalent radical selected from the group consisting of optionally substituted $(C_6–C_{10})$-arylene, $(C_6–C_{10})$-arylene-$(C_1–C_4)$-alkyl optionally substituted in the arylene radical, $(C_5–C_6)$-cycloalkylene, $(C_5–C_6)$-cycloalkylene-$(C_1–C_4)$-alkyl, optionally substituted heteroarylene or heteroarylene-$(C_1–C_4)$-alkyl optionally substituted in the heteroarylene radical, where in the case of the arylenealkyl radical, the cycloalkylene-alkyl radical and the heteroarylenealkyl radical the alkyl group is bonded to the nitrogen atom in the imidazolidine ring in the formula i;

$R^{32}$ is hydrogen, $(C_2–C_6)$-alkenyl, $(C_2–C_6)$-alkynyl, $(C_5–C_6)$-cycloalkyl, $(C_5–C_6)$-cycloalkyl $(C_1–C_4)$-alkyl, optionally substituted $(C_6–C_{10})$-aryl, $(C_6–C_{10})$-aryl-$(C_1–C_4)$-alkyl optionally substituted in the aryl radical, optionally substituted heteroaryl, heteroaryl-$(C_1–C_4)$-alkyl optionally substituted in the heteroaryl radical or $(C_1–C_6)$-alkyl which is optionally substituted by 1 to 6 fluorine atoms;

Het is a radical of a monocyclic or polycyclic, 5-membered to 10-membered, aromatic or nonaromatic ring which contains 1 or 2 identical or different heteroatoms selected from the group consisting of N and O as ring members and is optionally substituted by one or more, identical or different substituents;

e and h independently of one another are 0 or 1 and may be identical or different;

in all its stereoisomeric forms and mixtures thereof in all ratios, or its physiologically tolerable salts.

5. A compound of the formula I as claimed in claim 4 in which B is unsubstituted methylene or methylene which is substituted by a $(C_1–C_8)$-alkyl radical, in all its stereoisomeric forms and mixtures thereof in all ratios, or its physiologically tolerable salts.

6. A process for the preparation of a compound of the formula I as claimed in claim 1, which comprises carrying out a fragment condensation of a compound of the formula II

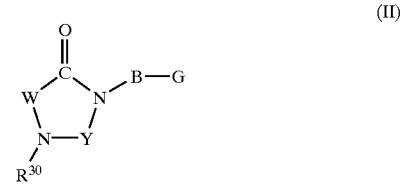

with a compound of the formula III,

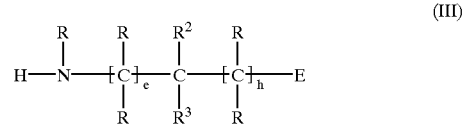

where, in the formulae II and III, the groups W, Y, B, E, R, $R^2$, $R^3$, $R^{30}$ as well as e and h are as defined in claim 1 or alternatively functional groups may be present in protected form or in the form of precursors, and where G is hydroxycarbonyl, $(C_1-C_6)$-alkoxycarbonyl or activated carboxylic acid derivatives.

7. A pharmaceutical preparation comprising one or more compounds of the formula I as claimed in one of claims 1–5 and/or its physiologically tolerable salts and a pharhaaceutically acceptable carrier.

8. A method for treating inflammation comprising administering to a subject in need thereof, a compound of the formula I as claimed in claim 1.

9. A method for treating arthritis, rheumatoid arthritis, polyarthritis, inflammatory bowel disease, systemic lupus erythematosus, multiple sclerosis or inflammatory disorders of the central nervous system comprising administering to a subject in need thereof, a compound of the formula I as claimed in claim 1.

10. A method for treating asthma or allergies comprising administering to a subject in need thereof, a compound of the formula I as claimed in claim 1.

11. A method for treating cardiovascular disorders, arteriosclerosis, restenoses, diabetes, damage to organ transplants, immune disorders, autoimmune disorders, tumor growth or formation of tumor metastases or malaria, comprising administering to a subject in need thereof, a compound of the formula I as claimed in claim 1.

12. A method for inhibiting adhesion and/or the migration of leukocytes, comprising administering to a subject in need thereof, a compound of the formula I as claimed in claim 1.

13. A method for inhibiting a VLA-4 receptor, comprising administering to a subject in need thereof, a compound of the formula I as claimed in claim 1.

* * * * *